US008404678B2

(12) United States Patent
Bouchard et al.

(10) Patent No.: US 8,404,678 B2
(45) Date of Patent: Mar. 26, 2013

(54) CYTOTOXIC AGENTS COMPRISING NEW TOMAYMYCIN DERIVATIVES AND THEIR THERAPEUTIC USE

(75) Inventors: Hervé Bouchard, Paris (FR); Ravi V. J. Chari, Waltham, MA (US); Alain Commerçon, Paris (FR); Yonghong Deng, Waltham, MA (US); Laurence Gauzy, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/689,797

(22) Filed: Jan. 19, 2010

(65) Prior Publication Data

US 2010/0316656 A1    Dec. 16, 2010

Related U.S. Application Data

(63) Continuation of application No. PCT/IB2008/002869, filed on Jul. 18, 2008.

(30) Foreign Application Priority Data

Jul. 19, 2007    (EP) .................................... 07290904

(51) Int. Cl.
*C07D 487/00*    (2006.01)
*C07D 519/00*    (2006.01)
*A61K 31/5517*    (2006.01)

(52) U.S. Cl. ........................................ 514/220; 540/496
(58) Field of Classification Search .................. 540/496; 514/220
See application file for complete search history.

(56) References Cited

U.S. PATENT DOCUMENTS

| 5,208,020 | A  | 5/1993  | Chari et al. |
| 5,416,064 | A  | 5/1995  | Chari et al. |
| 5,475,092 | A  | 12/1995 | Chari et al. |
| 5,585,499 | A  | 12/1996 | Chari et al. |
| 6,340,701 | B1 | 1/2002  | Chari et al. |
| 6,372,738 | B2 | 4/2002  | Chari et al. |
| 6,436,931 | B1 | 8/2002  | Chari et al. |
| 6,756,397 | B2 | 6/2004  | Zhao et al.  |

FOREIGN PATENT DOCUMENTS

| EP | 0 306 943        | 3/1989  |
| FR | 1 516 743        | 2/1968  |
| WO | WO 00/12507      | 3/2000  |
| WO | WO 00/12508      | 3/2000  |
| WO | WO 2004/043344 A2 | 5/2004 |
| WO | WO 2004/091542 A2 | 10/2004 |
| WO | WO 2005/009369 A2 | 2/2005 |
| WO | WO 2005/023814   | 3/2005  |
| WO | WO 2005/040170 A2 | 5/2005 |
| WO | WO 2005/061541 A1 | 7/2005 |
| WO | WO 2005/085250 A1 | 9/2005 |
| WO | WO 2005/085260 A1 | 9/2005 |
| WO | WO 2007/085930   | 8/2007  |
| WO | WO 2008/010101   | 1/2008  |
| WO | WO 2008/047242 A2 | 4/2008 |

OTHER PUBLICATIONS

Zeng et al, Rapid Synthesis of Dendrimers by an Ortogonal Coupling Strategy, J. Am. Chem., Soc. 1996 (118) pp. 5326-5327.
Burgess, The complex mediators of cell growth and differentiation, Immunol. Today 1984 (5) 6 pp. 155-158.
Chari, Targeted Delivery of Chemotherapeutics: Tumor-Activated Prodrug Therapy, Advanced Drug Delivery Reviews 1998 (31) pp. 89-104.
Dillman et al, Preclinical Trials with Combinations and Conjugates of T101 Monoclonal Antibody and Doxorubicin, Cancer Research 1986 (46) pp. 4886-4891.
Endo et al, In Vitro Cytotoxicity of a Human Serum Albumin-Mediated Conjugate of Methotrexate with Anti-MM46 Monoclonal Antibody, Cancer Research 1987 (47) pp. 1076-1080.
Erickson et al., Antibody-Maytansinoid Conjugate Are Activated in Targeted Cancer Cells by Lysosomal Degradation and Linker-Dependent Intracellular Processing, Cancer Research, American Assoc. For Cancer Research, Apr. 15, 2006, pp. 4426-4433, XP008074767, ISSN: 0008-5472.
Farmer et al, Synthesis and DNA Crosslinking Ability of a Dimeric Anthramycin Analog, Tetrahedron Letters, vol. 29, No. 40, pp. 5105-5108, 1988.
Felder et al, Synthesis of Amphiphilic Fullerene Derivatives and Their Incorporation in Langmuir and Langmuir-Blodgett Films, Helv. Chimica Acta 2002 (85) pp. 288-319.
Foulon et al, Preparation and Characterization of Anti-Tenascin Monoclonal Antibody-Streptavidin Conjugates for Pretargeting Applications, Bioconjugate Chem. 1999 (10) pp. 867-876.
Garnett et al, An Improved Synthesis of a Methotrexate-Albumin-791T/36 Monoclonal Antibody Conjugate Cytotoxic to Human Osteogenic Sarcoma Cell Lines, Cancer Research 1986 (46) pp. 2407-2412.
Goldmacher et al, Antibody-complement-mediated cytotoxicity is enhanced by ribosome-inactivating proteins, J. Immunol. 1985 (135) pp. 3648-3651.
Goldmacher et al, Evidence That Pinocytosis in Lymphoid Cells Has a Low Capacity, J. Cell Biol. 1986 (102) pp. 1312-1319.
Griffin et al, A Monoclonal Antibody Reactive with Normal and Leukemic Human Myeloid Progenitor Cells, Leukemia Res. 1984 (8) 4 pp. 521-534.
Hamann et al, Monoclonal Antibody-Drug Conjugates, Expert Opinion Ther. Patents 2005 (15) 9 pp. 1087-1103.
Hurwitz et al, Soluble Macromolecules as Carriers for Daunorubicin, Journal of Applied Biochemistry 1980 (2) pp. 25-35.
Kato et al, A Novel Method of Conjugation of Daunomycin with Antibody with a Poly-L-Glutamic Acid Derivative as Intermediate Drug Carrier. An Anti-a-Fetoprotein Antibody-Daunomycin Conjugate, J. Med. Chem. 1984 (27) pp. 1602-1607.
Kovtun et al, Antibody-Drug Conjugates Designed to Eradicate Tumors with Homogeneous and Heterogeneous Expression of the Target Antigen, Cancer Res. 2006 (66) 6 pp. 3214-3221.
Kumar et al, Design, synthesis and in vitro cytotoxic studies of novel bis-pyrrolo[2,1][1,4] benzodiazepine-pyrrole and imidazole polyamide conjugates, EP J Med Chem. 2005 (40) pp. 641-654.
Lambert, Drug-conjugated monoclonal antibodies for the treatment of cancer, Curr. Opin. Pharmac. 2005 (5) pp. 543-549.

(Continued)

*Primary Examiner* — Bruck Kifle
(74) *Attorney, Agent, or Firm* — Sandra Brockman-Lee

(57) ABSTRACT

The invention relates to novel tomaymicine derivatives comprising a linker. It also relates to the conjugate molecules that comprise one or more of said tomaymicine derivatives covalently linked to a cell binding agent through a linking group that is present on the linker of the tomaymycin derivative. It also relates to the preparation of the tomaymicine derivatives and of the conjugate molecules.

28 Claims, 24 Drawing Sheets

OTHER PUBLICATIONS

Liu et al, Eradication of Large Colon Tumor Xenografts by Targeted Delivery of Maytansinoids, PNAS 1996 (93) pp. 8618-8623.

Manabe et al, Production of a Monoclonal Antibody-Mitomycin C Conjugate, Utilizing Dextran T-40, and Its Biological Activity, Biochem. Pharmacol. 1985 (34) 2 pp. 289-291.

Mori et al, Total Syntheses of Prothracarcin and Tomaymycin by Use of Palladium Catalyzed Carbonylation, Tetrahedron 1986 (42) 14 pp. 3793-3806.

Nadler et al, B4, a human B lymphocyte-associated antigen expressed on normal, mitogen-activated, and malignant B lymphocytes, J. Immunol. 1983 (131) pp. 244-250.

Nisonoff et al, Separation of Univalent Fragments from the Bivalent Rabbit Antibody Molecule by Reduction of Disulfide Bonds, Archives Biochem. Biophys. 1960 (89) pp. 230-244.

O'Keefe et al, Characterization of a Transferrin-Diphtheria Toxin Conjugate, J. Biol. Chem. 1985 (260) 2 pp. 932-937.

Ohkawa et al, Selective in vitro and in vivo growth inhibition against human yolk sac tumor cell lines by purified antibody against human alpha-fetoprotein conjugated with mitomycin C via human serum albumin, Cancer Immuno Immunother 1986 (23) pp. 81-86.

Parham, On the fragmentation of monoclonal IgG1, IgG2a, and IgG2b from BALB/c mice, J. Immunol. 1983 (131) pp. 2895-2902.

Pietersz et al, Antibody-Targeted Drugs for the Therapy of Cancer, Journal of Drug Targeting 1994 (2) pp. 183-215.

Puzanov et al, Poster Session B: Clinical Trials: Phase I, II, and III Adult Clinical Trials—Proc. AACR-NCI-EORTC International Conference, Philadelphia, USA 2005; Abstract #B117—pp. 156, Molecular Targets and Cancer Therapeutics.

Ranson et al, Perspectives on Anti-HER Monoclonal Antibodies, Oncology 2002 (63) suppl 1 pp. 17-24.

Scrimin et al, Aggregate Structure and Ligand Location Strongly Influence Cu2+ Binding Ability of Cationic Metallosurfactants, J. Org. Chem. 1989 (54) pp. 5988-5991.

Shouval et al, Doxorubicin Conjugates of Monoclonal Antibodies to Hepatoma-Associated Antigens, PNAS 1988 (85) pp. 8276-8280.

Spring et al, Allotypic Markers on Fab Fragments of Mouse Immunoglobulins, J. Immunol. 1974 (113) 2 pp. 470-478.

Tozuka et al, Studies on Tomaymycin. II Total Syntheses of the Antitumor antibiotics, E-and Z-Tomaymycins, J. Antibiot. 1983 (36) 3 pp. 276-282.

Tsukada et al, an Anti-a-Fetoprotein Antibody-Daunorubicin Conjugate With a Novel Poly-L-Glutamic Acid Derivative as Intermediate Drug Carrier, JNCI 1984 (73) 3 pp. 721-729.

Tsukada et al, Suppression of Human a-Foetoprotein-Producing Hepatocellular Carcinoma Growth in Nude Mice by an Anti a-Foetoprotein Antibody-Daunorubicin Conjugate with a Poly-L-Glutamic Acid Derivatives as Intermediate Drug Carrier, Br. J. Cancer 1985 (52) pp. 111-116.

International Search Report for WO2009/016516 dated Feb. 5, 2009.

CYTOTOXIC AGENTS COMPRISING NEW TOMAYMYCIN DERIVATIVES AND THEIR THERAPEUTIC USE

FIELD OF THE INVENTION

The present invention relates to novel tomaymycin derivatives and their therapeutic use as cytotoxic agents. The therapeutic use is the result of delivering the tomaymycin derivatives to a specific cell population in a targeted fashion by chemically linking the tomaymycin derivative to a cell binding agent. The invention relates also to conjugate molecules comprising one or more of said tomaymycin derivatives chemically linked to a cell binding agent, optionally modified.

BACKGROUND OF THE INVENTION

Many reports have appeared on the attempted specific targeting of tumor cells with monoclonal antibody-drug conjugates (Sela et al, in *Immuno-conjugates*, 189-216 (C. Vogel, ed. 1987); Ghose et al, in *Targeted Drugs* 1-22 (E. Goldberg, ed. 1983); Diener et al, in *Antibody mediated delivery systems*, 1-23 (J. Rodwell, ed. 1988); Pietersz et al, in *Antibody mediated delivery systems*, 25-53 (J. Rodwell, ed. 1988); Bumol et al, in *Antibody mediated delivery systems*, 55-79 (J. Rodwell, ed. 1988); G. A. Pietersz & K. Krauer, 2, *J. Drug Targeting*, 183-215 (1994); R. V. J. Chari, 31 *Adv. Drug Delivery Revs.*, 89-104 (1998); W. A. Blattler & R. V. J. Chari, in *Anticancer Agents, Frontiers in Cancer Chemotherapy*, 317-338, ACS Symposium Series 796; Ojima et al eds, *American Chemical Society* 2001; J. M. Lambert, 5 *Current Opinion in Pharmacology*, 543-549 (2005); P. R. Hamann, 15 *Expert Opinion on Therapeutics Patents*, 1087-1103 (2005)). All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46, *Cancer Res.* 2407-2412 (1986); Ohkawa et al 23, *Cancer Immunol. Immunother.* 81-86 (1986); Endo et al, 47 *Cancer Res.* 1076-1080 (1980), dextran (Hurwitz et al, 2 *Appl. Biochem.* 25-35 (1980); Manabi et al, 34 *Biochem. Pharmacol.* 289-291 (1985); Dillman et al, 46 *Cancer Res.*, 4886-4891 (1986); Shoval et al, 85, *Proc. Natl. Acad. Sci.*, 8276-8280 (1988)), or polyglutamic acid (Tsukada et al, 73, *J. Natl. Canc. Inst.*, 721-729 (1984); Kato et al, 27 *J. Med. Chem.*, 1602-1607 (1984); Tsukada et al, 52, *Br. J. Cancer*, 111-116 (1985)).

A wide array of linker technologies has been employed for the preparation of such immunoconjugates and both cleavable and non-cleavable linkers have been investigated. In most cases, the high cytotoxic potential of the drugs could only be observed, however, if the drug molecules could be released from the conjugates in unmodified form at the target site using a cleavable linker.

In vitro cytotoxicity tests, however, have revealed that antibody-drug conjugates could kill not only antigen-positive cells, but also other cells in the vicinity, irrespective of the antigen expression on their surface. This phenomenon is called the bystander effect. This effect was observed in conjugates of the anti-CanAg antibody, huC242, with maytansinoids and with a CC1065 analog (Erickson et al, 66 *Cancer Res.*, 4426-4433 (2006); Kovtun et al, 66 *Cancer Res.*, 3214-3221 (2006)). So far only conjugates linked via a cleavable bond such as reducible disulfide bond demonstrated bystander cytotoxicity, while conjugates linked via a non-reducible thioether link exhibited no bystander effect.

Highly potent cytotoxic effector molecules linked to targeting agents such as antibodies could generate potent drug derivatives after intra-cellular processing of the conjugate. This could be an issue if generated cellular metabolites display undesired or not easily manageable side effects. In order to control the toxicity of antibody-drug conjugates, it could be very beneficial to use non-cleavable linkers.

Another major drawback with most antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream. So an alternative is to use much more potent drug molecules such as the ones disclosed herebelow.

Non cleavable linkers have been also used in conjugation. They have an interest in radioimmunotherapeutic applications in particular. This has been also utilized in the attachment of toxins to monoclonal antibodies, as for Pseudomonas exotoxin with MAb 9.2.27 using heterobifunctional maleimide succinimidyl 4-(N-maleimidomethyl)cyclohexane-1-carboxylate (SMCC) (EP 306943). The MAb toxin conjugate turned out to be of greater specificity in vitro against positive cell lines than the corresponding disulfide bond conjugate and thus less toxic in mouse models. Nonspecific toxicity is significantly decreased when a noncleavable linker is used. This non-cleavable linker has been used in the case of trastuzumab (Herceptin) which target HER2 (ErbB) HERR2 is a key target and methods are being investigated to maximize the effect of using MAbs to inhibit this receptor. One approach aims to augment the efficacy of trastuzumab (Herceptin) by coupling it to a chemotherapeutic agent, thus enabling the delivery of cytotoxic therapy at a cellular level (Ranson and Sliwkowski, 63 (Suppl. 1) *Oncology*, 17-24 (2002)).

Other versions of the SMCC reagent exist, for instance water soluble sulfosuccinimidyl 4-(N-maleimidomethyl)cyclohexane-1-carboxylate (sulfo-SMCC), has been also used in conjugation reaction. Other non-cleavable linkers include in particular N-succinimidyl-S-acetylthioacetae (SATA), SATA-SMCC, 2-iminothiazole (2IT) and 2IT-SMCC (Foulon et al, 10, *Bioconjugate Chem.*, 867-876 (1999)). Crosslinking reagents comprising a haloacetyl-based moiety have also been used and include N-succinimidyl-4-(iodoacetyl)-aminobenzoate (SIAB), N-succinimidyl iodoacetate (SIA), N-succinimidyl bromoacetate (SBA) and N-succinimidyl 3-(bromo-acetamido)propionate (SBAP). These crosslinking reagents form non-cleavable linkers derived from haloacetyl-based moieties.

In spite of the above-reported difficulties because of the drug molecules, useful cytotoxic agents comprising cell binding moieties and the group of cytotoxic drugs known as maytansinoids have been reported (U.S. Pat. No. 5,208,020, U.S. Pat. No. 5,416,064, and R. V. J. Chari, 31 *Advanced Drug Delivery Reviews* 89-104 (1998)). Similarly, useful cytotoxic agents comprising cell binding moieties and analogues and derivatives of the potent antitumor antibotic CC-1065 have also been reported (U.S. Pat. No. 5,475,092, U.S. Pat. No. 5,585,499 and U.S. Pat. No. 6,756,397).

Tomaymycin derivatives are pyrrolo[1,4]benzodiazepines (PBDs), a known class of compounds exerting their biological properties by covalently binding to the N2 of guanine in the minor groove of DNA. PBDs include a number of minor groove binders such as anthramycin, neothramycin and DC-81. Tomaymycin antitumor activity is however limited because of its non-specific toxicity towards normal cells. Thus there is a need to increase the therapeutic activity, and diminish the non-specific toxic effects of tomaymycin compounds. The present inventors have shown that this need can be met by targeted delivery of tomaymcin compounds by linking them to cell binding agents. Additionally, there is a need to develop tomaymycin derivatives that are soluble and stable in aqueous solutions. Further, tomaymycin is not sufficiently potent to be used in conjugates of cell binding agents.

Recently, a few new PBD derivatives and their anti-tumour activity in preclinical models have been disclosed (WO 00/12508 and WO 2005/085260). However, initial clinical trials in humans indicate that compounds of this class are severely toxic, based on the very low dose that can be administered to humans (I. Puzanov, Proc. AACR-NCI-EORTC International Conference, Philadelphia, USA 2005, Abstract #B117). Thus, it is desired to provide alternative derivatives showing lesser side effects without compromising the cytotoxic activity.

International applications WO 2007/085930 and WO 2008/010101 describe tomaymicin derivatives that can be linked to a cell binding agent through a linker, but the linker is not a linker as defined for the compounds of the invention.

Article "Tetrahedron Letters, Vol. 29, N°40, pp. 5105-5108" describes tomaymicin derivatives ref. (13)-(15) without any linker.

International application WO 2005/085250 describes dimers of PBDs of general formula PBD-A-Y—X-(Het)$_{na}$-L-(Het)$_{nb}$-L-(Het)$_{nc}$-T-(Het')$_{nd}$-L-(Het')$_{ne}$-L-(Het')$_{nf}$-X'—Y'-A'-PBD' wherein Het and Het' are amino-heteroarylene-groups of formulae -J-G-J' or J'-G-J- where G is an optionally substituted heteroarylene, $n_a$-$n_f$ are integers between 0 and 5, L can be β-alanine, glycine, 4-aminobutanoic acid or a single bond. X and X' are both either —NH— or —C(=O)— and Y and Y' are divalent groups such that HY is an alkyl, heterocyclyc or aryl group or a single bond. A and A' are selected from O, S, NH or a single bond. T is a divalent linker of the form —NH-Q-NH— or —C(=O)-Q-C(=O)— where Q is divalent group such that QH is an alkyl, heterocyclyc or aryl group (optionally substituted). The compounds according to the general formula all comprise —NH— or —C(=O)— as X and X' and —NH-Q-NH— or —C(=O)-Q-C(=O)— which is not the case for the compounds of the invention.

International application WO 2005/023814 describes dimers of PBDs protected on the nitrogen atom N10 by R$_{10}$—COO— comprising a bridge —X—R"—X— wherein R" is an alkylene group optionally interrupted by one or more heteroatoms NH, O or S and/or aromatic rings and X is O, S or NH. There is no mention of a linker on the bridge —X—R"—X—. Moreover, the compounds of the invention are not protected on N10.

Article "European Journal of Medicinal Chemistry Vol. 40, N°7, pp. 641-654" describes dimers of PBDs ref. (38)-(40) that do not comprise any linker as for the compounds of the invention.

Article "Expert opinion; Monoclonal antibody-drug conjugates", Ashley publications, Vol. 15, N°9, 2005, pp. 1087-1103, ISSN:1354-3774 does not describe the compounds of the invention and article "Cancer Res. 2006, 66(8), pp. 4426-4433" describes maytansinoid linked to cell binding agents.

SUMMARY OF THE INVENTION

The invention relates to novel tomaymicine derivatives comprising a linker. It also relates to the conjugate molecules that comprise one or more of said tomaymicine derivatives covalently linked to a cell binding agent through a linking group that is present on the linker of the tomaymycin derivative. It also relates to the preparation of the tomaymicine derivatives and of the conjugate molecules.

DETAILED DESCRIPTION OF THE INVENTION

Definitions

Figure 1:
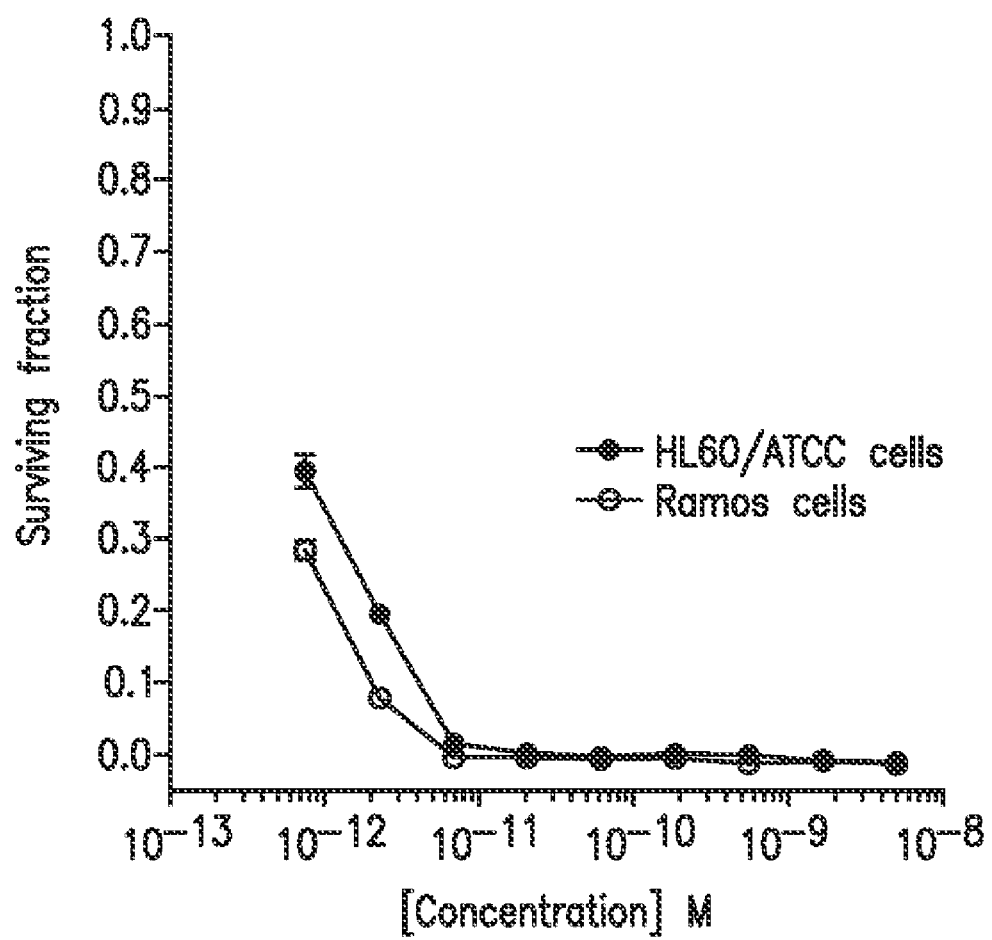
FIG. 1: In vitro cytotoxicity of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester of ex. 1.

Alk represents alkyl, alkene or alkyne;

"Alkyl" means an aliphatic hydrocarbon group which may be straight or branched having 1 to 20 carbon atoms in the chain or cycle having 3 to 10 carbon atom. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl and cyclohexyl;

"Alkene" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, and decenyl;

"Alkyne" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl;

"Halogen atom" refers to fluorine, chlorine, bromine or iodine atom; preferably fluorine and chlorine atom;

"Aryl" means an aromatic monocyclic or multicyclic hydrocarbon ring system of 6 to 14 carbon atoms, preferably of 6 to 10 carbon atoms. Exemplary aryl groups include phenyl or naphthyl;

"Het" means heterocycle or heteroaryl;

the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in *The Handbook of Chemistry and Physics*, 76th Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrinidinyl, dihydrothiopyranyl, azepanyl, as well as the fused systems resulting from the condensation with a phenyl group;

the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group;

"Alkyl", "cycloalkyl", "alkenyl", "alkynyl", "aryl", "heteroaryl", "heterocycle" and the like refer also to the corresponding "alkylene", "cycloalkylene", "alkenylene", "alkynylene", "arylene", "heteroarylene", "heterocyclene" and the likes which are formed by the removal of two hydrogen atoms;

"non-cleavable linkers" means any group suitable for covalently linking said tomaymycin derivative to a cell binding agent, wherein said group does not contain disulfide groups, acid labile groups, photolabile groups, peptidase labile groups and esterase labile groups. Preferably, said "non-cleavable linkers" comprise a terminal carboxy or amide group, or precursors thereof. The linker is not cleaved during the intracellular processing after internalisation of the conjugate molecule inside the cell and potential proteolysis of the cell binding agent;

the expression "linkable to a cell binding agent" refers to the tomaymycin derivatives comprising at least one linker, which in turn comprises a linking group, or a precursor thereof, suitable to bond said derivatives to a cell binding agent; preferred linking groups are carboxy, amide bonds, or precursors thereof;

the expression "linked to a cell binding agent" refers to the conjugate molecule comprising at least one tomaymycin derivative bound to a cell binding agent via a suitable linking group, or a precursor thereof; preferred linking groups are non-cleavable bonds, or precursors thereof;

"precursor" of a given group refers to any group which may lead to that group by any deprotection, chemical modification, or coupling reaction;

"patient" refers to either an animal, such as a valuable animal for breeding, company or preservation purposes, or preferably a human or a human child, which is afflicted with, or has the potential to be afflicted with one or more diseases and conditions described herein;

"therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment;

"pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio;

"pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"treating" or "treatment" means reversing, alleviating, inhibiting the progress of, or preventing the disorder or condition to which such term applies, or one or more symptoms of such disorder or condition.

"therapeutically effective amount" means an amount of a compound/medicament according to the present invention effective in preventing or treating the herein referred pathological condition;

"pharmaceutically" or "pharmaceutically acceptable" refer to molecular entities and compositions that do not produce an adverse, allergic or other untoward reaction when administered to an animal, or a human, as appropriate;

"pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

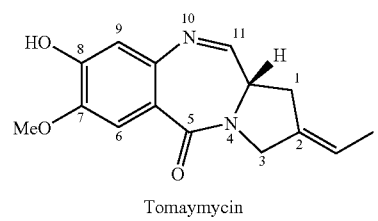

Tomaymycin

The cytotoxic agent according to the present invention comprises one or more tomaymycin derivatives, optionally linkable or linked to a cell binding agent via a non-cleavable linking group. The linking group is part of a chemical moiety that is covalently bound to a tomaymycin derivative through conventional methods.

According to one aspect, the invention relates to tomaymycin derivatives of formula (I):

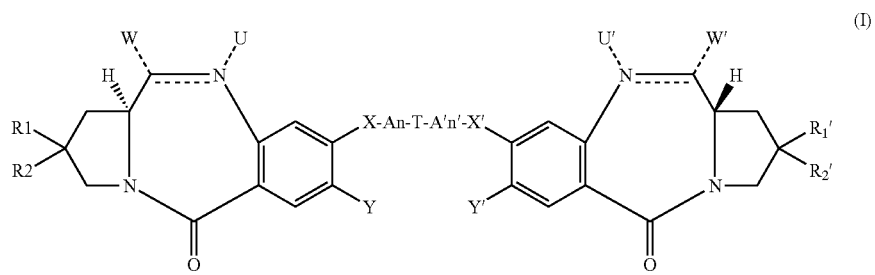

(I)

Tomaymycin Derivatives

The invention is based on the synthesis of novel tomaymycin derivatives that retain high cytotoxicity and that can be effectively linked to cell binding agents with non-cleavable linkers, such conjugates demonstrating high potency in killing tumor cells. It has previously been shown that the linkage of highly cytotoxic drugs to antibodies using a cleavable link, such as a disulfide bond, ensures the release of fully active drugs inside the cell, and such conjugates are cytotoxic in an antigen specific manner (U.S. Pat. No. 6,340,701; U.S. Pat. No. 6,372,738; U.S. Pat. No. 6,436,931). However, the art reveals that it is extremely difficult to modify existing drugs without diminishing their cytotoxic potential. The disclosed invention overcomes this problem by modifying the disclosed tomaymycin derivatives with chemical moieties. As a result, the disclosed novel tomaymycin derivatives preserve, and in some cases could even enhance the cytotoxic potency of tomaymycin derivatives. The cell binding agent-tomaymycin derivative complexes permit the full measure of the cytotoxic action of the tomaymycin derivatives to be applied in a targeted fashion against unwanted cells only, therefore, avoiding side effects due to damage to non-targeted healthy cells. Thus, the invention provides useful agents for the elimination of diseased or abnormal cells that are to be killed or lysed such as tumor cells (particularly solid tumor cells).

wherein:

▭▭▭▭▭ represents an optional single bond;

▭ ▭ ▭ ▭ represents either a single bond or a double bond;

provided that when ▭ ▭ ▭ ▭ represents a single bond, U and U', the same or different, independently represent H, and W and W', the same or different, are independently selected from the group consisting of OH, an ether such as —OR, an ester (e.g. an acetate), such as —OCOR or —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —$SO_3^-$, a sulfonamide such as —NRSOOR', an amine such as —NRR', optionally cyclic amine such that N10 and C11 are a part of the cycle, a hydroxylamine derivative such as —NROR', an amide such as —NRCOR', an azido such as —$N_3$, a cyano —CN, a halide (Hal), a trialkyl or triarylphosphonium; preferably W and W' are the same or different and are —OH, —OMe, —OEt, —NHCONH$_2$, —SMe; and when ▭ ▭ ▭ ▭ represents a double bond, U and U' are absent and W and W' represent H.

R1, R2, R1', R2' are the same or different and independently chosen from H, Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively.

Preferably, R1 and R2 and R1' and R2' form together a double bond containing group =B and =B' respectively.

B and B' are the same or different and independently chosen from Alkenyl being optionally substituted by one or more Hal, CN, NRR', CF$_3$, OR, SR, SOR, SO$_2$R, Aryl, Het, or B and B' represent an oxygen atom.

Preferably, B=B'.

More preferably, B=B'==CH$_2$ or =CH—CH$_3$,

X, X' are the same or different and independently chosen from one or more —O—, —S—, —NR—, —(C=O)—, —SO—, —SO$_2$—;

Preferably, X=X'.

More preferably, X=X'=O.

A, A' are the same or different and independently chosen from Alkyl or Alkenyl, each being optionally substituted by one or more Hal, CN, NRR', CF$_3$, OR, SR, SOR, SO$_2$R, Aryl, Het, Alkyl, Alkenyl.

Preferably, A=A'.

More preferably, A=A'=linear unsubstituted alkyl.

Y, Y' are the same or different and independently chosen from H, OR;

Preferably, Y=Y'.

More preferably, Y=Y'=OAlkyl, more preferably OMethyl.

T is —NR— or a 4 to 10-membered aryl, cycloalkyl, heterocyclic, heteroaryl or a linear or branched alkyl, each being substituted by one or more non-cleavable linker(s) and optionally substituted by one or more of Hal, CN, NRR', CF$_3$, R, OR, SOR or SO$_2$R.

n, n', equal or different, are 0 or 1;

q is 0, 1 or 2;

According to a variant aspect, the tomaymycin derivatives are of formula (I'):

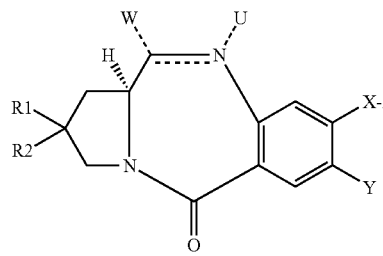
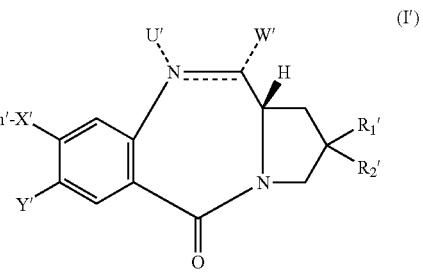

(I')

wherein R1, R1', R2, R2', W, W', U, U', Y, Y', X, X', A, A', n, n' are as described above and T is —NR— or a 4 to 10-membered aryl, cycloalkyl, heterocyclic, heteroaryl or a linear or branched alkyl, each being substituted by one or more linker(s) of formula -G-D-(Z)$_p$—C(=O)—Z'R" and optionally substituted by one or more of Hal, CN, NRR', CF$_3$, R, OR, SOR, SO$_2$R.

The bridging group —X-A$_n$-T-A'$_n$-X'— does not contain any —NH—C(=O)— link.

The linker is of formula:

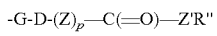

wherein:

G is a single, a double or a triple bond, —O—, —S— or —NR—;

D is a single bond or -E-, -E-NR—, -E-NR—F—, -E-O—, -E-O—F—, -E-NR—CO—, -E-CO—NR—, -E-NR—CO—F—, -E-CO—NR—F—, -E-CO—, —CO-E-, -E-CO—F, -E-S—, -E-S—F—, -E-NR—CS—, -E-CS—NR—, -E-NR—CS—F—, -E-CS—NR—F—;

E and F are the same or different and are independently chosen from linear or branched —(OCH$_2$CH$_2$)$_i$Alkyl (OCH$_2$CH$_2$)$_j$—, -Alkyl(OCH$_2$CH$_2$)$_i$-Alkyl-, —(OCH$_2$CH$_2$)$_j$—, —(OCH$_2$CH$_2$)$_i$Cycloalkyl (OCH$_2$CH$_2$)$_j$—, —(OCH$_2$CH$_2$)$_i$Heterocyclic (OCH$_2$CH$_2$)$_j$—, —(OCH$_2$CH$_2$)$_i$Aryl(OCH$_2$CH$_2$)$_j$—, —(OCH$_2$CH$_2$)$_i$Heteroaryl(OCH$_2$CH$_2$)$_j$—, -Alkyl-(OCH$_2$CH$_2$)$_i$Alkyl(OCH$_2$CH$_2$)$_j$—, -Alkyl-(OCH$_2$CH$_2$)$_i$—, -Alkyl-(OCH$_2$CH$_2$)$_i$Cycloalkyl(OCH$_2$CH$_2$)$_j$—, -Alkyl(OCH$_2$CH$_2$)$_i$Heterocyclic(OCH$_2$CH$_2$)$_j$—, -Alkyl-(OCH$_2$CH$_2$)$_i$Aryl(OCH$_2$CH$_2$)$_j$—, -Alkyl(OCH$_2$CH$_2$)$_i$Heteroaryl(OCH$_2$CH$_2$)$_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;

i and j, identical or different are integers and independently chosen from 0, 1 to 2000;

Z is a linear or branched Alkyl, cycloalkyl, Aryl, heteroaryl, heterocyclyl, aralkyl, cycloalkyl, heteroaralkyl, or heterocyclylalkyl, optionally substituted by solubilizing functions such as amino, ether, sulfonic and carboxylic groups;

p is 0 or 1;

—C(=O)—Z'R" is a carbonyl containing function wherein

Z' represents a single bond or —O—, —S—, —NR— and

R" represents H, Alkyl, Cycloalkyl, Aryl, heteroaryl or heterocyclic, each being optionally substituted by one or more Hal, CN, NRR', CF$_3$, R, OR, SOR, SO$_2$R, Aryl, Het;

R, R' are equal or different and independently chosen from H, Alkyl, Aryl, each being optionally substituted by Hal, CN, COOH, COOR, CONHR, CONRR', NRR', CF$_3$, R, OR, SOR, SO$_2$R, Aryl, Het.

The linker comprises a chain terminated by a linking group which does not contain any cleavable group such as a disulfide group, an acid labile group, a photolabile group, a peptidase labile group and an esterase labile group. The terminal linking group does not contain the —S—V group wherein V is H, a thiol protecting group (such as COR), $R_{20}$ or $SR_{20}$, $R_{20}$ being H, methyl, alkyl, optionally substituted cycloalkyl, aryl, heteroaryl or heterocyclic group. The linker is not any one disclosed in either WO 2007/085930 or in WO 2008/010101. The terminal linking group of the tomaymicin derivatives of the invention is preferably a carboxy or amide group, at the terminal end of the side chain. The side chain can be linear or branched, aromatic or heterocyclic. One of ordinary skill in the art can readily identify suitable side chains. Preferred linkers are composed of linear chains containing solubilizing functions such as amino, hydroxy, ether, sulfonic and carboxylic groups.

T is preferably a 4 to 10-membered aryl or heteroaryl, more preferably a phenyl or pyridyl group, substituted by one or more of said linker(s) and optionally substituted by one or more of Hal, CN, NRR', $CF_3$, R, OR, SOR or $SO_2R$. The pyridyl group provides a higher solubility of the tomaymicine derivative in aqueous solutions than the phenyl group. A higher solubility can help in the preparation of the conjugate molecule with a hydrophobic antibody as there tend to be lesser aggregates which may help increase the yields of the conjugate molecules.

The pharmaceutically acceptable salts, hydrates, or hydrated salts, or the polymorphic crystalline structures of the compounds along with the optical isomers, racemates, diastereomers or enantiomers also form part of the invention. When the compound is in the form of an ion (eg. sulphonate), the counter ion may be present (eg. $Na^+$ or $K^+$).

The present invention refers to following preferred embodiments or any combination of any of them:

G is a single bond or —O—;
D is a single bond or -E- or -E-O—;
D is -E-;
E is linear or branched -Alkyl- or -Alk($OCH_2CH_2$)$_i$—;
Z is linear or branched -Alkyl-;
p is 0;
Z' is a single bond or O;
Z' is O;
R" is H or linear or branched -Alkyl- or optionally substituted heterocyclic;
R" is H or alkyl or a succinimide group (

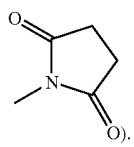

).

Specific examples of linkers include the following:
—$(CR_{13}R_{14})_t(CR_{15}R_{16})_u(OCH_2CH_2)_yCOZ'R''$,
—$(CR_{13}R_{14})_t(OCH_2CH_2)_yO(CR_{15}R_{16})_uCOZ'R''$,
—$(CR_{13}R_{14})_t(CR_{17}=CR_{18})(CR_{15}R_{16})_u(OCH_2CH_2)_yCOZ'R''$,
—$(CR_{13}R_{14})_t(NR_{19}CO)(CR_{15}R_{16})_u(OCH_2CH_2)_yCOZ'R''$,
—$(CR_{13}R_{14})_t(OCO)(CR_{15}R_{16})_u(OCH_2CH_2)_yCOZ'R''$,
—$(CR_{13}R_{14})_t(CO)(CR_{15}R_{16})_u(OCH_2CH_2)_yCOZ'R''$,
—$(CR_{13}R_{14})_t(CONR_{19})(CR_{15}R_{16})_u(OCH_2CH_2)_yCOZ'R''$,
—$(CR_{13}R_{14})_t$-phenyl-$CO(CR_{15}R_{16})_uCOZ'R''$, —$(C_{13}R_{14})_t$-furyl-$CO(CR_{15}R_{16})_uCOZ'R''$,
—$(CR_{13}R_{14})_t$-oxazolyl-$CO(CR_{15}R_{16})_uCOZ'R''$,
—$(CR_{13}R_{14})$-thiazolyl-$CO(CR_{15}R_{16})_uCOZ'R''$,
—$(CR_{13}R_{14})_t$-thienyl-$CO(CR_{15}R_{16})_uCOZ'R''$, —$(CR_{13}R_{14})_t$-imidazolyl-$CO(CR_{15}R_{16})_uCOZ'R''$,
—$(CR_{13}R_{14})_t$-piperazino-$CO(CR_{15}R_{16})_uCOZ'R''$,
—$(CR_{13}R_{14})_t$-phenyl-$QCOZ'R''$, —$(CR_{13}R_{14})_t$-furyl-$QCOZ'R''$, —$(CR_{13}R_{14})_t$-oxazolyl-$QCOZ'R''$,
—$(CR_{13}R_{14})_t$-thiazolyl-$QCOZ'R''$, —$(CR_{13}R_{14})_t$-thienyl-$QCOZ'R''$, —$(CR_{13}R_{14})_t$-imidazolyl-$QCOZ'R''$,
—$(CR_{13}R_{14})_t$-piperazino-$QCOZ'R''$,
—$(C\equiv C)$—$(CR_{13}R_{14})_t(CR_{15}R_{16})_u(OCH_2CH_2)_yCOZ'R''$,
—$O(CR_{13}R_{14})_t(CR_{15}R_{16})_u(OCH_2CH_2)_yCOZ'R''$,
—$O(CR_{13}R_{14})_t(NR_{19}CO)(CR_{15}R_{16})_u(OCH_2CH_2)_yCOZ'R''$,
—$O(CR_{13}R_{14})_t(CR_{17}=CR_{18})(CR_{15}R_{16})_u(OCH_2CH_2)_yCOZ'R''$,
—O-phenyl-$QCOZ'R''$, —O-furyl-$QCOZ'R''$, —O-oxazolyl-$QCOZ'R''$, —O-thiazolyl-Q $COZ'R''$,
—O-thienyl-$QCOZ'R''$, —O-imidazolyl-$QSCOZ'R''$,
—O-morpholino-$QCOZ'R''$, —O-piperazino-$QCOZ'R''$,
—$OCO(CR_{13}R_{14})_t(NR_{19}CO)(CR_{15}R_{16})_u(OCH_2CH_2)_yCOZ'R''$,
—$OCO$—$(CR_{13}R_{14})_t(CR_{17}=CR_{18})(CR_{15}R_{16})_u(OCH_2CH_2)_yCOZ'R''$,
—$OCONR_{12}(CR_{13}R_{14})_t(CR_{15}R_{16})_u(OCH_2CH_2)_yCOZ'R''$,
—OCO-phenyl-$QCOZ'R''$, —OCO-furyl-$QCOZ'R''$,
—OCO-oxazolyl-$QCOZ'R''$, —OCO-thiazolyl-$QCOZ'R''$,
—OCO-thienyl-$QCOZ'R''$, —OCO-imidazolyl-$QCOZ'R''$,
—OCO-piperazino-$QCOZ'R''$, or
—$CO(CR_{13}R_{14})_t(CR_{15}R_{16})_u(OCH_2CH_2)_yCOZ'R''$,
—$CO$—$(CR_{13}R_{14})_t(CR_{17}=CR_{18})(CR_{15}R_{16})_u(OCH_2CH_2)_yCOZ'R''$,
—$CONR_{12}(CR_{13}R_{14})_t(CR_{15}R_{16})_u(OCH_2CH_2)_yCOZ'R''$,
—CO-phenyl-$QCOZ'R''$, —CO-furyl-$QCOZ'R''$—CO-oxazolyl-$QCOZ'R''$, —CO-thiazolyl-$QCOZ'R''$,
—CO-thienyl-$QCOZ'R''$, —CO-imidazolyl-$QCOZ'R''$,
—CO-piperazino-$QCOZ'R''$,
—CO-piperidino-$QCOZ'R''$,
—$NR_{19}(CR_{13}R_{14})_t(CR_{15}R_{16})_u(OCH_2CH_2)_yCOZ'R''$,
—$NR_{19}CO(CR_{13}R_{14})_t(CR_{15}R_{16})_u(OCH_2CH_2)_yCOZ'R''$,
—$NR_{19}(CR_{13}R_{14})_t(CR_{17}=CR_{18})(CR_{15}R_{16})_u(OCH_2CH_2)_yCOZ'R''$,
—$NR_{19}CO(CR_{13}R_{14})_t(CR_{17}=CR_{18})(CR_{15}R_{16})_u(OCH_2CH_2)_yCOZ'R''$,
—$NR_{19}CONR_{12}(CR_{13}R_{14})_t(CR_{15}R_{16})_u(OCH_2CH_2)_yCOZ'R''$,
—$NR_{19}CONR_{12}(CR_{13}R_{14})_t(CR_{17}=CR_{18})(CR_{15}R_{16})_u(OCH_2CH_2)_yCOZ'R''$,
—$NR_{19}$CO-phenyl-$QCOZ'R''$, —$NR_{19}$CO-furyl-$QCOZ'R''$, —$NR_{19}$CO-oxazolyl-$QCOZ'R''$,
—$NR_{19}$CO-thiazolyl-$QCOZ'R''$, —$NR_{19}$CO-thienyl-$QCOZ'R''$, —$NR_{19}$CO-imidazolyl-$QCOZ'R''$,
—$NR_{19}$CO-morpholino-$QCOZ'R''$, —$NR_{19}$CO-piperazino-$QCOZ'R''$, —$NR_{19}$CO-piperidino-$QCOZ'R''$,
—$NR_{19}$-phenyl-$QCOZ'R''$, —$NR_{19}$-furyl-$QCOZ'R''$, —$NR_{19}$-oxazolyl-$QCOZ'R''$, —$NR_{19}$-thiazolyl-$QCOZ'R''$, —$NR_{19}$-thienyl-$QCOZ'R''$, —$NR_{19}$-imidazolyl-$QCOZ'R''$, —$NR_{19}$-piperazino-$QCOZ'R''$,
—$NR_{19}$-piperidino-$QCOZ'R''$, —NR$_{19}$CO—NR$_{12}$-phenyl-QCOZ'R", —NR$_{19}$CO—NR$_{12}$-oxazolyl-QCOZ'R", —NR$_{19}$CO—NR$_{12}$-thiazolyl-QCOZ'R", —NR$_{19}$CO—NR$_{12}$-thienyl-QCOZ'R", —NR$_{19}$CO—NR$_{12}$-piperidino-QCOZ'R",
—S(O)$_q$(CR$_{13}$R$_{14}$)$_t$(CR$_{15}$R$_{16}$)$_u$(OCH$_2$CH$_2$)$_y$COZ'R",
—S(O)$_q$(CR$_{13}$R$_{14}$)$_t$(CR$_{17}$=CR$_{18}$)(CR$_{15}$R$_{16}$)$_u$(OCH$_2$CH$_2$)$_y$COZ'R",
—SCONR$_{12}$(CR$_{13}$R$_{14}$)$_t$(CR$_{15}$R$_{16}$)$_u$(OCH$_2$CH$_2$)$_y$COZ'R",
—SCO-piperazino-QCOZ'R", and
—SCO-piperidino-QCOZ'R",
wherein:
Q is a direct link or a linear alkyl or branched alkyl having from 1-10 carbon atoms or a polyethylene glycol spacer with 2 to 20 repeating ethylene oxy units;
R$_{19}$ and R$_{12}$ are the same or different and are linear alkyl, branched alkyl or cyclic alkyl having from 1 to 10 carbon atoms, or simple or substituted aryl or heterocyclic, and R$_{12}$ can in addition be H;
R$_{13}$, R$_{14}$, R$_{15}$ and R$_{16}$ are the same or different and are H or a linear or branched alkyl having from 1 to 4 carbon atoms;
R$_{17}$ and R$_{18}$ are H or alkyl;
u is an integer from 1 to 10 and can also be 0;
t is an integer from 1 to 10 and can also be 0;
y is an integer from 1 to 20 and can also be 0.
The linker can be more particularly:
—(CR$_{13}$R$_{14}$)$_t$(CR$_{15}$R$_{16}$)$_u$(OCH$_2$CH$_2$)$_y$COZ'R";
—(CR$_{13}$R$_{14}$)$_t$(OCH$_2$CH$_2$)$_y$O(CR$_{15}$R$_{16}$)$_u$COZ'R";
—O(CR$_{13}$R$_{14}$)$_t$(CR$_{15}$R$_{16}$)$_u$(OCH$_2$CH$_2$)$_y$COZ'R";
—O(CR$_{13}$R$_{14}$)$_t$(NR$_{19}$CO)(CR$_{15}$R$_{16}$)$_u$(OCH$_2$CH$_2$)$_y$COZ'R";
—(C≡C)—(CR$_{13}$R$_{14}$)$_t$(CR$_{15}$R$_{16}$)$_u$(OCH$_2$CH$_2$)$_y$COZ'R".
or one of the following:
—O(CR$_{13}$R$_{14}$)$_t$COZ'R";
—(OCH$_2$CH$_2$)$_y$COZ'R";
—(C≡C)—(CR$_{13}$R$_{14}$)$_t$COZ'R";
—O(CR$_{13}$R$_{14}$)$_t$(NR$_{19}$CO)(CR$_{15}$R$_{16}$)$_u$COZ'R";
—(CR$_{13}$R$_{14}$)$_t$(OCH$_2$CH$_2$)$_y$COZ'R".
—Z'R" is more particularly —OH, —Oalkyl or

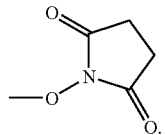

Suitable linkers and —Z'R" can be found in the examples enclosed herein. The particular

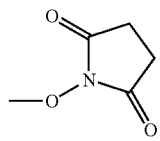

group tends to increase the reactivity of the ester function.
A subgroup of compounds comprises the following compounds:

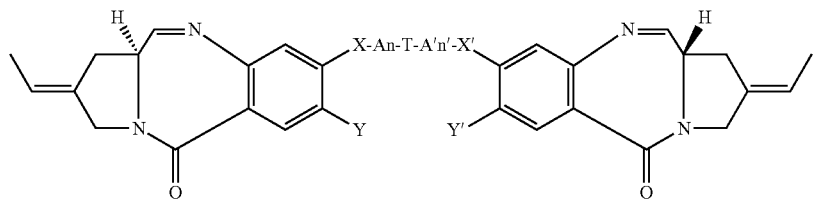

or

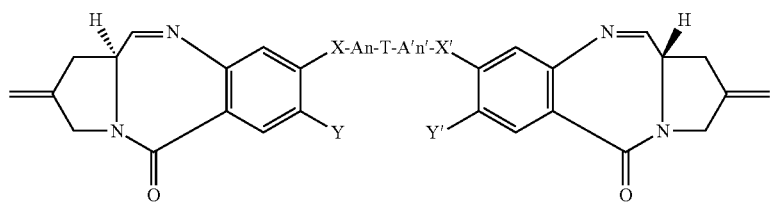

wherein X, X', A, A', Y, Y', T, n, n' are as defined above.

Another subgroup comprises the following compounds:

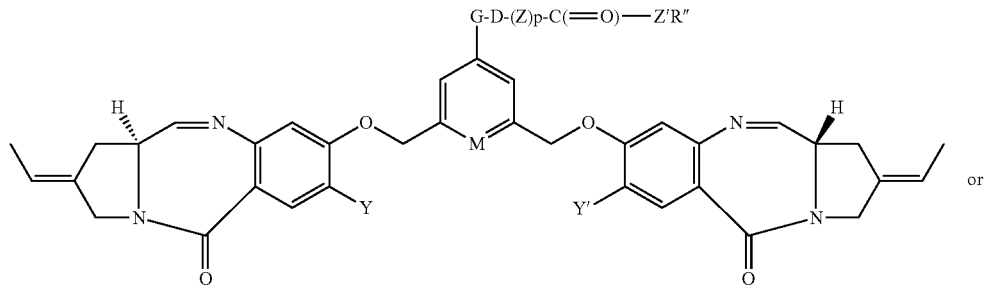

or

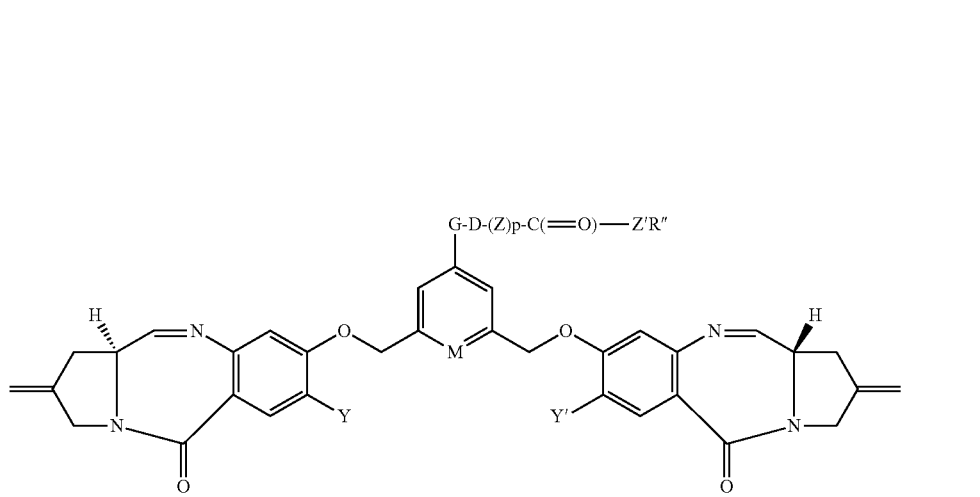

wherein Y, Y', G, D, Z, p, Z' and R" are as defined above and M represents CH or N. As mentioned above, the solubility of the tomaymicin derivative is improved in aqueous solutions when M is N.

According to another preferred aspect, compounds of the invention are selected from the group consisting of:

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid;

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid;

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid;

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid;

3-(2-{2-[2-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-ethoxy]-ethoxy}-ethoxy)-propionic acid;

4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid;

N-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethyl]-N-methyl-succinamic acid, 4-(3,5-Bis-[(S)-2-methylidene-7-methoxy-1,2,3,11a-tetrahydro-pyrrolo[2,1c][1,4]benzodiazepin-5-one-8-yloxymethyl]-phenyl)-propanoic acid;

(2-{2-[2-(2-{3-[3,5-Bis-(7-methoxy-2-methylene-5-oxo-2,3,5,11a-tetrahydro-1H-benzo[e]pyrrolo[1,2-a][1,4]diazepin-8-yloxymethyl)-phenyl]-propoxy}-ethoxy)ethoxy]-ethoxy}-ethoxy)-acetic acid;

(3-{2-[2-(2-{3-[3,5-Bis-(7-methoxy-2-methylene-5-oxo-2,3,5,11a-tetrahydro-1H-benzo[e]pyrrolo[1,2-a][1,4]diazepin-8-yloxymethyl)-phenyl]-propoxy}-ethoxy)ethoxy]-ethoxy}-ethoxy)-propanoic acid;

as well as the corresponding esters or N-hydroxysuccinimidyl esters, or their pharmaceutically acceptable salts, hydrates, or hydrated salts, or the polymorphic crystalline structures of these compounds or their optical isomers, racemates, diastereomers or enantiomers.

The geometrical isomers and stereoisomers of the compounds of general formula (I) or (I') are also part of the invention.

The N10, C11 double bond of the tomaymycin derivatives is known to be readily convertible in a reversible manner to corresponding imine adducts in the presence of water, an alcohol, a thiol, a primary or secondary amine, urea and other nucleophiles. This process is reversible and can easily regenerate the corresponding tomaymycin derivatives in the presence of a dehydrating agent, in a non-protic organic solvent, in vacuum or at high temperatures (Z. Tozuka, 36, *J. Antibiotics*, 276 (1983). Thus, this invention provides also for reversible derivatives of tomaymycin derivatives of general formula (II):

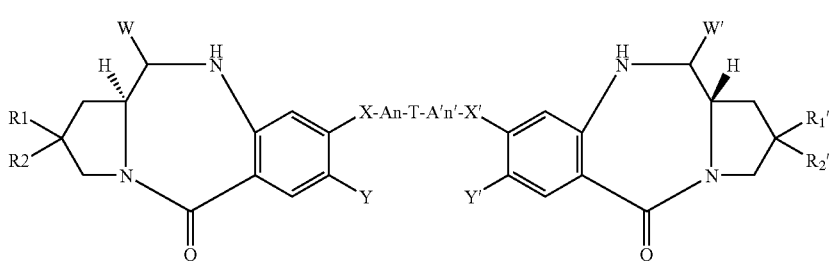

(II)

wherein A, X, Y, n, T, A', X', Y', n', R1, R2, R1', R2' are defined as in formula (I) or (I') and W, W' are the same or different and are selected from the group consisting of OH, an ether such as —OR, an ester (e.g. an acetate), such as —OCOR, —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO$_3^-$, a sulfonamide such as —NRSOOR', an amine such as —NRR', optionally cyclic amine such that N10 and C11 are a part of the cycle, a hydroxylamine derivative such as —NROR', an amide such as —NRCOR', —NRCONRR', an azido such as —N$_3$, a cyano, a halo, a trialkyl or triarylphosphonium, an aminoacid-derived group. Preferably, W and W' are the same or different and are OH, OMe, OEt, NHCONH$_2$, SMe. Compounds of formula (II) may thus be considered as solvates, including water when the solvent is water; these solvates can be particularly useful.

About the Preparation of the Compounds

The compounds can be synthesized by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Synthesis*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, the reaction can be carried out at a temperature of from −20° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

First Route:

According to a first route, the process of preparation of the compounds where T comprises a terminal carboxy group comprises the step of deprotecting the compounds of formula:

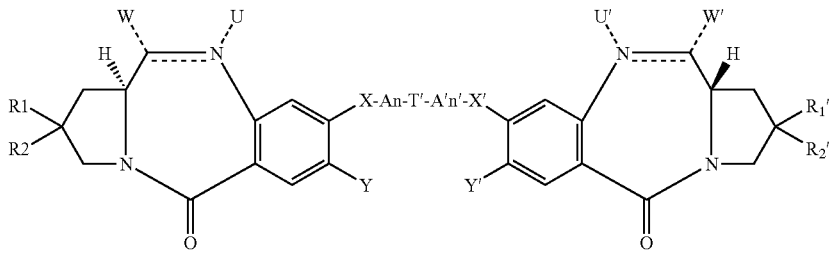

where Y, Y', X, A, A', X', n, n', W, W', U, U', -----, R1, R2, R1', R2', ----- are as defined above and T' corresponds to T where the terminal carboxy group is protected by the N-succinimide group or esterified.

A representative reaction of deprotection is the hydrolysis of a compound of formula (I) where T' corresponds to T where the terminal carboxy group is in the ester form. Said hydrolysis reaction is generally conducted in basic conditions, in the presence of an organic or mineral base, such as LiOH, followed by the addition of an organic or mineral acid, such as hydrochloride acid.

These compounds may be obtained by coupling corresponding compounds of formulae (IV), (IV') and (V):

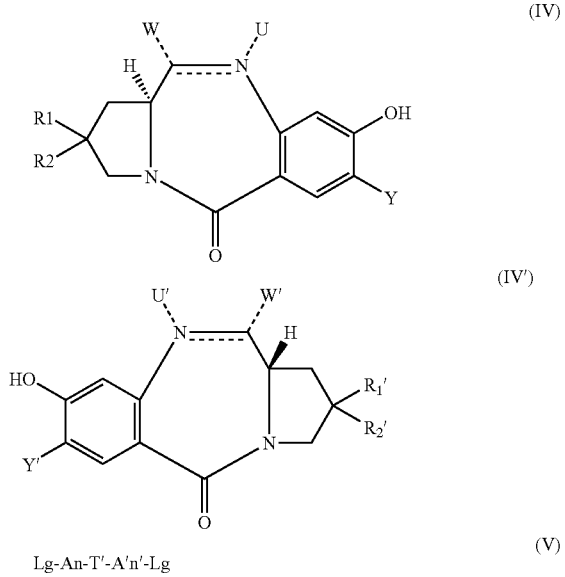

wherein Lg is a leaving group such as a halogen, —OMs (mesylate), —OTs (tosylate) or —OPPh$_3^+$ (intermediate formed in a Mitsunobu reaction).

The compounds of formula (IV) and (IV') are generally known, as disclosed for instance in WO 00/12608, WO 00/12507, WO 2005/040170, WO 2005/085260 or commercially available, and/or are available by total synthesis (M. Mori et al, 42 *Tetrahedron*, 3793-3806, 1986) or produced by *Streptomyces* species, in particular following French patent FR 1,516,743 procedure or may be prepared by application or adaptation of the illustrative procedures given in the examples.

The compounds of formula (V) may be obtained from corresponding compounds of formula HO-An-T'-A'n'-OH (VI). The reaction is generally carried out in the presence of PPh$_3$ and CHaI$_4$ or by reaction with a sulfonyl chloride (methanesulfonyl chloride or mesyl chloride) in the presence of a base such a triethylamine or potassium hydroxide, preferably triethylamine.

The compounds of formula (VI) may be obtained from corresponding compounds of formula HO-An-T''-A'n'-OH (VII) wherein T'' is a precursor group of T. A precursor group of T refers to any group which may lead to T by any deprotection, chemical modification, or coupling. Preferably, T is obtained by coupling T' with the complementary portion, where T' and the complementary portion comprise functions which are reactive to each other, eg. T' comprising a hydroxyl function and the complementary portion comprising a bromide function. A representative example for this reaction is described below:

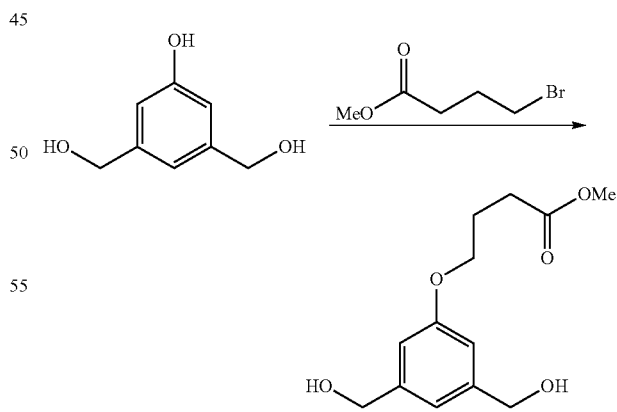

Generally, this reaction is carried out in the presence of potassium carbonate.

The compounds of formula (VII) may be commercially available or made by adaptation or application of known methods or according to the examples.

An exemplary non-limiting scheme for this route is given below:

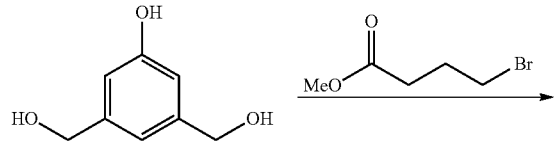

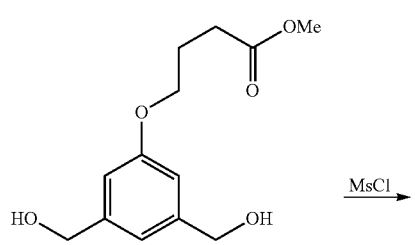

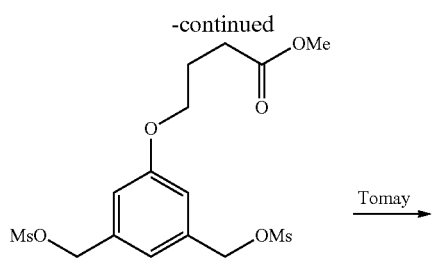

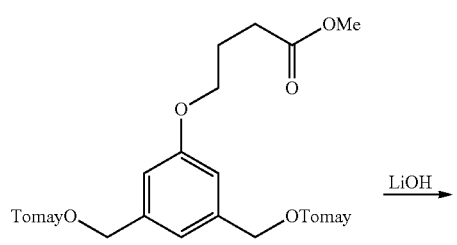

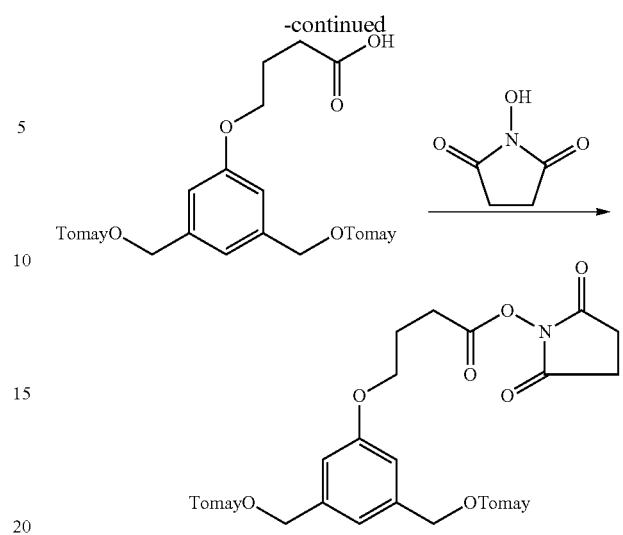

Second Route:

According to a second route, the compounds may be obtained from the corresponding compound of formula (III):

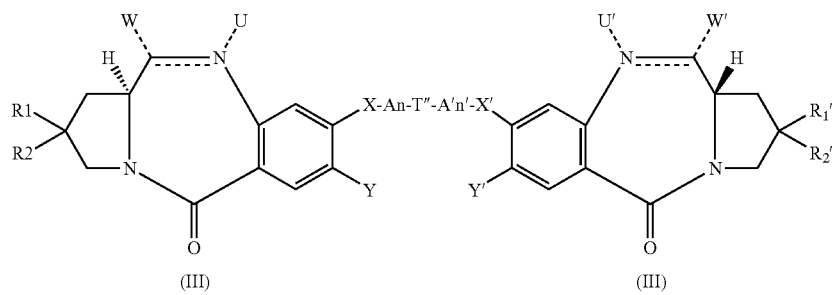

where Y, Y', X, A, A', X', n, n', W, W', U, U', ·····, ═══, R1, R2, R1', R2' are as defined above and T" is an optionally protected precursor group of T. A precursor group of T refers to any group which may lead to T by chemical modification, or coupling. Preferably, T is obtained by coupling T' with the corresponding complementary portion, where T' and the complementary portion comprise functions which are reactive to each other, eg. T' comprising an amine function and the complementary portion comprising an acid function. Generally, this reaction is carried out in the presence of N-hydroxysuccinimide and HOBT (N-Hydroxybenzotriazole).

The compound of formula (III) may be obtained from coupling the corresponding compounds of formulae (IV), (IV') and (V'):

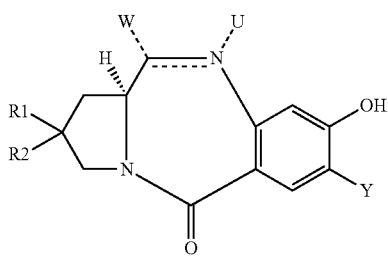

(IV)

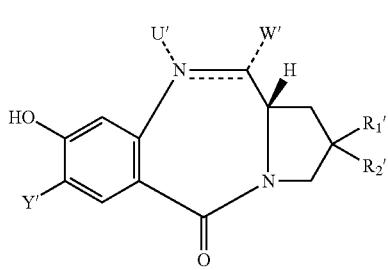

(IV')

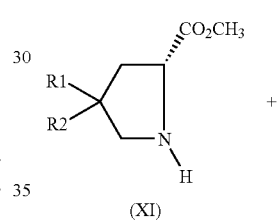

(V')

wherein Lg is a leaving group, such as halogen or —OMs, —OTs or —OPPh₃⁺ (intermediate formed in a Mitsunobu reaction).

The compounds of formula (V') may be obtained from corresponding compounds of formula HO-An-T'''-A'n'-OH (VII) wherein T'' is an optionally protected precursor group of T'. This reaction is generally carried out in the presence of PPh₃ and CHaI₄ or by mesylation of the hydroxy functions. The compounds of formula (VII) may be commercially available or made by adaptation or application of known methods or according to the examples.

Third Route:

According to a third route, the compounds having a symetric structure (R1=R1', R2=R'2 and Y=Y') can be prepared by cyclizing the corresponding compounds of formula (VIII):

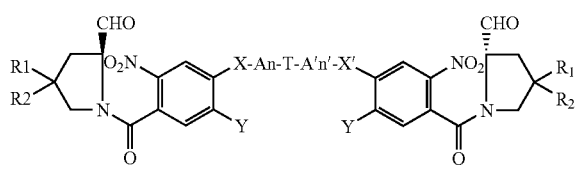

(VIII)

where Y, X, X', A, A', n, n', R1, R2, T are as defined above. Generally, this reaction is carried out in the presence of a reagent such as sodium hydrosulfite (Na₂S₂O₄), in an appropriate solvent such as a mixture THF/water, followed by addition of MeOH and AcCl.

The compounds of formula (VIII) may be obtained from the corresponding compounds of formula (IX):

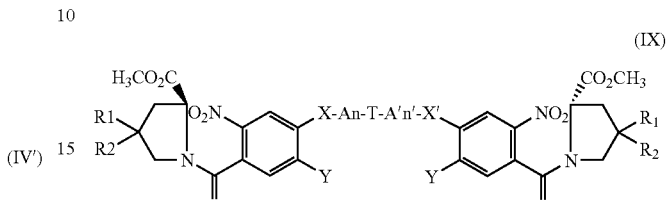

(IX)

This reaction is carried out in the presence of a reagent such as diisobutylaluminium hydride (DIBAL-H) in an appropriate solvent, such as toluene. The compounds of formula (IX) may be obtained from coupling the corresponding compounds of formula (X) and (XI):

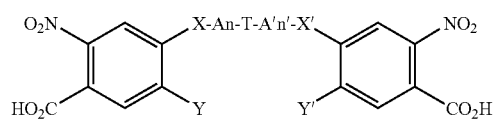

(XI)

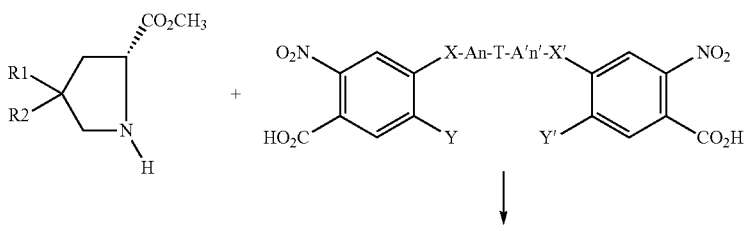

(X)

Generally, this reaction is carried out by adding to (X) a reagent such as oxalyl chloride in an appropriate solvent, such as DMF, followed by adding (XI) in an appropriate solvent, such as THF.

An exemplary non-limiting scheme for this route is given below:

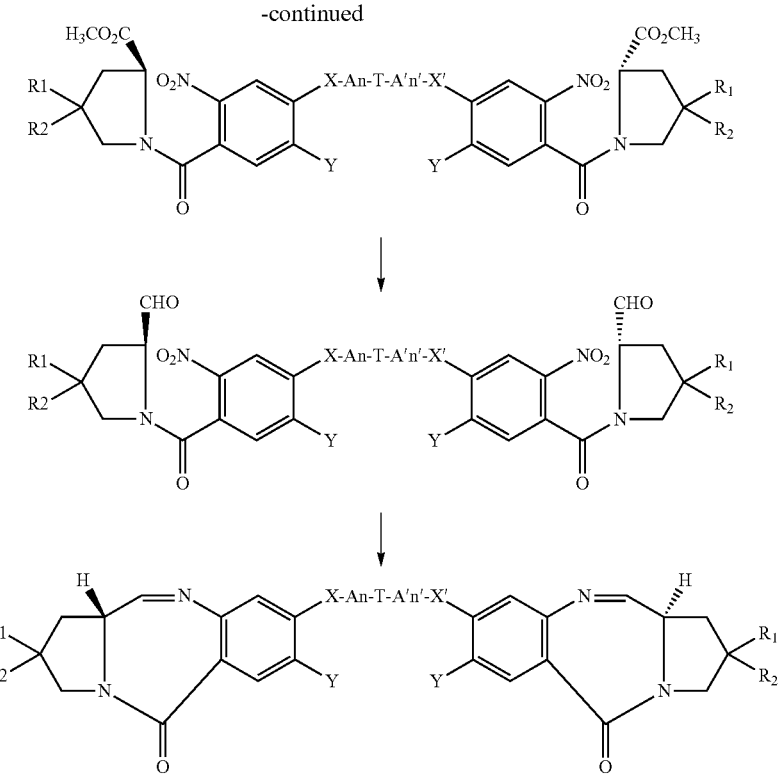

The above reactions can be carried out by the skilled person by applying or adapting the methods illustrated in the examples hereinafter. Further, the processes described herein may comprise the additional step(s) of isolating any final or intermediate products. This can be done by the skilled person by any of the known conventional means, such as the recovery methods described above. The starting products are commercially available or may be obtained by applying or adapting any known methods or those described in the examples. The synthesis may also be carried out in one pot as a multicomponent reaction.

About the Conjugate Molecule:

The present invention also concerns a conjugate molecule comprising at least one tomaymycin derivative chemically linked to a cell binding agent through the linking group of the linker. The chemical link is preferably a covalent bond. Said conjugate comprises one or more tomaymycin derivative according to the invention covalently linked to the cell binding agent through the linking group of the linker of the tomaymycin derivative. As a representative example, said conjugate comprises a tomaymycin derivative of the invention covalently linked to the cell binding agent through the terminal —CO—Z'R" group of the linker. Said linking group covalently links the cell binding agent with the linker of the tomaymycin derivative.

Preferably, the linker is linked to the cell binding agent via a function reactive towards for instance thiol and amino functions of the cell binding agent coming from reduced disulfide bonds and lysine residues respectively. More particularly, said derivative is linked through the —CO— group to the amino function of the lysine residue of said cell binding agent, so as to form an amide bond.

Cell binding agents may be of any kind and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance. More specific examples of cell binding agents that can be used include: monoclonal antibodies; chimeric antibodies; humanized antibodies; fully human antibodies; single chain antibodies; fragments of antibodies such as Fab, Fab', F(ab')$_2$ and F$_v$ {Parham, 131 *J. Immunol.* 2895-2902 (1983); Spring et al, 113 *J. Immunol.* 470-478 (1974); Nisonoff et al, 89 *Arch. Biochem. Biophys.* 230-244 (1960)}; interferons; peptides; lymphokines such as IL-2, IL-3, IL-4, IL-6; hormones such as insulin, TRH (thyrotropin releasing hormones), MSH (melanocyte-stimulating hormone), steroid hormones, such as androgens and estrogens; growth factors and colony-stimulating factors such as EGF, TGFα, insulin like growth factor (IGF-I, IGF-II) G-CSF, M-CSF and GM-CSF {Burgess, 5 *Immunology Today* 155-158 (1984)}; vitamins, such as folate and transferrin {O'Keefe et al, 260 *J. Biol. Chem.* 932-937 (1985)}.

The expression "cell binding agent" also includes modified cell binding agents, wherein said cell binding agent is modified by a modifying agent to improve the reactivity of said cell binding agent towards the linking group of the linker of the tomaymycin derivative.

Monoclonal antibody technology permits the production of extremely selective cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available. For example, the monoclonal antibody MY9 is a murine $IgG_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine $IgG_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia. As stated above, the MY9 and anti-B4 antibodies may be murine, chimeric, humanized or fully human.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

Examples of suitable monoclonal antibodies that can be used to prepare the conjugate molecule can be hu2H11 (registered under PTA-7662 by ATCC), one of the huMy9-6 described in WO 2004/043344, huDS6 described in WO 2005/009369 or one described in WO 2008/047242, WO 2005/061541 or WO 02/16101.

The tomaymycin derivatives may be linked to an antibody or other cell binding agent via an amide type function. Preferably, the derivatives are synthesized to contain a carboxylic function, and then one or more carboxylic acid-containing derivatives are each covalently linked to the cell binding agent via an amide link.

Representative conjugates of the invention are antibody-tomaymycin derivative, antibody fragment-tomaymycin derivative epidermal growth factor (EGF)-tomaymycin derivative, melanocyte stimulating hormone (MSH)-tomaymycin derivative, thyroid stimulating hormone (TSH)-tomaymycin derivative, estrogen-tomaymycin derivative, estrogen analogue-tomaymycin derivative, androgen-tomaymycin derivative, androgen analogue-tomaymycin derivative, and folate-tomaymycin derivative. The conjugates can be purified by HPLC or by gel filtration.

Preferably, monoclonal antibody- or cell binding agent-tomaymycin derivative conjugates are those that are joined via an amide bond, as discussed above, that are capable of delivering tomaymycin derivatives. Conjugates can be prepared using N-hydroxysuccinimide derivatives of the carboxylic function at the terminal of the tomaymycin dimer linker. Conjugates containing 1 to 10 tomaymycin derivative drugs linked via an amide link are readily prepared by this method.

More specifically, a solution of antibody at a concentration of 8 mg/ml in a an aqueous buffer containing 0.05 M potassium phosphate, 0.05 M sodium chloride and 2 mM ethylenediaminetetra-acetic acid (EDTA), at pH 8 is treated with a 5 fold molar excess of a solution of the N-hydroxysuccinimide derivative of a tomaymycin dimer in dimethylacetamide (DMA) such that the final concentration of DMA in the buffer is 20%. The reaction mixture is stirred for 70 min at room temperature (rt). The antibody-tomaymycin derivative conjugate is purified and freed of unreacted drug and other low molecular weight material by gel filtration through a column of Sephadex G-25 or Sephacryl S300 or Superdex 200. The sample can also be dialyzed overnight in a pH 6.5 buffer to further purify the product. The number of tomaymycin derivative moieties bound per antibody molecule can be determined by measuring the ratio of the absorbance at 320 nm and 280 nm. An average of 1-10 tomaymycin derivative molecules/antibody molecule can be linked via an amide bond by this method.

The effect of conjugation on binding affinity towards the antigen-expressing cells can be determined using the methods previously described by Liu et al., 93 Proc. Natl. Acad. Sci 8618-8623 (1996). Cytotoxicity of the tomaymycin derivatives and their antibody conjugates to cell lines can be measured by back-extrapolation of cell proliferation curves as described in Goldmacher et al, 135 J. Immunol. 3648-3651 (1985). Cytotoxicity of these compounds to adherent cell lines can be determined by clonogenic assays as described in Goldmacher et al, 102 J. Cell Biol. 1312-1319 (1986).

Representative conjugates of the invention are conjugates of tomaymycin derivatives with antibodies, antibody fragments, epidermal growth factor (EGF), melanocyte stimulating hormone (MSH), thyroid stimulating hormone (TSH), estrogen, estrogen analogs, androgen, and androgen analogs.

Representative examples of the preparation of various conjugates of derivatives and cell binding agents are described below.

Amide linkers: For example, the monoclonal antibody MY9 is a murine $IgG_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine $IgG_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

The antibody or other cell binding agent is reacted with the N-hydroxy-succinimide acid derivative to produce an amide-linked conjugate.

The conjugates made by the above methods can be purified by standard chromatography techniques such as size-exclusion, adsorption chromatography including, but not limited to, ion exchange, hydrophobic interaction chromatography, affinity chromatography, chromatography on ceramic hydroxyapatite or on Porapak, or by HPLC. Purification by dialysis or diafiltration may also be used.

Preferably, conjugates between monoclonal antibodies or cell binding agents and derivatives of the present invention are those that are joined via an amide bond, as discussed above. Such cell binding conjugates are prepared by known methods such as modifying the linkable drug molecules possessing a carboxylic function to get the N-hydroxy-succinimide acid derivative. The resulting activated carboxylic groups then acylate the containing lysine residues of the antibody to produce amide linked conjugates. Conjugates containing 1 to 10 derivatives linked via an amide bridge are readily prepared by this method.

According to a preferred aspect, the cell binding agent is an antibody, in particular a monoclonal antibody. According to another preferred aspect, the cell binding agent is an antigen specific antibody fragment, such as sFV, Fab, Fab' or F(ab')$_2$.

About the Use of the Conjugate Molecule:

The present invention also concerns the pharmaceutical compositions comprising a conjugate molecule of the invention or a tomaymycin derivative as defined above together with a pharmaceutically acceptable carrier.

The present invention also concerns a method of killing or inhibiting growth of cells, preferably selected cell populations comprising contacting target cells or tissue containing target cells with an effective amount of the pharmaceutical composition. The selected cell populations are those cancerous and/or proliferative cells. The present invention also concerns a method for treatment, preferably selective treatment, of cancer comprising administering an effective amount of the pharmaceutical composition to a patient in need thereof. "Selective treatment of cancer" refers to killing cancerous and/or proliverative cells substantially without killing normal and/or non-proliferative cells.

The present invention also concerns the use of a conjugate molecule or a tomaymycin derivative as defined above for the preparation of a medicament for treating cancer.

The method for inhibiting the growth of selected cell populations can be practiced in vitro, in vivo, or ex vivo. Examples of in vitro uses include treatments of cell cultures in order to kill all cells except for desired variants that do not express the target antigen; or to kill variants that express undesired antigen. The conditions of non-clinical in vitro use are readily determined by the skilled artisan. Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD). Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment. For clinical in vivo use, the cytotoxic agent of the invention will be supplied as solutions that are tested for sterility and for endotoxin levels or as a lyophilized solid that can be redissolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 µg to 10 mg/kg of body weight per week, i.v. (range of 10 µg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; bacterial infection; and parasite infections, such as giardiasis, amoebiasis, schistosomiasis, and others as determined by one skilled in the art.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, intraperitoneal, sub-cutaneous or other), the pharmacokinetic properties of the compound by the chosen delivery route, and the speed (bolus or continuous infusion) and schedule of administrations (number of repetitions in a given period of time).

The compositions may conveniently be administered in unit dosage form and may be prepared by any of the methods well known in the pharmaceutical art, for example, as described in Remington: The Science and Practice of Pharmacy, 20$^{th}$ ed.; Gennaro, A. R., Ed.; Lippincott Williams & Wilkins: Philadelphia, Pa., 2000.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Experimental Part

Method A1: High Pressure Liquid Chromatography-Mass Spectrometry (LCMS)

A Micromass MassLynx software is used and the analysis is performed on a Waters Alliance HPLC with a WATERS XBridge C18 3.5 µm column (100×3 mm) using gradient elution with a mixture of (A) methanol and (B) water/0.1% formic acid (gradient: 5% A: 95% B up to 95% A: 5% B over 10 min, 95% A: 5% B down to 5% A: 95% B over 1 min, 5% A: 95% B for 2 min) with a 1.1 mL/min flow rate; Waters-Micromass Platform II spectrometer with Electrospray (positive and negative ionisation); in line Diode Array (190-500 nm); auxiliary detector Sedere (France) Model SEDEX 85 Evaporative Light Scattering (ELS) detector.

Method A2: High Pressure Liquid Chromatography-Mass Spectrometry (LCMS)

A Micromass MassLynx software is used and the analysis is performed on a Agilent 1100 series HPLC with a XBridge C18 2.5 µm column (50×3 mm) using gradient elution with a mixture of (A) acetonitrile and (B) water/0.1% formic acid (gradient: 5% A: 95% B up to 100% A over 5 minutes, 100% A for 0.5 min, 100% A down to 5% A: 95% B over 1 min, 5% A: 95% B for 0.5 min) with a 1.1 mL/min flow rate; Waters-Micromass ZQ spectrometer with Electrospray (positive and negative ionisation); in line Diode Array (210-254 nm).

Method A3: High Pressure Liquid Chromatography-Mass Spectrometry (LCMS)

The analysis is performed on a Waters UPLC-SQD with a ACQUITY BEH $C_{18}$ 1.7 µm-2.1×50 mm column at 50° C., using gradient elution with a mixture of (A) $H_2O$/0.1% formic acid and (B) $CH_3CN$/0.1% formic acid (gradient: 95% A: 5% B down to 50% A: 50% B over 0.8 min, 50% A: 50% B down to 100% B over 1.2 min, 100% B for 1.85 min, 100% B up to 95% A: 5% B over 1.95 min) with a 1 mL/min flow rate; Electrospray (positive and/or negative ionisation).

Method A4: High Pressure Liquid Chromatography-Mass Spectrometry (LCMS)

The analysis is performed on a Waters ZQ spectrometer with a XBridge C18 2.5 µm column (50×3 mm) at 70° C. using gradient elution with a mixture of (A) acetonitrile and (B) water/0.1% formic acid (gradient: 5% A: 95% B up to 100% A over 5.3 min, 100% A for 5.5 mn, 5% A: 95% B for 6.3 mn) with a 0.9 mL/min flow rate; Electrospray (positive and/or negative ionisation).

Method B: $^1$H Nuclear Magnetic Resonance (NMR) Spectra $^1$H NMR spectra were recorded on either a BRUKER AVANCE DRX-500, a BRUKER AVANCE DRX-400 spectrometer or a BRUKER AVANCE DRX-300 spectrometer. Reported $^{13}$C NMR spectra were recorded on a BRUKER AVANCE DRX-300 spectrometer.

Method C: Chemical Ionisation (CI) Mass Spectra

CI mass spectra were recorded using a WATERS GCT of mass spectrometer (ammonia).

Method D: Chemical Ionisation (CI) mass spectra; CI mass spectra were recorded using a FINNIGAN SSQ 7000 mass spectrometer (ammonia).

Example 1

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester may be Prepared as Follows

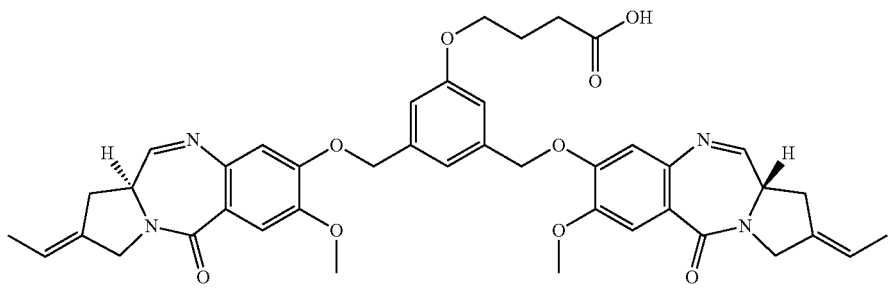

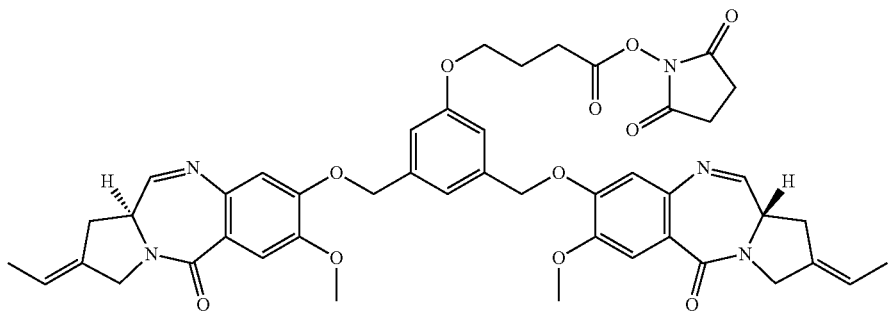

To a suspension of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid (11.3 mg) in tetrahydrofuran (0.4 mL) were added N,N'-disuccinimidyl carbonate (7.7 mg) and N,N-diisopropylethylamine (15.8 µL). After 2.5 h at rt, ethyl acetate (6 mL) was added to the reaction mixture and the organic solution was washed twice with water (4 mL) then with a saturated sodium chloride aqueous solution (5 mL), dried over magnesium sulfate and concentrated in vacuo to a residue. The residue was purified by silica gel chromatography (Merck MiniVarioFlash 2.5 g column, Si60 15-40 µm), using gradient elution with a mixture of MeOH (methanol) (A)/DCM (dichloromethane) (B), (gradient: 2% A: 98% B up to 4% A: 96% B) to give 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester (17.6 mg): LC/MS (Method A4): ES: m/z 846 (M+H)$^+$; Retention time (RT)=3.89 min; 1H NMR (400 MHz, CDCl$_3$-d1, δ ppm): δ=1.75 (d, J=6.8 Hz, 6H); 2.23 (m, 2H); 2.73-2.87 (m, 6H); 2.97 (m, 4H); 3.84-3.95 (m, 2H); 3.97 (s, 6H); 4.06 (m, 2H); 4.26 (m, 4H); 5.14 (d, J=12.4 Hz, 2H); 5.21 (d, J=12.4 Hz, 2H); 5.62 (m, 2H); 6.84 (s, 2H); 6.96 (s, 2H); 7.09 (s, 1H); 7.53 (s, 2H); 7.63 (m, 2H).

4-(3,5-Bis-[(S)-2-eth-(E)-ylidene-7-methoxy-1,2,3, 11a-tetrahydro-pyrrolo[2,1c][1,4]benzodiazepin-5-one-8-yloxymethyl]-phenoxy)-butyric acid may be Prepared as Follows

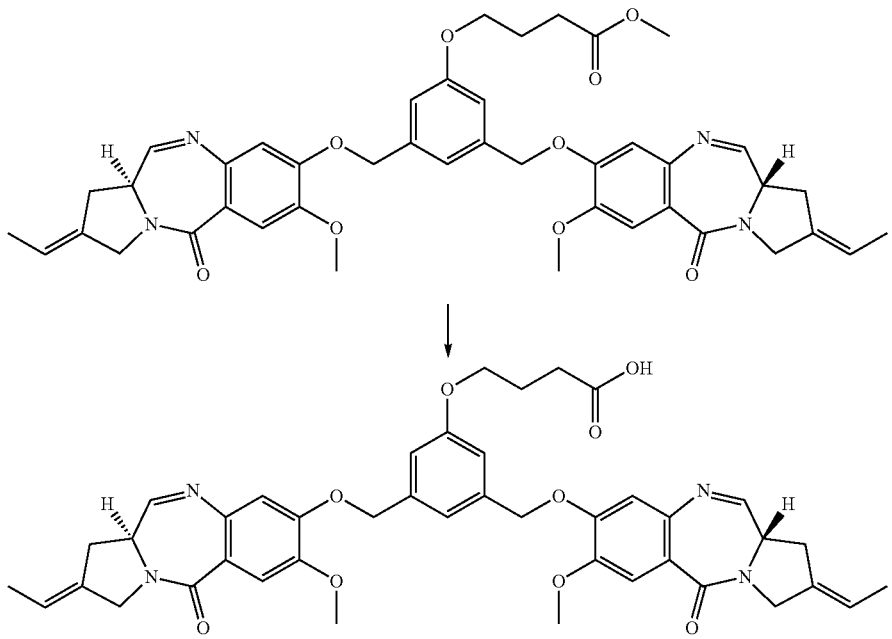

To a solution of 4-(3,5-bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester (60 mg) in tetrahydrofuran (0.9 mL) were added MeOH (0.3 mL), water (0.3 mL) and an aqueous solution of lithium hydroxide (1M, 87 µL). After 3 hours, the reaction mixture was diluted with water (10 mL), and pH was adjusted to 2 by adding an aqueous solution of chlorhydric acid 1N. The aqueous phase was extracted three times with DCM (10 mL), and the combined organic solutions were dried over sodium sulfate, and concentrated in vacuo to a residue. The residue was purified by silica gel chromatography (Merck SuperVarioFlash 10 g column, SiOH 15-40 µm), eluted with a mixture of DCM/MeOH/acetic acid (100:4:0.5) to give 4-(3,5-bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid: LC/MS (Method A2): ES: m/z=749 MH+; m/z=375 (M+2H)$^{2+}$/2; RT=3.7 min; $^1$H N.M.R. (400 MHz, DMSO-d6, δ in ppm): δ=1.69 (d, J=6.5 Hz, 6H); 1.95 (m, 2H); 2.39 (t, J=6.5 Hz, 2H); 2.91 (m, 2H); 3.05 (m, 2H); 3.83 (s, 6H); 3.98 (m, 2H); 4.01 (t, J=6.5 Hz, 2H); 4.10 (m, 4H); 5.11 (d, J=12.5 Hz, 2H); 5.20 (d, J=12.5 Hz, 2H); 5.55 (m, 2H); from 6.90 to 7.15 (m, 5H); 7.34 (s, 2H); 7.77 (m, 2H); 12.1 (m broad, 1H).

4-(3,5-Bis-[(S)-2-eth-(E)-ylidene-7-methoxy-1,2,3, 11a-tetrahydro-pyrrolo[2,1c][1,4]benzodiazepin-5-one-8-yloxymethyl]-phenoxy)-butyric acid methyl ester may be Prepared as Follows

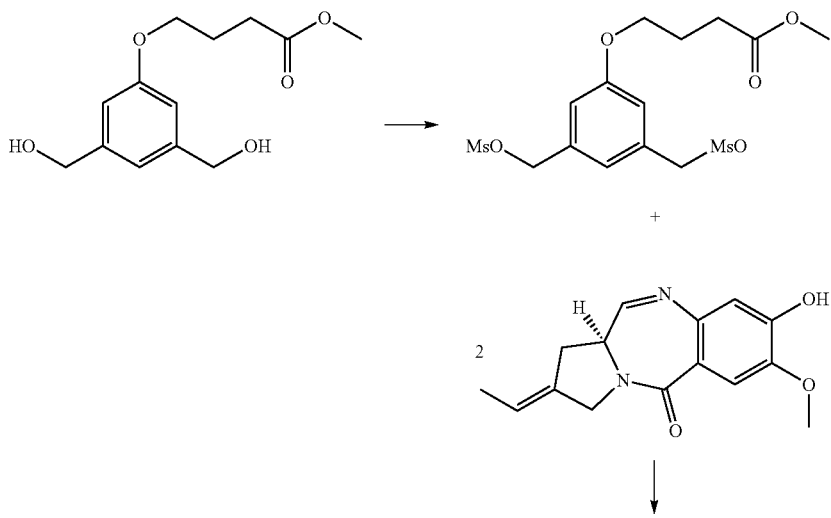

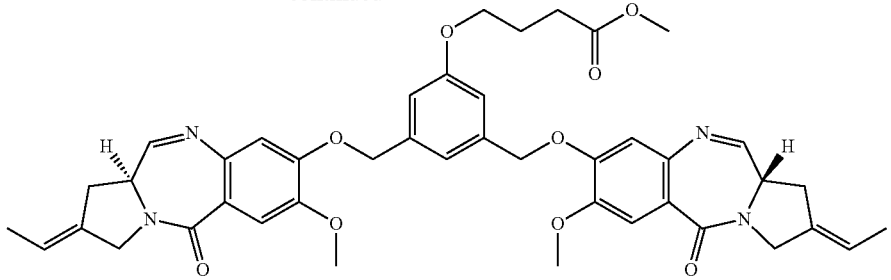

To a cooled (0° C.) solution of 4-(3,5-bis-hydroxymethyl-phenoxy)-butyric acid methyl ester (50 mg) and triethylamine (110 μL) in THF (tetrahydrofuran) (1.4 mL), was added methanesulfonyl chloride (46 μL). After 1 h, the reaction mixture was diluted with DCM (10 mL) and washed twice with water (5 mL). The organic solution was dried over sodium sulfate, and concentrated in vacuo to a residue. The residue was purified by silica gel chromatography (Merck SuperVarioFlash 10 g column, SiOH 15-40 μm), using gradient elution with a mixture of MeOH (A)/DCM (B), (gradient: 100% B down to 5% A: 95% B) to give 71.8 mg of di-mesylate compound. To a mixture of tomaymycine (80 mg), potassium iodide (49 mg), potassium carbonate (122 mg) in DMF (dimethylformamide) (1 mL), was added a solution of the di-mesylate compound (71.8 mg) in DMF (1.6 mL). The reaction mixture was stirred for 16 h at 30° C. Water (12 mL) was added and the resulting solid was filtered, washed with water and dried in vacuo to give a residue. The residue was purified by silica gel chromatography (Merck SuperVarioFlash 30 g column, SiOH 15-40 μm), using gradient elution with a mixture of MeOH (A)/DCM (B), (gradient: 100% B down to 5% A: 95% B) to give 4-(3,5-bis-[(S)-2-eth-(E)-ylidene-7-methoxy-1,2,3,11a-tetrahydro-pyrrolo[2,1c][1,4]-benzodiazepine-5-one-8-yloxymethyl]-phenoxy)-butyric acid methyl ester (65.4 mg): LC/MS (Method A2): ES: m/z=763 MH$^+$; m/z=382 (M+2H)$^{2+}$/2; RT=4.0 min; $^1$H N.M.R. (500 MHz, CDCl$_3$-d1, δ in ppm): 1.75 (d, J=6.5 Hz, 6H); 2.11 (m, 2H); 2.53 (t, J=6.5 Hz, 2H); 2.98 (m, 4H); 3.69 (s, 3H); 3.89 (m, 2H); 3.97 (s, 6H); 4.00 (t, J=6.5 Hz, 2H); 4.28 (s broad, 4H); 5.12 (d, J=12.5 Hz, 2H); 5.19 (d, J=12.5 Hz, 2H); 5.61 (m, 2H); 6.82 (s, 2H); 6.92 (s, 2H); 7.06 (s, 1H); 7.52 (s, 2H); 7.64 (d, J=4.5 Hz, 2H).

4-(3,5-Bis-hydroxymethyl-phenoxy)-butyric acid methyl ester may be Prepared as Follows

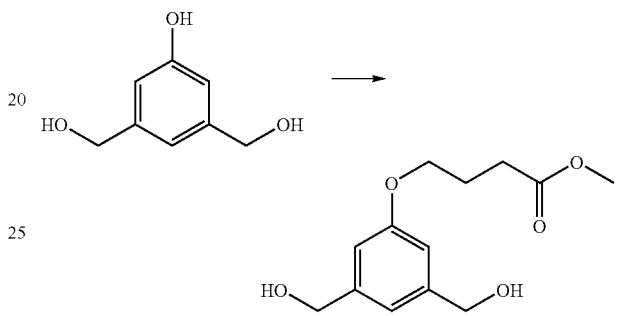

To a solution of 3,5-bis-hydroxymethylphenol (Felder, D.; Gutiérrez Nava, M.; del Pilar Carreon, M.; Eckert, J. F.; Luccisano, M.; Schell, C.; Masson, P.; Gallani, J. L.; Heinrich, B.; Guillon, D.; Nierengarten, J. F. Helv. Chimica Acta 2002, 85, 288) (200 mg), potassium iodide (50 mg) and potassium carbonate (540 mg) in THF (2.5 mL) was added 4-bromo-butyric acid methyl ester (400 μL). The reaction mixture was stirred for 20 h at room temperature then the unsoluble part was filtered off. The filtrate was concentrated in vacuo and the residue was purified by silica gel chromatography (Merck SuperVarioFlash 30 g column, Si60 15-40 μm), using gradient elution with a mixture of MeOH (A)/DMC (B), (gradient: 100% B down to 5% A: 95% B) to give 4-(3,5-bis-hydroxymethyl-phenoxy)-butyric acid methyl ester (53.5 mg): LC/MS (Method A2: ES: m/z=255 MH$^+$; m/z=237 (M+H–H$_2$O)$^+$; RT=2.5 min; $^1$H N.M.R. (400 MHz, DMSO-d6, δ in ppm): δ=1.96 (m, 2H); 2.47 (t, J=6.5 Hz, 2H); 3.61 (s, 3H); 3.96 (t, J=6.5 Hz, 2H); 4.43 (d, J=6.0 Hz, 4H); 5.11 (t, J=6.0 Hz, 2H); 6.71 (s, 2H); 6.82 (s, 1H).

Example 2

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid

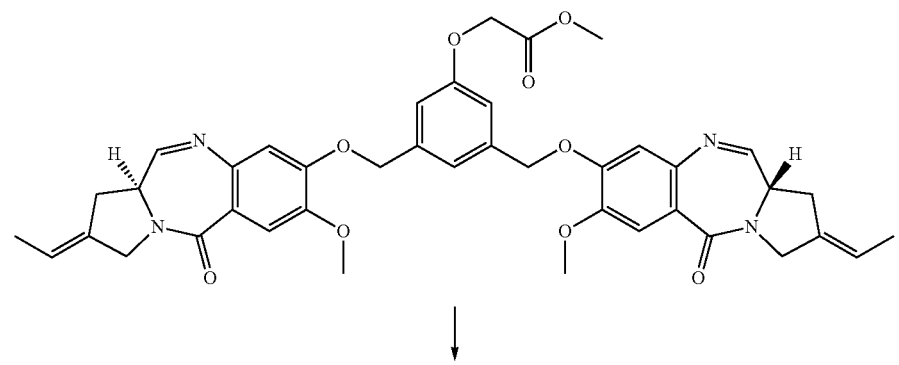

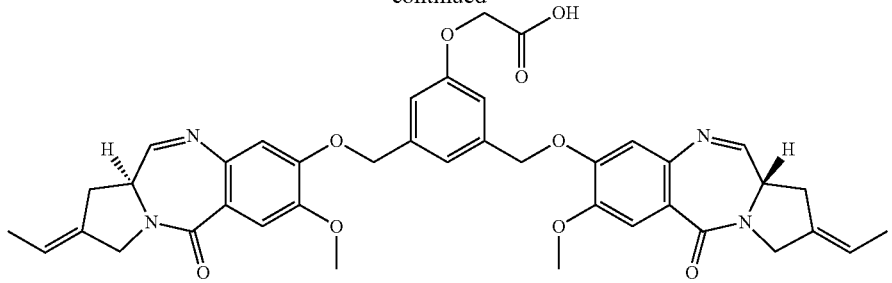

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid may be prepared following the procedure for the preparation of 4-(3,5-bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid, starting with 4-(3,5-bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid methyl ester:

LC/MS (Method A2): ES: m/z=721 MH$^+$; m/z=361 (M+2H)$^{2+}$/2; RT=3.5 min 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid methyl ester

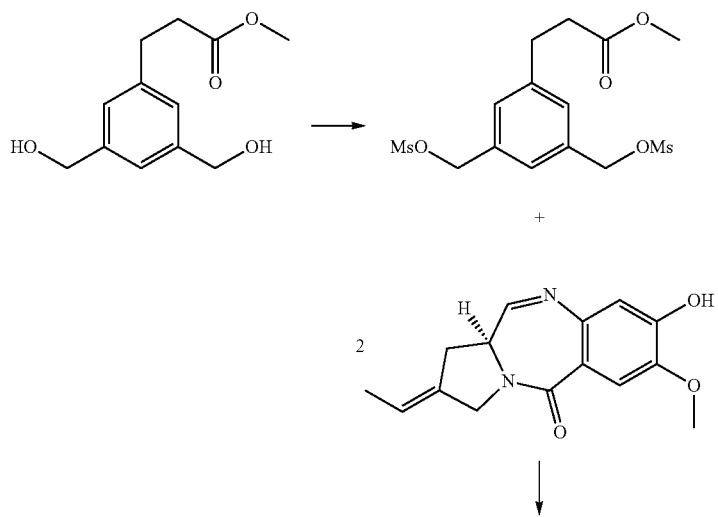

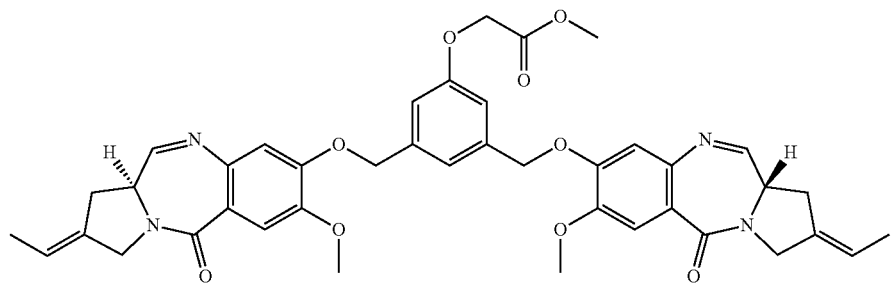

4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid methyl ester may be prepared following the procedure for the preparation of 4-(3,5-bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with 4-(3,5-bis-hydroxymethyl-phenoxy)-acetic acid methyl ester: LC/MS (Method A2): ES: m/z=735 MH$^+$; m/z=368 (M+2H)$^{2+}$/2; RT=3.8 min; $^1$H N.M.R. (500 MHz, CDCl$_3$-d1, δ in ppm): δ=1.76 (d, J=6.5 Hz, 6H); 2.96 (m, 4H); 3.78 (s, 3H); 3.88 (m, 2H); 3.97 (s, 6H); 4.27 (s broad, 4H); 4.64 (s, 2H); 5.13 (d, J=12.5 Hz, 2H); 5.19 (d, J=12.5 Hz, 2H); 5.60 (m, 2H); 6.80 (s, 2H); 6.96 (s, 2H); 7.11 (s, 1H); 7.53 (s, 2H); 7.63 (d, J=4.5 Hz, 2H).

4-(3,5-Bis-hydroxymethyl-phenoxy)-acetic acid methyl ester

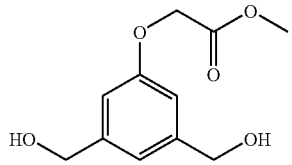

4-(3,5-Bis-hydroxymethyl-phenoxy)-acetic acid methyl ester may be prepared following the procedure for the preparation of 4-(3,5-bis-hydroxymethyl-phenoxy)-butyric acid methyl ester, starting with 4-bromo-acetic acid methyl ester: LC/MS (Method A2): ES: m/z=227 MH$^+$; m/z=209 (M+H−H$_2$O)$^+$; RT=1.9 min; $^1$H N.M.R. (400 MHz, DMSO-d6, δ in ppm): δ=3.70 (s, 3H); 4.43 (d, J=6.0 Hz, 4H); 4.74 (s, 2H); 5.14 (t, J=6.0 Hz, 2H); 6.72 (s, 2H); 6.88 (s, 1H).

Example 3

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid N-hydroxysuccinimidyl ester

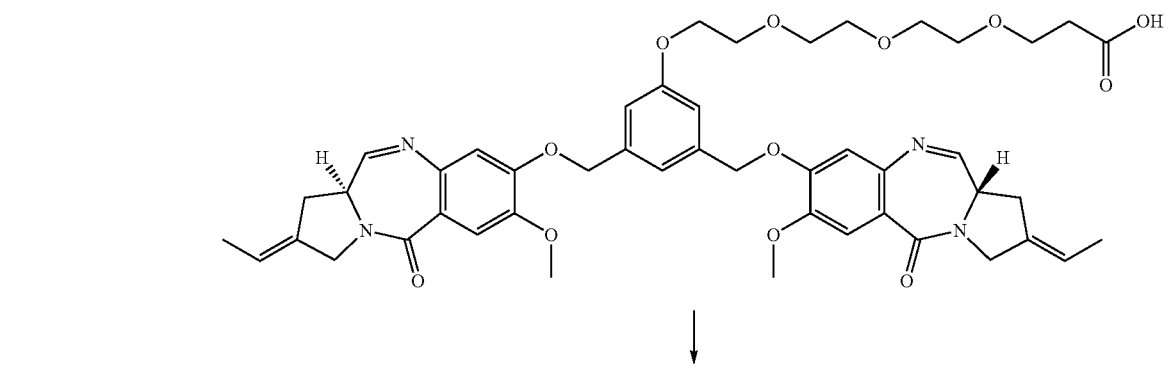

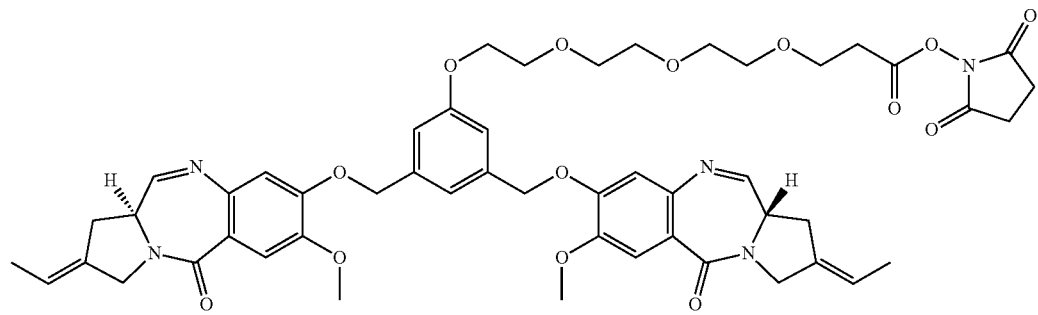

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid N-hydroxysuccinimidyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxy methyl]-phenoxy)-butyric acid N-hydroxysuccinimidyl ester, starting with 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid: LC/MS (Method A3): ES: m/z 964 (M+H)⁺;

RT=0.90 min; ¹H NMR (500 MHz, CDCl₃-d1, δ ppm): δ=1.75 (dd, J=6.7 Hz, 6H); 2.82 (m, 4H); 2.89 (t, J=6.6 Hz, 2H); 2.97 (m, 4H); 3.57-4.23 (m, 16H); 3.97 (s, 6H); 4.27 (m, 4H); 5.13 (d, J=12.7 Hz, 2H); 5.20 (d, J=12.2 Hz, 2H); 5.61 (m, 2H); 6.82 (s, 2H); 6.96 (s, 2H); 7.07 (s, 1H); 7.53 (s, 2H); 7.64 (d, J=4.4 Hz, 2H).

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid

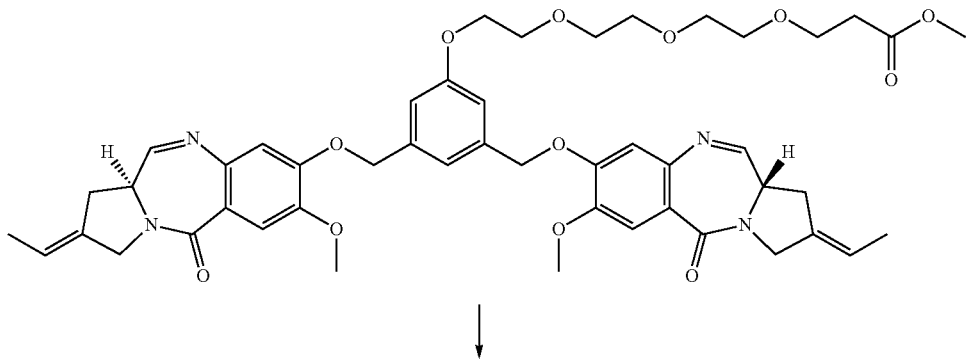

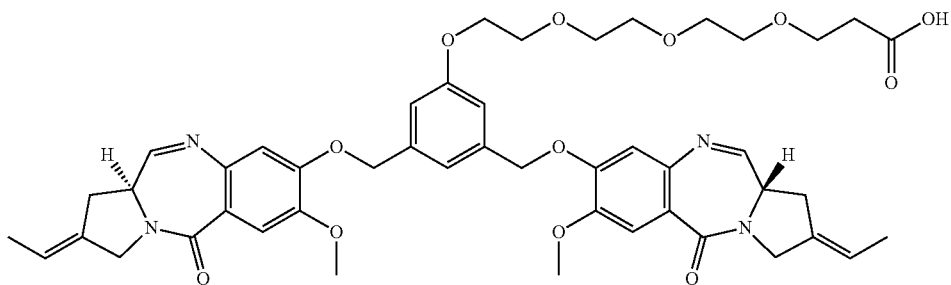

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid, starting with 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid methyl ester: LC/MS (Method A3): ES: m/z 867 (M+H)$^+$; m/z 434 (M+2H)$^{2+}$/2; RT=0.84 min; $^1$H NMR (400 MHz, CDCl$_3$-d1, δ ppm): δ=1.76 (dd, J=8.6, 1.5 Hz, 6H); 2.61 (t, 2H); 2.94-3.00 (m, 4H); 3.63-3.75 (m, 8H); 3.80 (t, J=6.5 Hz, 2H); 3.85-3.95 (m, 4H); 3.98 (s, 6H); 4.17 (t, J=4.9 Hz, 2H); 4.27 (br. s., 4H); 5.14-5.21 (m, 2H); 5.18 (d, J=12.7 Hz, 2H); 5.23 (d, 2H); 5.23 (d, J=12.7 Hz, 2H); 5.62 (td, J=4.5, 2.2 Hz, 2H); 6.88 (d, J=0.5 Hz, 2H); 6.97-7.02 (m, 2H); 7.09 (s, 1H); 7.54 (s, 2H); 7.68 (d, J=4.9 Hz, 2H)

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid methyl ester

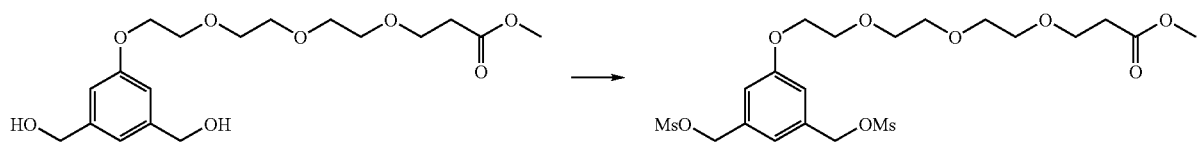

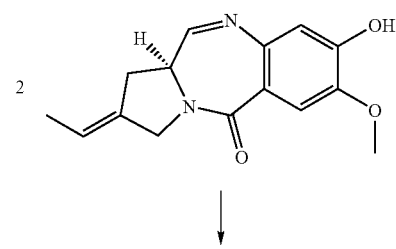

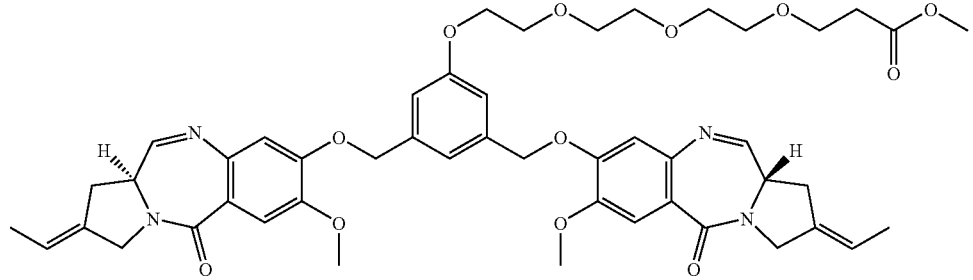

3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid methyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with 3-(2-{2-[2-(3,5-Bis-hydroxymethyl]-phenoxy)-ethoxy]-ethoxy}-ethoxy)-propionic acid methyl ester: LC/MS (Method A3): ES: m/z 881 (M+H)$^+$; m/z 441 (M+2H)$^{2+}$/2; RT=0.91 min; $^1$H NMR (400 MHz, CDCl$_3$-d1, δ ppm): δ=1.75 (d broad, J=6.7 Hz, 6H); 2.60 (t, J=6.7 Hz, 2H); 2.97 (m, 4H); 3.54-4.21 (m, 16H); 3.68 (s, 3H); 3.97 (s, 6H); 4.27 (m, 4H); 5.13 (d, J=12.2 Hz, 2H); 5.21 (d, J=12.2 Hz, 2H); 5.61 (m, 2H); 6.83 (s, 2H); 6.96 (s, 2H); 7.08 (s, 1H); 7.53 (s, 2H); 7.64 (d, J=4.2 Hz, 2H)

3-(2-{2-[2-(3,5-Bis-hydroxymethyl]-phenoxy)-ethoxy]-ethoxy}-ethoxy)-propionic acid methyl ester may be Prepared as Follows

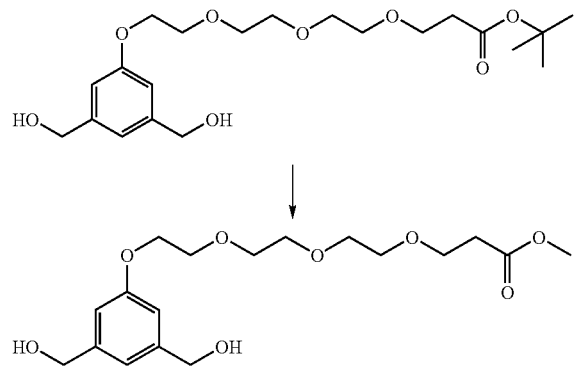

To a solution of 3-(2-{2-[2-(3,5-Bis-hydroxymethyl]-phenoxy)-ethoxy]-ethoxy}-ethoxy)-propionic acid tert-butyl ester (607 mg) in DCM (8.7 mL) was added trifluoroacetic acid (2.2 mL). The reaction mixture was stirred for 3 days at it then concentrated in vacuo and the obtained residue was dissolved in methanol (5 mL). To the cooled (0° C.) methanolic solution was added (trimethylsilyl)diazomethane 2M in hexanes (3.6 mL) until persistence of the yellow colour. Acetic acid (10 µL) was then added and the resulting solution was concentrated in vacuo to a residue. The residue was purified by silica gel chromatography (Analogix Super Flash SiO$_2$ SF25-40 g), using gradient elution with a mixture of DCM (A) and MeOH (B) (gradient: 99% A: 1% B down to 90% A: 10% B) to give 3-(2-{2-[2-(3,5-Bis-hydroxymethyl]-phenoxy)-ethoxy]-ethoxy}-ethoxy)-propionic acid methyl ester (232 mg). LC/MS (Method A3): ES: m/z 373 (M+H)$^+$; m/z 395 (M+Na)$^+$; RT=0.50 min 3-(2-{2-[2-(3,5-Bis-hydroxymethyl]-phenoxy)-ethoxy]-ethoxy}-ethoxy)-propionic acid tert-butyl ester

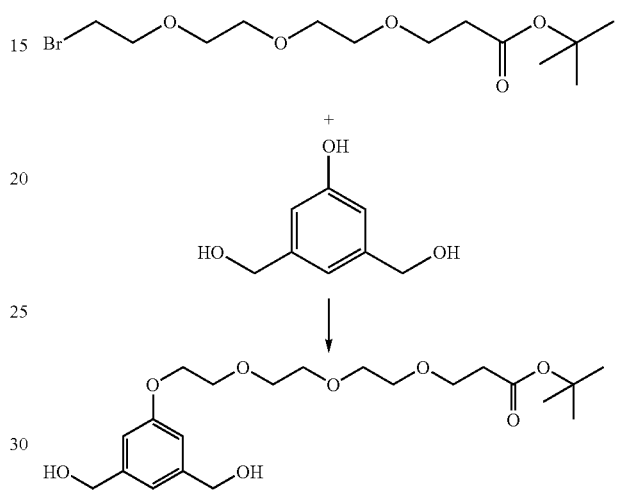

3-(2-{2-[2-(3,5-Bis-hydroxymethyl]-phenoxy)-ethoxy]-ethoxy}-ethoxy)-propionic acid tert-butyl ester may be prepared following the procedure for the preparation of 4-(3,5-Bis-hydroxymethyl-phenoxy)-butyric acid methyl ester, starting with 3-{2-[2-(2-Bromo-ethoxy)-ethoxy]-ethoxy}-propionic acid tert-butyl ester (WO 2004/091542): LC/MS (Method A3): ES m/z 415 (M+H)$^+$; m/z 432 (M+NH$_4$)$^+$; RT=0.75 min Example 4

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid N-hydroxysuccinimidyl ester

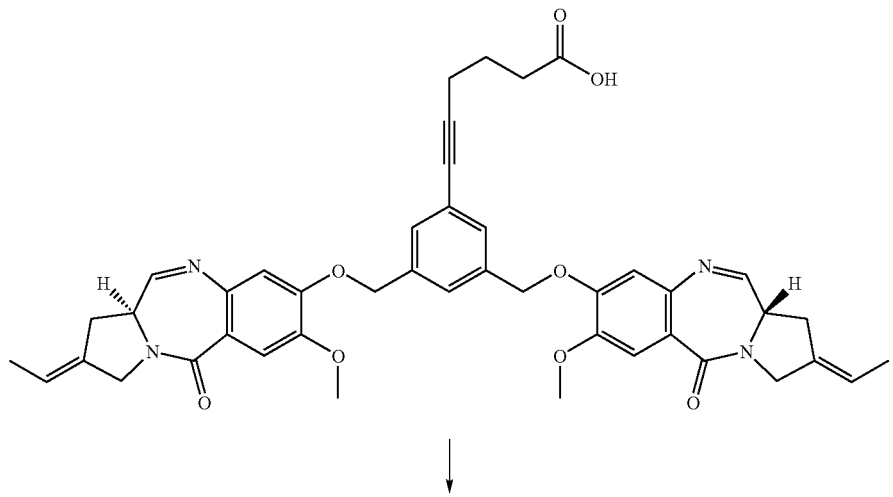

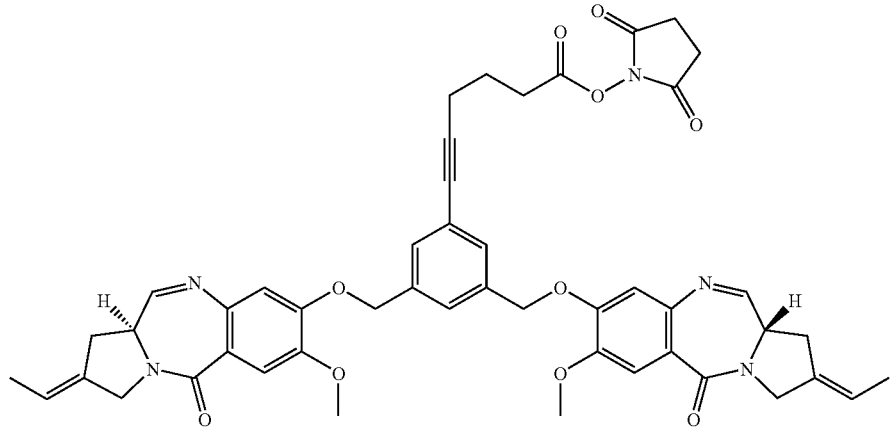

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid N-hydroxysuccinimidyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester, starting with 6-(3,5-Bis-[(S)-2-eth-(E)-ylidene-7-methoxy-1,2,3,11a-tetrahydro-pyrrolo[2,1c][1,4]benzodiazepin-5-one-8-yloxy methyl]-phenyl)-hex-5-ynoic acid: LC/MS (Method A3): ES: m/z 854 (M+H)$^+$; RT=1.25 min 6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid

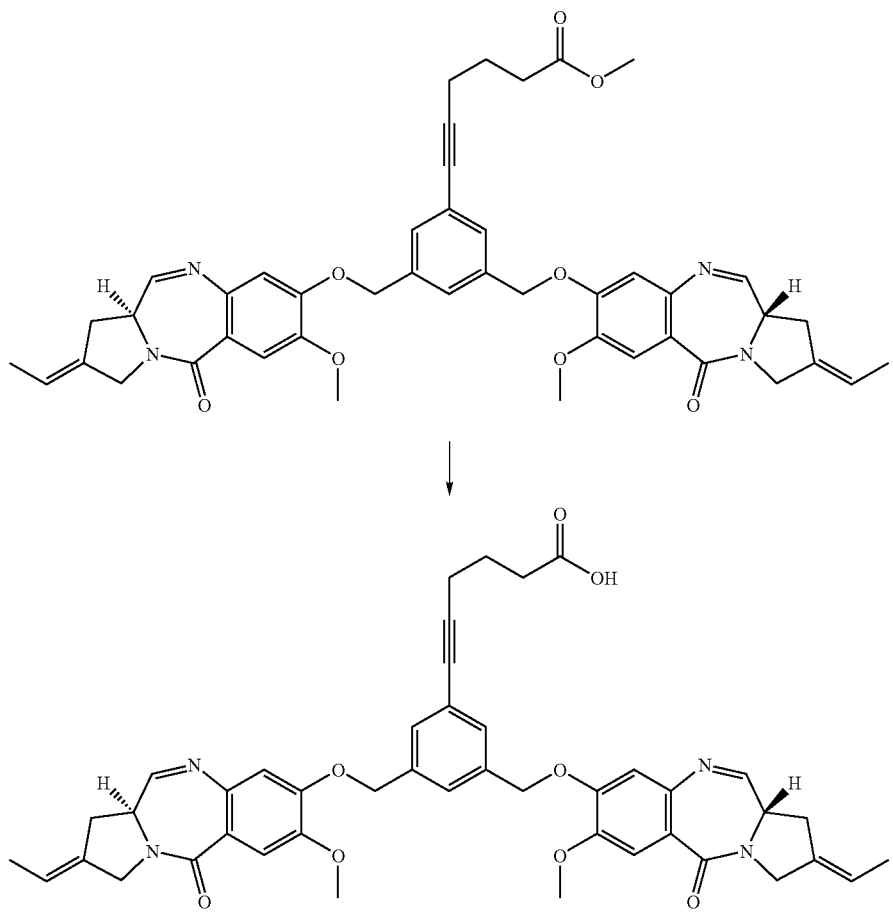

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid, starting with 6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid methyl ester LC/MS (Method A3): ES: m/z 757 (M+H)$^+$;

RT=0.89 min; $^1$H NMR (400 MHz, CDCl$_3$-d1, δ ppm): δ=1.76 (d, J=6.8 Hz, 6H); 1.98 (m, 2H); 2.55 (m, 4H); 2.97 (m, 4H); 3.91 (m, 2H); 3.97 (s, 6H); 4.27 (m, 4H); 5.15 (d, J=12.8 Hz, 2H); 5.21 (d, J=12.8 Hz, 2H); 5.61 (m, 2H); 6.88 (s, 2H); 7.48 (s, 3H); 7.53 (s, 2H); 7.67 (m, 2H)

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid methyl ester

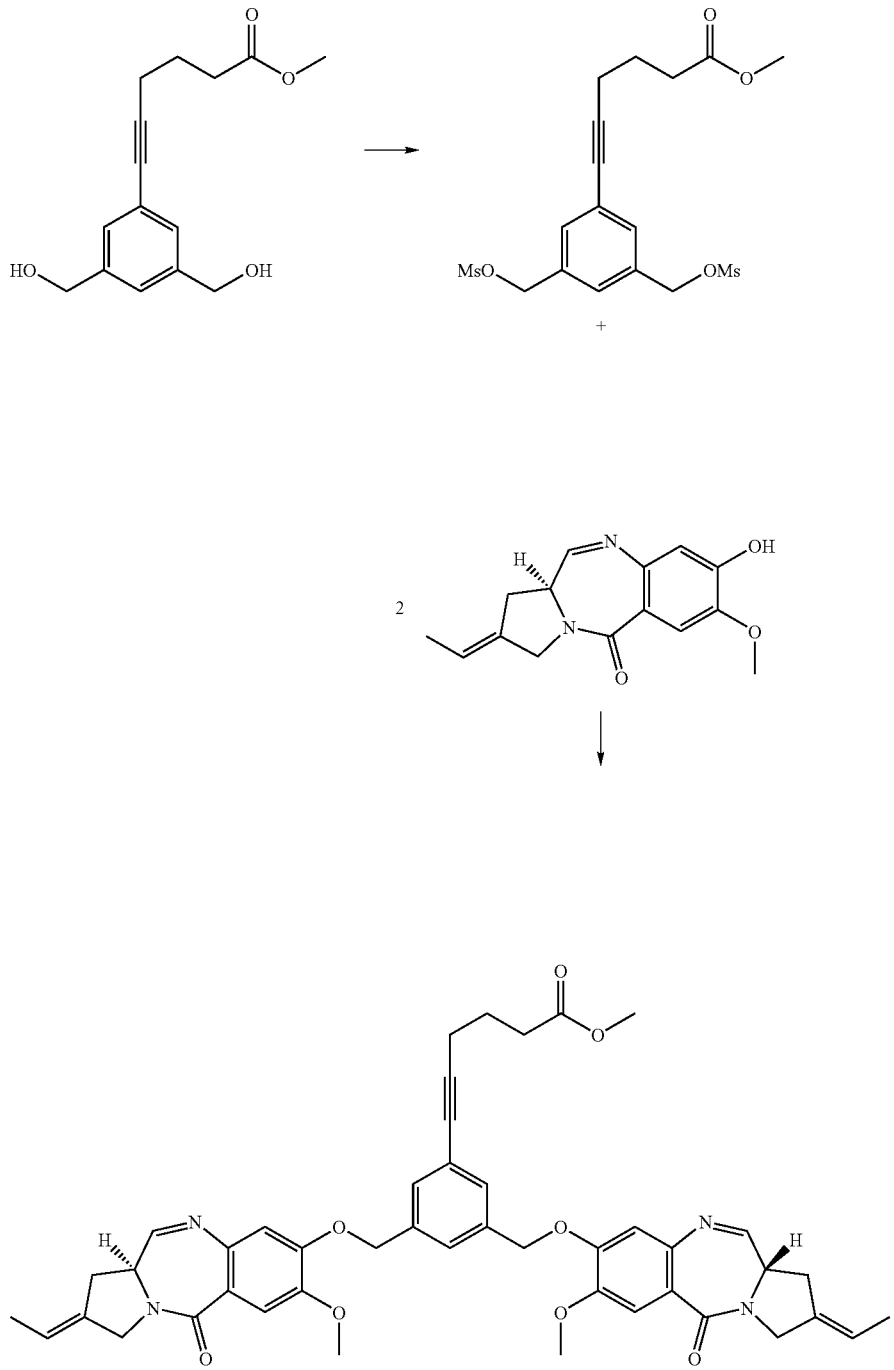

6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid methyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with 6-(3,5-Bis-hydroxymethyl-phenyl)-hex-5-ynoic acid methyl ester: LC/MS (Method A3): ES: m/z 771 (M+H)$^+$; RT=1.00 min; $^1$H NMR (500 MHz, CDCl$_3$-d1, δ ppm): δ=1.75 (d, J=6.6 Hz, 6H); 1.93 (m, 2H); 2.50 (m, 4H); 2.96 (m, 4H); 3.69 (s, 3H); 3.90 (m, 2H); 3.97 (s, 6H); 4.27 (m, 4H); 5.12 (d, J=12.3 Hz, 2H); 5.19 (d, J=12.3 Hz, 2H); 5.61 (m, 2H); 6.81 (s, 2H); 7.43 (s, 3H); 7.54 (s, 2H); 7.64 (d, J=4.4 Hz, 2H)

6-(3,5-Bis-hydroxymethyl-phenyl)-hex-5-ynoic acid methyl ester is Prepared as Follows

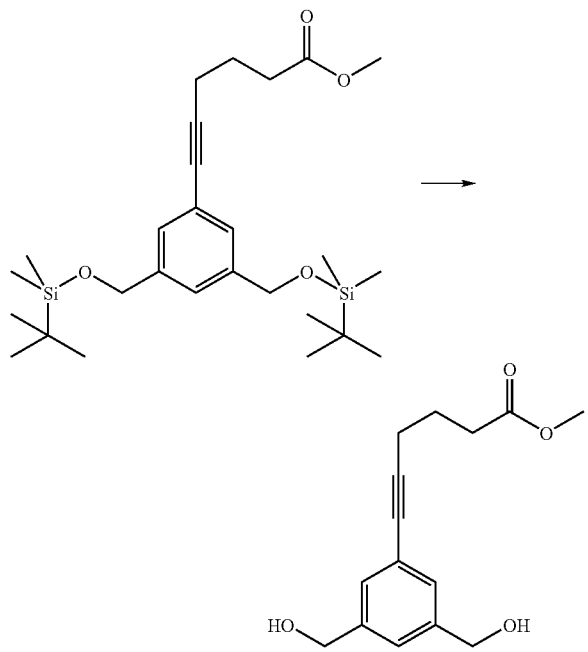

To a cooled (0° C.) solution of 6-[3,5-Bis-(tert-butyl-dimethyl-silyloxymethyl)-phenyl]-hex-5-ynoic acid methyl ester (140 mg) in anhydrous tetrahydrofurane (0.3 mL) was slightly added a solution of tetrabutylammonium fluoride 1 M in THF (716 μL). After 75 min at rt, ethyl acetate (20 mL) was added and the organic phase was washed three times with water (5 mL) and once with a saturated aqueous solution of sodium chloride (5 mL), dried over sodium sulfate and concentrated in vacuo to a residue. The residue was purified by silica gel chromatography (Merck SuperVarioFlash 15 g column, Si60 15-40 μm), using gradient elution with a mixture of heptane (A)/ethyl acetate (B), (gradient: 50% A: 50% B down to 10% A: 90% B) to give 6-(3,5-Bis-hydroxymethyl-phenyl)-hex-5-ynoic acid methyl ester (64.3 mg) as a pale yellow oil. LC/MS (Method A3): ES: m/z 263 (M+H)$^+$; RT=0.62 min

6-[3,5-Bis-(tert-butyl-dimethyl-silyloxymethyl)-phenyl]-hex-5-ynoic acid methyl ester may be Prepared as Follows

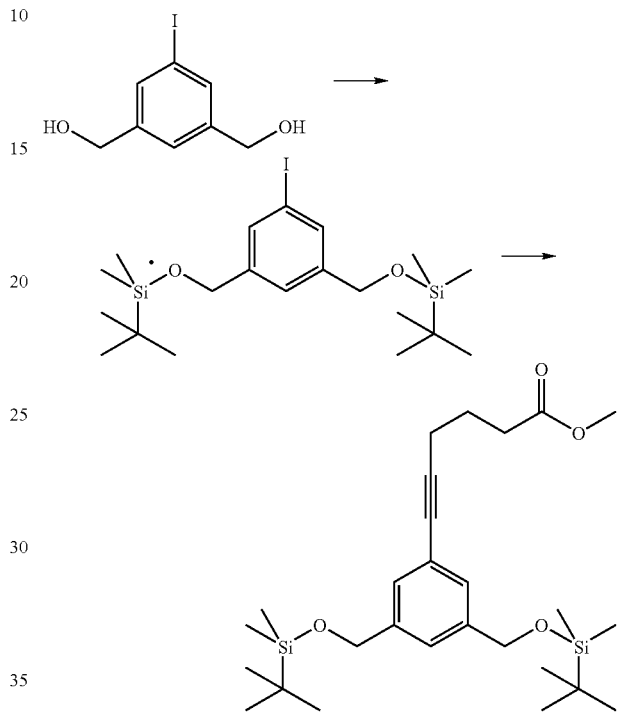

To a solution of 1,3-Bis-hydroxymethyl-5-iodo-benzene (Zeng, F.; Zimmerman, S. C. J. Am. Chem. Soc. 1996, 118 (22), 5326-5327) (1.7 g) in dichloromethane (10 mL), were added triethylamine (3.59 mL), tert-butyldimethylsilyl chloride (2.91 g) and DMF (2 mL). After 1 hour, ethyl acetate (200 mL) was added and the organic phase was washed three times with water (50 mL) and once with a saturated aqueous solution of sodium chloride (50 mL), dried over magnesium sulfate and concentrated in vacuo to a residue (3.65 g). To a solution of the previous residue (200 mg) in DMF (0.90 mL) were added copper(I) iodide (7.7 mg), dichlorobis(triphenylphosphine)palladium (II) (28.5 mg), 5-hexynoic acid methyl ester (102.4 mg) and triethylamine (113 μL). After 45 min, ethyl acetate (40 mL) was added and the organic phase was washed three times with water (10 mL) and once with a saturated aqueous solution of sodium chloride (10 mL), dried over magnesium sulfate and concentrated in vacuo to a residue. The residue was purified by silica gel chromatography (Merck SuperVarioFlash 30 g column, Si60 15-40 μm), using gradient elution with a mixture of heptane (A)/ethyl acetate (B), (gradient: 100% A down to 90% A: 10% B) to give 6-[3,5-Bis-(tert-butyl-dimethyl-silyloxymethyl)-phenyl]-hex-5-ynoic acid methyl ester (145.3 mg) as a yellow oil. MS (Method C): Cl: m/z 494 (M+NH$_4$)$^+$; $^1$H N.M.R. (400 MHz, DMSO-d6, δ in ppm): δ=0.07 (s, 12H); 0.89 (s, 18H); 2.55-2.69 (m, 2H); 3.63 (s, 3H); 4.67 (s, 4H); 7.15 (s large, 2H); 7.28 (s broad, 1H)

Example 5

3-(2-{2-[2-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-ethoxy]-ethoxy}-ethoxy)-propionic acid methyl ester

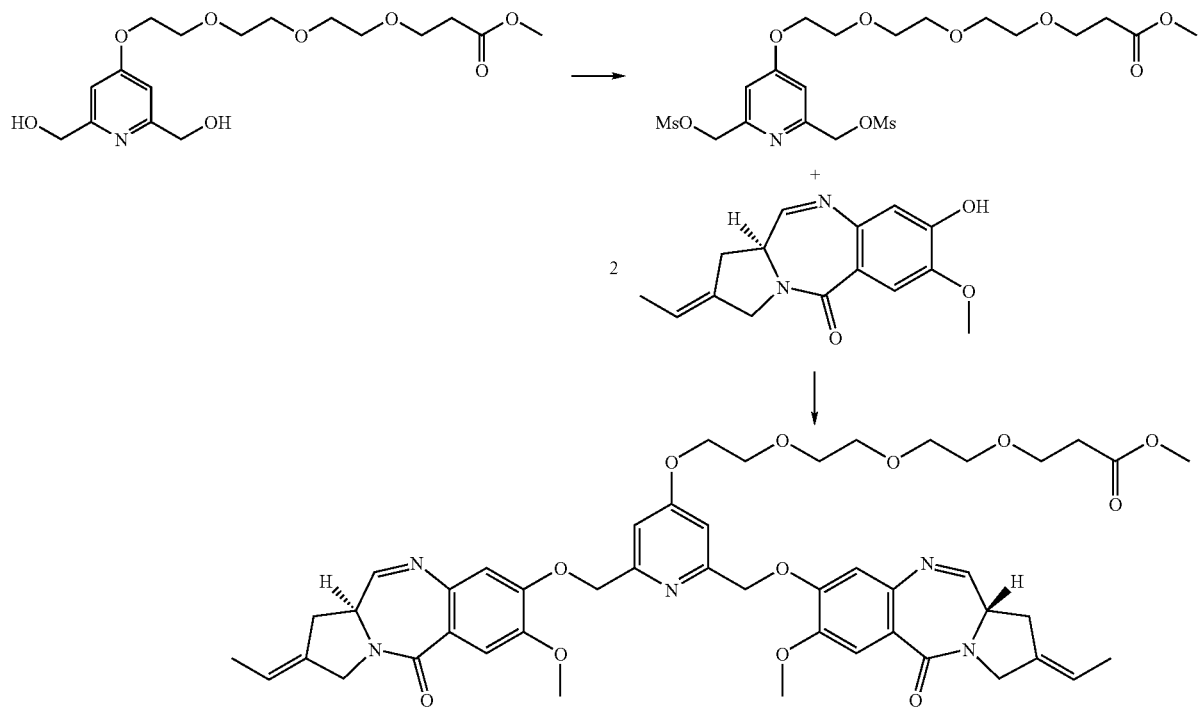

3-(2-{2-[2-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-ethoxy]-ethoxy}-ethoxy)-propionic acid methyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with 3-(2-{2-[2-(2,6-Bis-hydroxymethyl-pyridin-4-yloxy)-ethoxy]-ethoxy}-ethoxy)-propionic acid methyl ester: LC/MS (Method A3): ES: m/z 882 (M+H)$^+$; m/z 441.5 (M+2H)$^{2+}$/2; RT=0.82 min; $^1$H NMR (400 MHz, CDCl$_3$-d1, δ ppm): δ=1.76 (d, J=6.8 Hz, 6H); 2.59 (t, J=6.5 Hz, 2H); 2.97 (m, 4H); 3.58-3.72 (m, 9H); 3.75 (t, J=6.5 Hz, 2H); 3.80-3.97 (m, 4H); 4.00 (s, 6H); 4.20 (m broad, 2H); 4.27 (m, 4H); 5.31-5.42 (m, 4H); 5.61 (m broad, 2H); 6.87 (s, 2H); 7.02-7.15 (m broad, 2H); 7.56 (s, 2H); 7.65 (d, J=4.4 Hz, 2H).

3-(2-{2-[2-(2,6-Bis-hydroxymethyl-pyridin-4-yloxy)-ethoxy]-ethoxy}-ethoxy)-propionic acid methyl ester

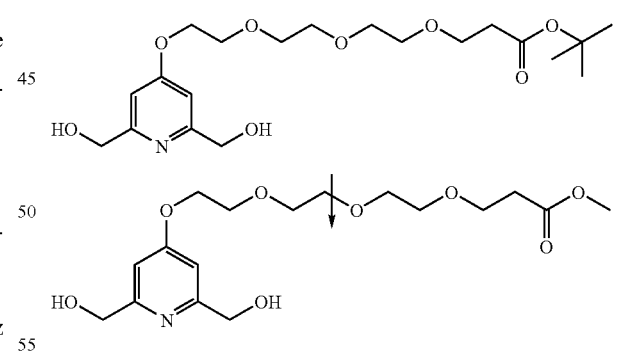

3-(2-{2-[2-(2,6-Bis-hydroxymethyl-pyridin-4-yloxy)-ethoxy]-ethoxy}-ethoxy)-propionic acid methyl ester may be prepared following the procedure for the preparation of 3-(2-{2-[2-(3,5-Bis-hydroxymethyl]-phenoxy)-ethoxy]-ethoxy}-ethoxy)-propionic acid methyl ester, starting with 3-(2-{2-[2-(2,6-Bis-hydroxymethyl-pyridin-4-yloxy)-ethoxy]-ethoxy}-ethoxy)-propionic acid tert-butyl ester: LC/MS (Method A3): ES: m/z 374 (M+H)$^+$; m/z 418 (M+HCO$_2$H−H)$^-$; RT=0.31 min 3-(2-{2-[2-(2,6-Bis-hydroxymethyl-pyridin-4-yloxy)-ethoxy]-ethoxy}-ethoxy)-propionic acid tert-butyl ester

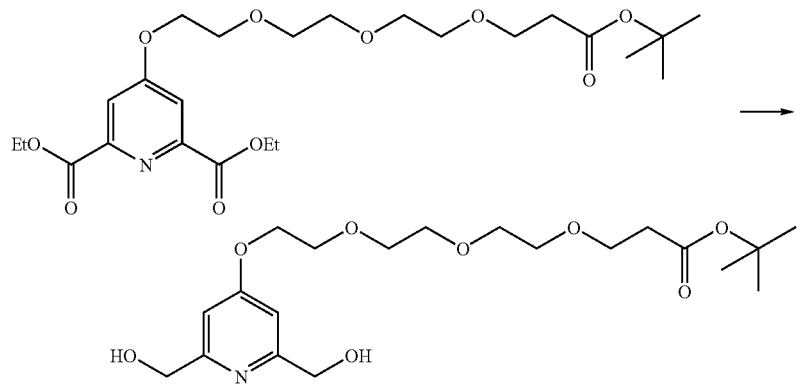

To a solution of 4-(2-{2-[2-(2-tert-Butoxycarbonyl-ethoxy)-ethoxy]-ethoxy}-ethoxy)-pyridine-2,6-dicarboxylic acid diethyl ester (1.36 g) in absolute ethanol (72 mL) was added sodium borohydride (309 mg) and calcium chloride (921 mg). After stirring for 30 mn, hydrogen evolution ceased, and reaction was quenched with water. After concentration under reduced pressure, ammonium chloride was added and the aqueous phase was extracted three times with ethyl acetate. The combined organic solutions were dried over magnesium sulfate, and concentrated in vacuo to a residue. The residue was purified by silica gel chromatography (Analogix Super Flash $SiO_2$ SF25-80 g), using gradient elution with a mixture of DCM (A) and MeOH (B) (gradient: 100% A down to 90% A: 10% B) to give 3-(2-{2-[2-(2,6-Bis-hydroxymethyl-pyridin-4-yloxy)-ethoxy]-ethoxy}-ethoxy)-propionic acid tert-butyl ester (720 mg): LC/MS (Method A3): ES: m/z 416 (M+H)$^+$; RT=0.52 min 4-(2-{2-[2-(2-tert-Butoxycarbonyl-ethoxy)-ethoxy]-ethoxy}-ethoxy)-pyridine-2,6-dicarboxylic acid diethyl ester

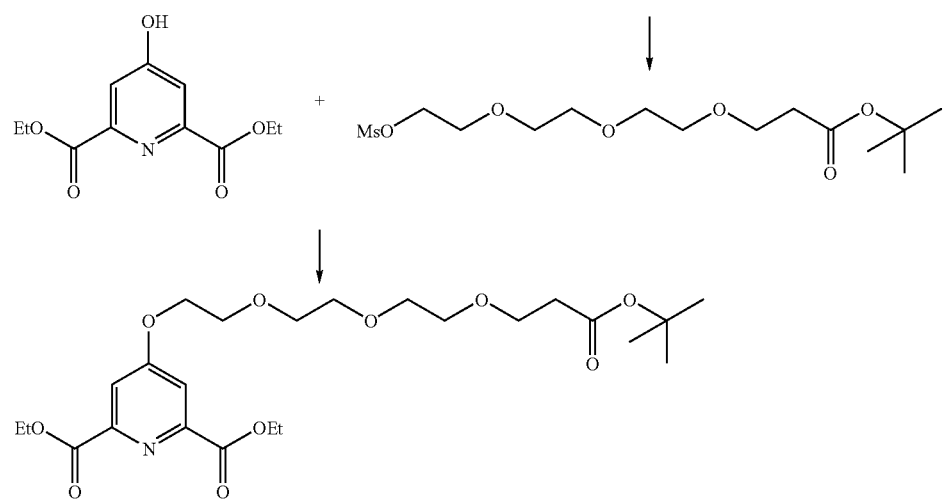

To a cooled (0° C.) solution of 12-hydroxy-4,7,10-trioxadecanoic acid tert-butyl ester (1.91 mL) in DCM (12.9 mL) were added triethylamine (1.13 mL), was added methanesulfonyl chloride (622 µL). After 3 hours, the reaction mixture was concentrated in vacuo to a residue then dissolved in ethyl acetate (13 mL). The insoluble part was filtered off, washed twice with ethyl acetate (7 mL) and the combined organic solutions were concentrated in vacuo to a residue (2.77 g). To a solution of 1.64 g of the residue in dry acetonitrile (10 mL) were added the diethyl ester of chelidamic acid (Scrimin, P.; Tecilla, P.; Tonellato, U.; Vendrame, T. *J. Org. Chem.* 1989, 54, 5988) (1 g) and potassium carbonate (2.88 g). After refluxing for 24 h, the unsoluble part was filtered off and washed with ethyl acetate. The organic phase was then concentrated in vacuo to a residue. The residue was purified by silica gel chromatography (Merck SuperVarioPrep 200 g column, Si60 15-40 µm), using gradient elution with a mixture of DCM (A) and MeOH (B) (gradient:100% A down to 97% A: 3% B) to give 4-(2-{2-[2-(2-tert-Butoxycarbonyl-ethoxy)-ethoxy]-ethoxy}-ethoxy)-pyridine-2,6-dicarboxylic acid diethyl ester (1.36 g): LC/MS (Method A4): ES: m/z 500 (M+H)$^+$; m/z 522 (M+Na)$^+$; m/z 444 (M–C$_4$H$_8$+H)$^+$; RT=4.32 min

Example 6

4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid N-hydroxysuccinimidyl ester 4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid N-hydroxysuccinimidyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester, starting with 4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid: LC/MS (Method A3): ES: m/z 847 (M+H)$^+$; m/z 424 (M+2H)$^{2+}$/2; RT=0.80 min; $^1$H NMR (400 MHz, CDCl$_3$-d1, δ ppm): 1.75 (d broad, J=6.6 Hz, 6H); 2.23 (m broad, 2H); 2.76-2.89 (m broad, 6H); 2.97 (m broad, 4H); 3.91 (m broad, 2H); 4.00 (s broad, 6H); 4.14 (m broad, 2H); 4.27 (m broad, 4H); 5.28 (m broad, 4H); 5.61 (m broad, 2H); 6.87 (s broad, 2H); 7.03 (s broad, 2H); 7.56 (s broad, 2H); 7.65 (m broad, 2H)

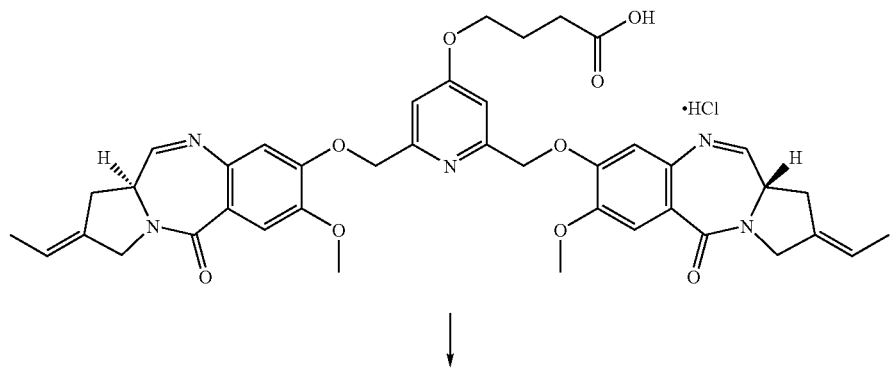

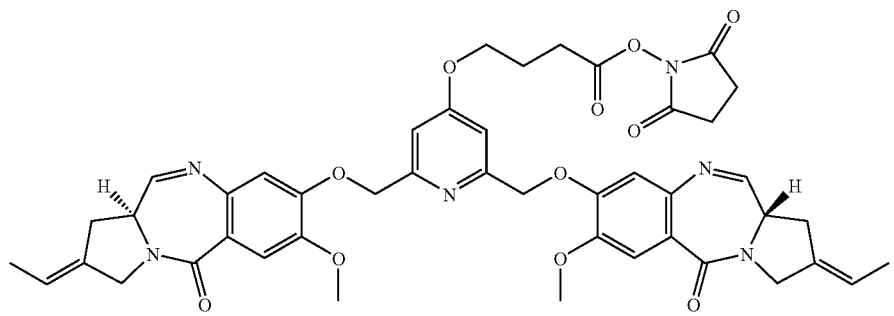

4-(2,6-Bis-[(S)-2-eth-(E)-ylidene-7-methoxy-1,2,3,
11a-tetrahydro-pyrrolo[2,1c][1,4]benzodiazepin-5-
one-8-yloxymethyl]-pyridin-4-yloxy)-butyric acid
hydrochloride

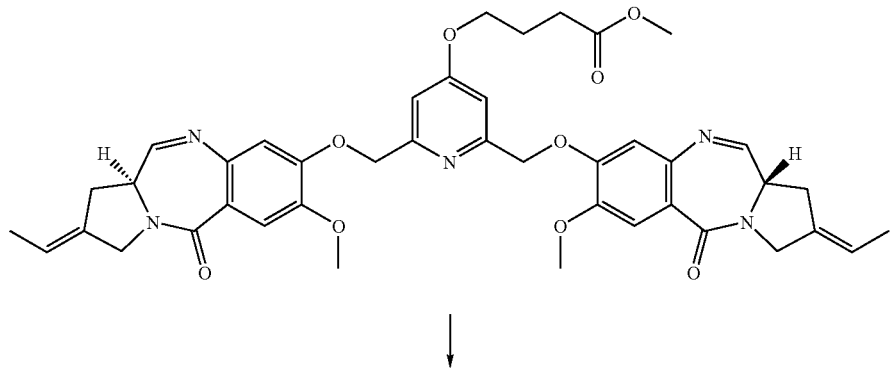

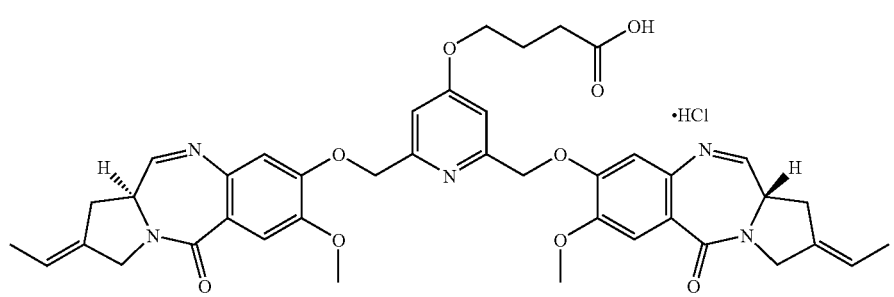

4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid hydrochloride may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid, starting with 4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid methyl ester: LC/MS (Method A3): ES: m/z 750 (M+H)$^+$; m/z 375.5 (M+2H)$^{2+}$/2 m/z 332.5 (M−C$_4$H$_6$O$_2$+2H)$^{2+}$2; RT=0.73 min; $^1$H NMR (400 MHz, CDCl$_3$-d1, δ ppm): δ=1.75 (d, J=6.6 Hz, 6H); 2.02 (m, 2H); 2.42 (m, 2H); 2.97 (m, 4H); 3.83-4.14 (m, 4H); 4.00 (s, 6H); 4.27 (m, 4H); 5.20-5.42 (m, 4H); 5.61 (m, 2H); 6.85 (s, 2H); 6.94 (s, 2H); 7.56 (s, 2H); 7.63 (m, 2H)

4-(2,6-Bis-[(S)-2-eth-(E)-ylidene-7-methoxy-1,2,3,
11a-tetrahydro-pyrrolo[2,1c][1,4]benzodiazepin-5-
one-8-yloxymethyl]-pyridin-4-yloxy)-butyric acid
methyl ester

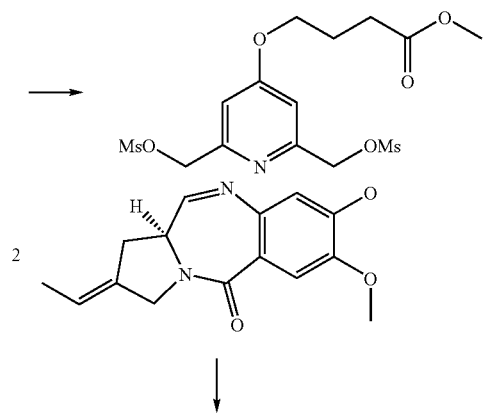

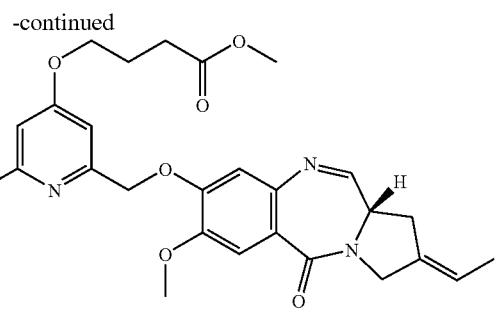

4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid methyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with 4-(2,6-Bis-hydroxymethyl-pyridin-4-yloxy)-butyric acid methyl ester: LC/MS (Method A4): ES: m/z 764 (M+H)$^+$ m/z 664 (M−C$_5$H$_8$O$_2$+H)$^+$ m/z 762 (M−H)$^-$ RT=3.64 min; 1H NMR (500 MHz, CDCl$_3$-d1, δ ppm): δ=1.76 (d, J=6.8 Hz, 6H); 2.12 (m, 2H); 2.50 (t, J=7.3 Hz, 2H); 2.97 (m, 4H); 3.68 (s, 3H); 3.90 (m, 2H); 4.00 (s, 6H); 4.07 (m broad, 2H); 4.27 (m, 4H); 5.29 (m broad, 4H); 5.61 (m, 2H); 6.86 (s, 2H); 6.99 (s broad, 2H); 7.56 (s, 2H); 7.65 (d, J=4.4 Hz, 2H)

4-(2,6-Bis-hydroxymethyl-pyridin-4-yloxy)-butyric acid methyl ester

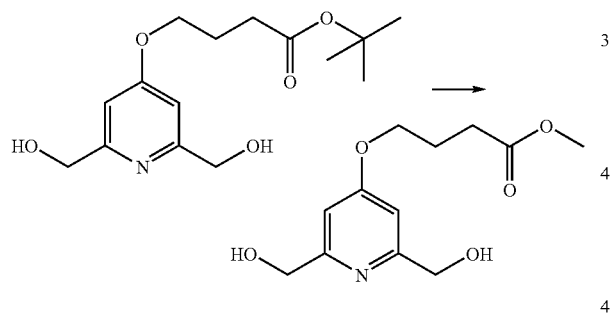

4-(2,6-Bis-hydroxymethyl-pyridin-4-yloxy)-butyric acid methyl ester may be prepared following the procedure for the preparation of 3-(2-{2-[2-(3,5-Bis-hydroxymethyl]-phenoxy)-ethoxy]-ethoxy}-ethoxy)-propionic acid methyl ester, starting with 4-(2,6-bis-hydroxymethyl-pyridin-4-yloxy)-butyric acid tert-butyl ester: LC/MS (Method A3): ES: m/z 256 (M+H)$^+$ RT=0.25 min 4-(2,6-Bis-hydroxymethyl-pyridin-4-yloxy)-butyric acid tert-butyl ester

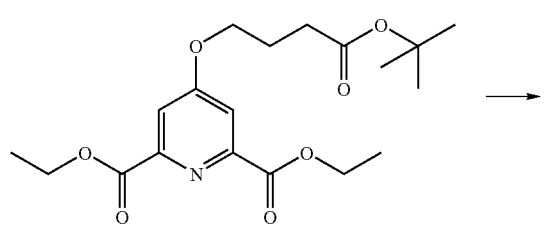

4-(2,6-Bis-hydroxymethyl-pyridin-4-yloxy)-butyric acid tert-butyl ester may be prepared following the procedure for the preparation of 3-(2-{2-[2-(2,6-bis-hydroxymethyl-pyridin-4-yloxy)-ethoxy]-ethoxy}-ethoxy)-propionic acid tert-butyl ester, starting with 4-(3-tert-butoxycarbonyl-propoxy)-pyridine-2,6-dicarboxylic acid diethyl ester: LC/MS (Method A4): ES: m/z 298 (M+H)$^+$; m/z 156 (M−C$_8$H$_{14}$O$_2$+H)$^+$; RT=2.45 min 4-(3-tert-Butoxycarbonyl-propoxy)-pyridine-2,6-dicarboxylic acid diethyl ester

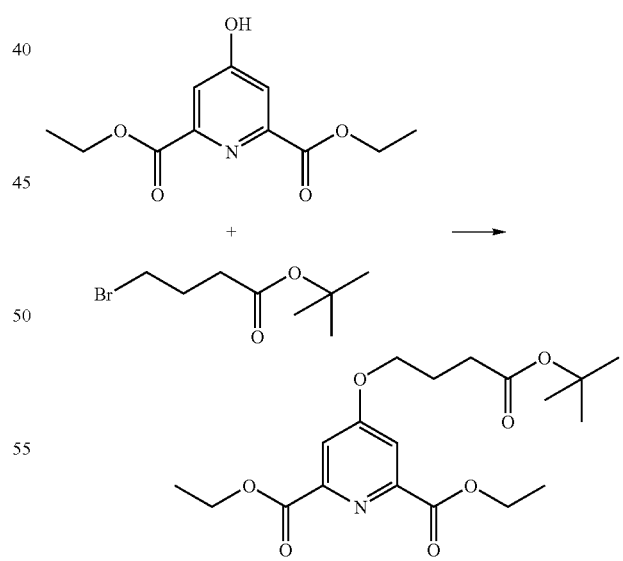

4-(3-tert-Butoxycarbonyl-propoxy)-pyridine-2,6-dicarboxylic acid diethyl ester may be prepared following the procedure for the preparation of 4-(2-{2-[2-(2-tert-butoxycarbonyl-ethoxy)-ethoxy]-ethoxy}-ethoxy)-pyridine-2,6-dicarboxylic acid diethyl ester, starting with 4-bromo-butyric acid tert-butyl ester: LC/MS (Method A4): E: m/z 382

(M+H)+ m/z 404 (M+Na)+ m/z 785 (2M+Na)+ m/z 240 (M−C$_8$H$_{14}$O$_2$+H)+ RT=4.65 min

Example 7

N-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethyl]-N-methyl-succinamic acid methyl ester

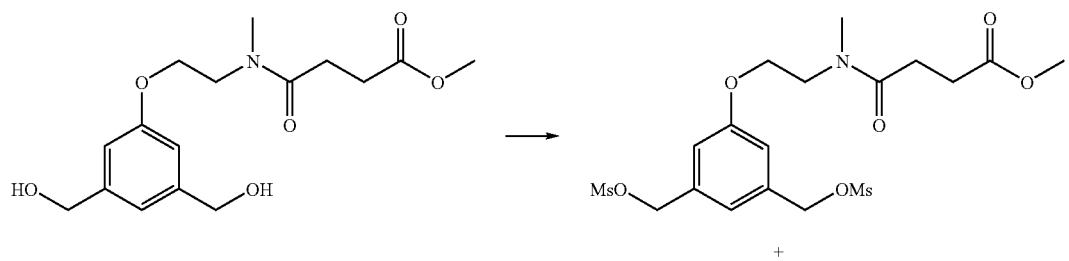

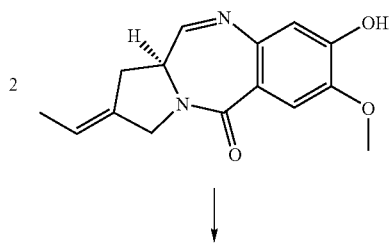

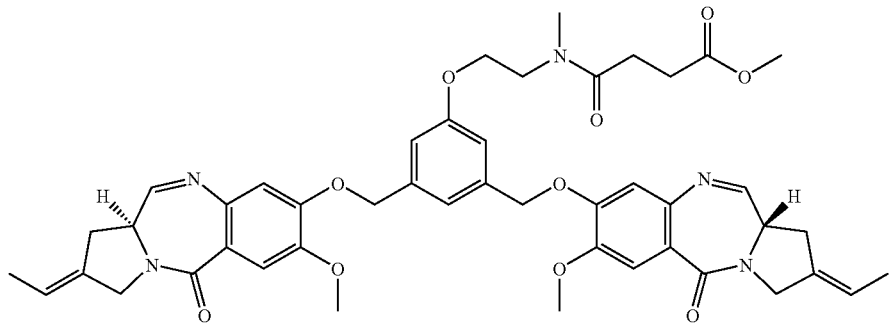

N-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethyl]-N-methyl-succinamic acid methyl ester may be prepared following the procedure for the preparation of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester, starting with N-[2-(3,5-Bis-hydroxymethyl-phenoxy)-ethyl]-N-methyl-succinamic acid methyl ester: LC/MS (Method A3): ES: m/z 834 (M+H)+ RT=0.87 min; $^1$H NMR (400 MHz, CDCl$_3$-d1, δ ppm): δ=1.75 (d, J=6.6 Hz, 6H); 2.54-3.21 (m, 11H); 3.61-4.17 (m, 6H); 3.69 (s, 3H); 3.97 (s, 6H); 4.27 (m, 4H); 5.10-5.21 (m, 4H); 5.61 (m, 2H); 6.82 (s, 2H); 6.91-6.95 (m, 2H); 7.06-7.12 (m, 1H); 7.53 (s, 2H); 7.63 (d, J=4.4 Hz, 2H)

N-[2-(3,5-Bis-hydroxymethyl-phenoxy)-ethyl]-N-methyl-succinamic acid methyl ester may be Prepared as Follows

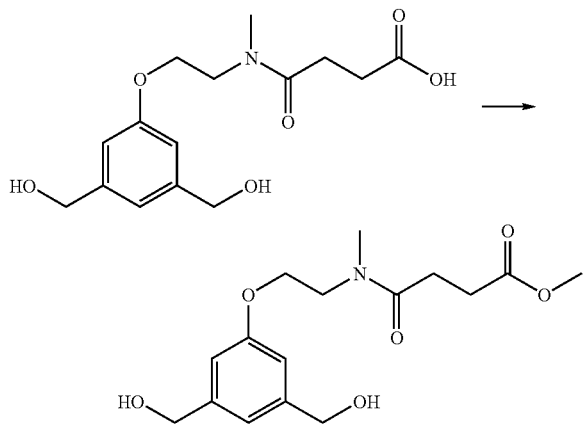

To a cooled (0° C.) solution of N-[2-(3,5-Bis-hydroxymethyl-phenoxy)-ethyl]-N-methyl-succinamic acid (225 mg) in methanol (1 mL), was added (trimethylsilyl)diazomethane 2M in hexanes (840 µL) until persistence of the yellow colour. After 40 min, ethyl acetate (5 mL) and acetic acid (50 µL) were added, then, one minute later, a saturated aqueous solution of sodium hydrogen carbonate until pH=7. The aqueous phase was extracted with ethyl acetate. The combined organic layers were washed with a saturated aqueous solution of sodium chloride, dried over magnesium sulfate and concentrated in vacuo to a residue. The residue was purified by silica gel chromatography (Merck SuperVarioFlash 25 g column, Si60 15-40 µm), using gradient elution with a mixture of DCM (A)/MeOH (B), (gradient: 98% A: 2% B down to 90% A: 10% B) to give N-[2-(3,5-Bis-hydroxymethyl-phenoxy)-ethyl]-N-methyl-succinamic acid methyl ester (103 mg). LC/MS (Method A3): ES: m/z 348 (M+Na)$^+$; m/z 326 (M+H)$^+$ m/z 308 (M–H$_2$O+H)$^+$; RT=0.43 min

N-[2-(3,5-Bis-hydroxymethyl-phenoxy)-ethyl]-N-methyl-succinamic acid may be Prepared as Follows

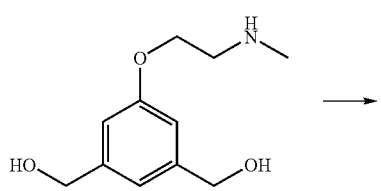

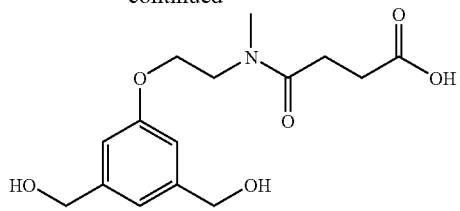

N-[2-(3,5-Bis-hydroxymethyl-phenoxy)-ethyl]-N-methyl-succinamic acid may be prepared following the procedure for the preparation of N-[2-(3,5-Bis-hydroxymethyl-phenoxy)-ethyl]-succinamic acid, starting with 3,5-Bis-hydroxymethyl-(2-methylamino-ethoxy)-benzene: LC/MS (Method A3): ES: m/z 312 (M+H)$^+$; m/z 294 (M–H$_2$O+H)$^+$ m/z 310 (M–H)$^-$; RT=0.35 min

3,5-Bis-hydroxymethyl-(2-methylamino-ethoxy)-benzene hydrochloride

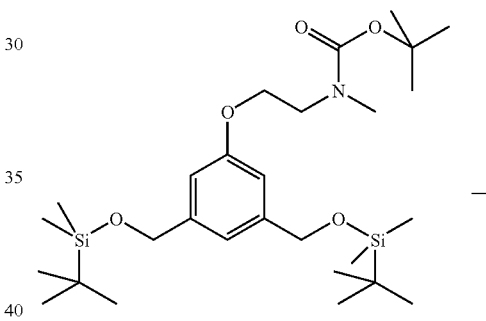

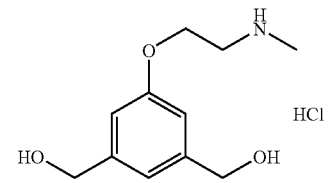

To a solution of 1-(2-(tert-butoxycarbonyl)-methylamino-ethoxy)-3,5-bis-(tert-butyl-dimethyl-silyloxy methyl)-benzene (590 mg) in dioxane (4 mL) was added a solution of hydrochloric acid 4N in dioxane (3.3 mL). After 15 h at rt, the resulting solid was filtered, washed with dioxane and dried in vacuo to give 3,5-bis-hydroxymethyl-(2-methylamino-ethoxy)-benzene hydrochloride (240 mg) as a white powder. LC/MS (Method A2): ES: m/z 212 (M+H)$^+$; RT=0.14 min

1-(2-(tert-butoxycarbonyl)-methylamino-ethoxy)-3,5-bis-(tert-butyl-dimethyl-silyloxymethyl)-benzene may be Prepared as Follows

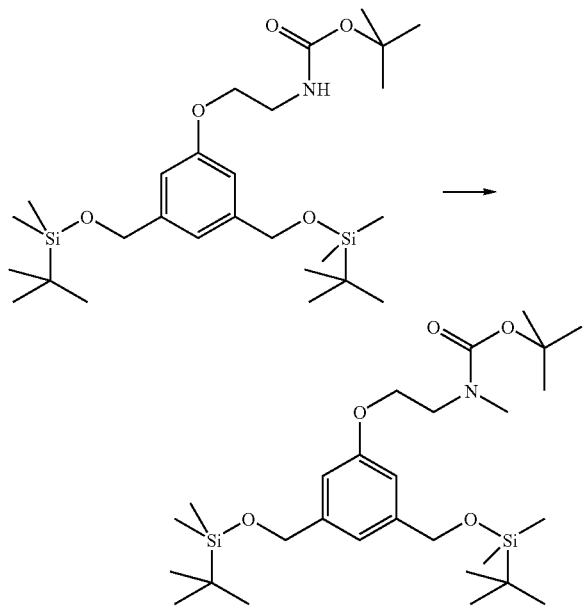

To a solution of 1-(2-tert-butoxycarbonylamino-ethoxy)-3,5-bis-(tert-butyl-dimethyl-silyloxymethyl)-benzene (270 mg) in tetrahydrofurane (5 mL) was added iodomethane (70 µL) and the reaction mixture was cooled (0° C.). To the cooled solution, sodium hydride was added (68 mg). After 1 hour, the temperature was allowed to warm up to room temperature. After 16 hours, a mixture of THF and water 1:1 (2 mL) was slightly added, then citric acid until pH=2. The aqueous phase was extracted three times with ethyl acetate. The combined organic layers were washed with a saturated aqueous solution of sodium chloride, dried over magnesium sulfate and concentrated in vacuo to a residue. The residue was purified by silica gel chromatography (Merck SuperVarioFlash 25 g column, Si60 15-40 µm), using gradient elution with a mixture of heptane (A)/ethyl acetate (B), (gradient: 100% A down to 85% A: 15% B) to give 1-(2-(tert-butoxycarbonyl)-methylamino-ethoxy)-3,5-bis-(tert-butyl-dimethyl-silyloxy methyl)-benzene (220 mg): LC/MS (Method A2): ES: m/z 562 (M+Na)$^+$; m/z 308 (M+H–C$_5$H$_8$O$_2$–OSiC$_6$H$_{16}$)$^+$; RT=1.50 min

1-(2-tert-butoxycarbonylamino-ethoxy)-3,5-bis-(tert-butyl-dimethylsilyloxy methyl)-benzene may be Prepared as Follows

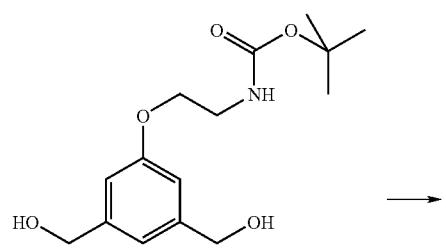

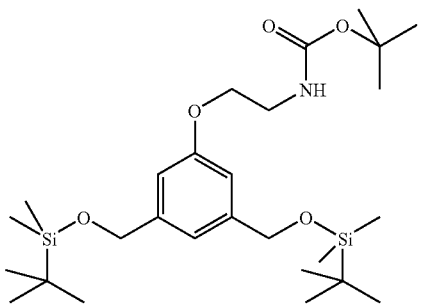

To a cooled (0° C.) solution of 1-(2-tert-butoxycarbonylamino-ethoxy)-3,5-bis-(hydroxymethyl)-benzene (600 mg) in DMF (8 mL) were added tert-butyldimethylchlorosilane (913 mg) and triethylamine (936 µL). After 18 hours, water was added and the aqueous phase was extracted twice with ethyl acetate. The combined organic layers were washed with a saturated aqueous solution of sodium chloride, dried over magnesium sulfate and concentrated in vacuo to give 1-(2-tert-butoxycarbonylamino-ethoxy)-3,5-bis-(tert-butyl-dimethyl-silyloxy methyl)-benzene (1 g): LC/MS (Method A2): ES: m/z 548 (M+Na)+; m/z 294 (M+H–C$_5$H$_8$O$_2$–OSiC$_6$H$_{16}$)$^+$; RT=1.45 min

Example 8

4-(3,5-Bis-[(S)-2-methylidene-7-methoxy-1,2,3,11a-tetrahydro-pyrrolo[2,1c][1,4]benzodiazepin-5-one-8-yloxymethyl]-phenyl)-propanoic acid N-hydroxysuccinimidyl ester, compound 10

Scheme 1

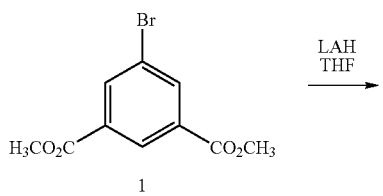

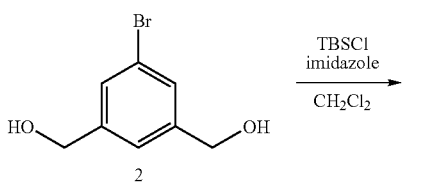

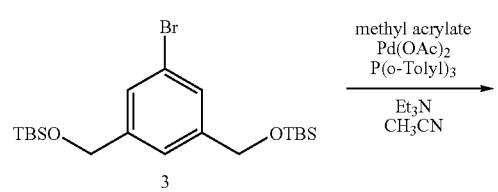

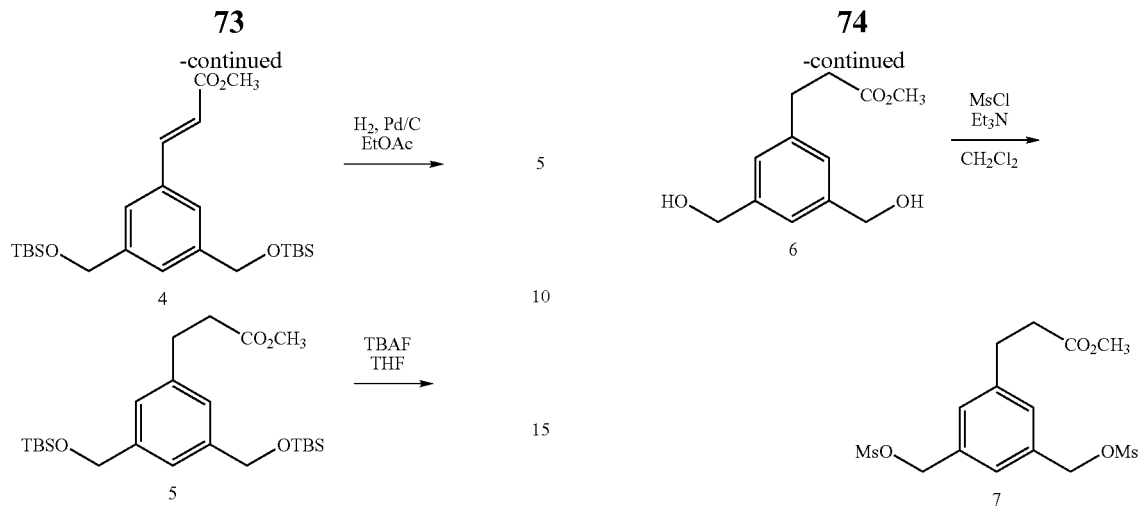
Scheme 2
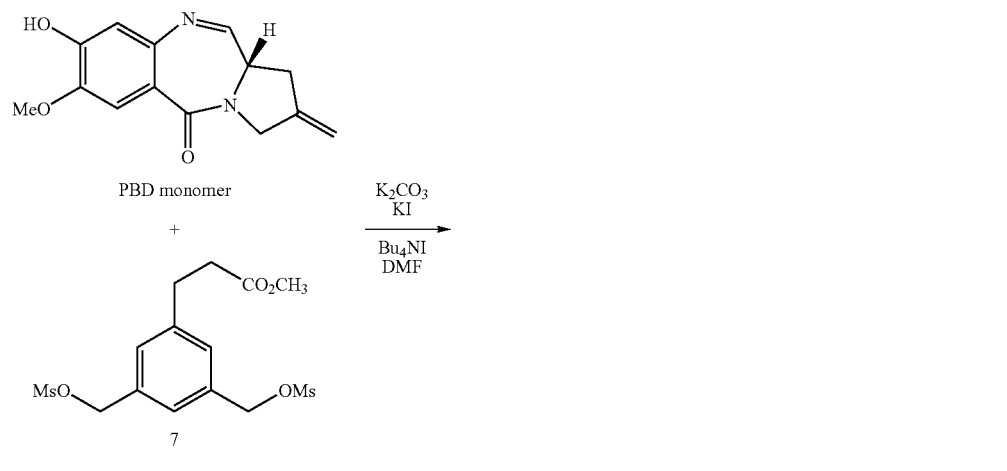
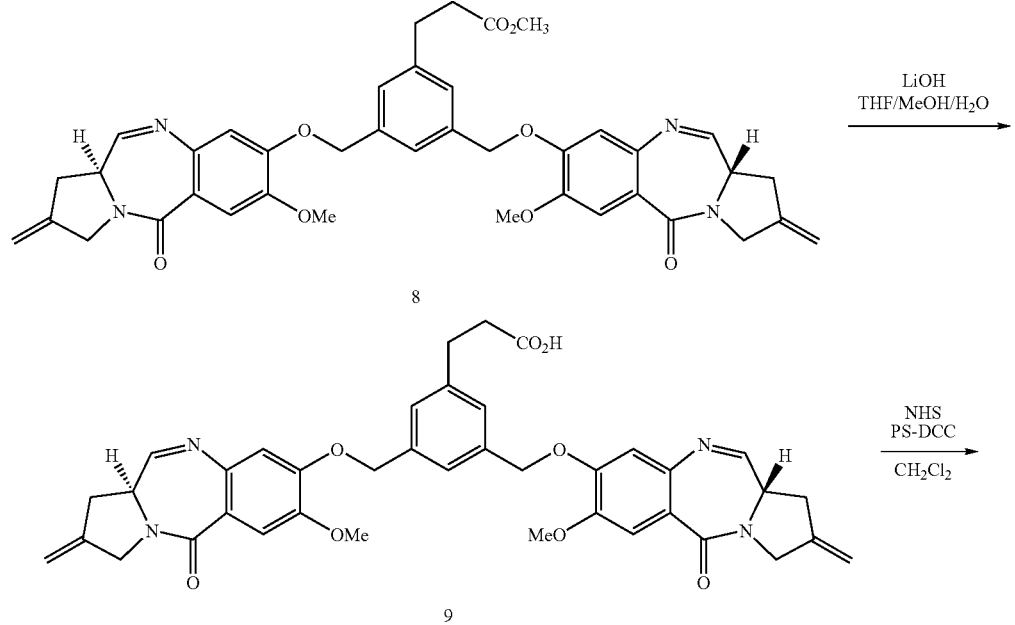

-continued

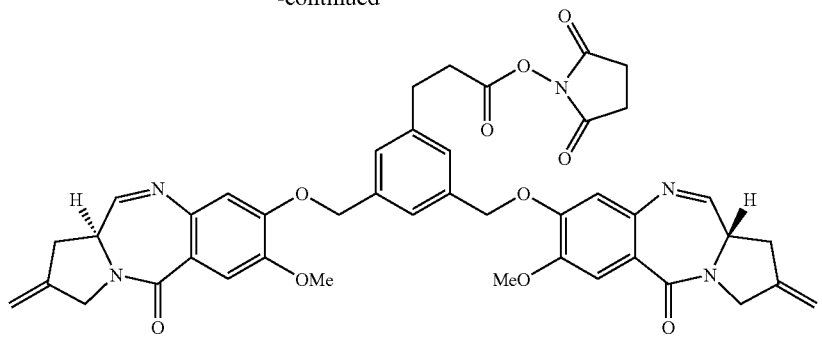

10

Compound 2: To a suspension of lithium aluminum hydride 2.19 g, 54.8 mmol) in anhydrous THF (50 mL) was added solution of dimethyl 5-bromoisophthalate (9.98 g, 36.5 mmol) in THF (100 mL) at 0° C. during 1 h period. After completion of addition, the mixture was stirred at it for 2 h. Upon that time, 150 mL of THF was added. The mixture was re-cooled to 0° C. and quenched with saturated aqueous NaCl. The white precipitate was filtered off, and the solid was further washed with extra THF (100 mL). Combined THF solution was dried with $Na_2SO_4$, filtered and concentrated. Further purification with silica gel flash chromatography (95:5 $CH_2Cl_2/CH_3OH$) provided 2 as a white solid (7.42 g, 95%).

Compound 3: compound 2 (3.36 g, 15.5 mmol) was suspended in anhydrous $CH_2Cl_2$ (31 mL). TBSCl (5.14 g, 34.1 mmol) was added, followed by imidazole (3.16 g, 46.5 mmol). The mixture was stirred at it for 1 h. The white precipitate was filtered off and the filtrate was concentrated with rotavapor. The resulting residue was purified by flash chromatography (silica gel, 97:3 hexanes/EtOAc) to give 3 as colorless oil (6.15 g, 89%): $^1$H NMR (400 MHz, $CDCl_3$) δ=0.081 (s, 12H), 0.92 (s, 18H), 4.67 (s, 4H), 7.18 (s, 1H), 7.31 (s, 2H).

Compound 4: A flask containing compound 3 (4.16 g, 9.36 mmol), methyl acrylate (1.3 mL, 14.0 mmol), $Pd(OAc)_2$ (105 mg, 0.47 mmol), P(o-tolyl)$_3$ (285 mg, 0.94 mmol) and $Et_3N$ (9 mL) in 19 mL $CH_3CN$ was heated to reflux under argon atmosphere for 16 h. After cooled to rt, ice $H_2O$ (20 mL) was added. The mixture was extracted with EtOAc (3×40 mL). The combined organic layers were washed with 1N HCl, brine, dried over $Na_2SO_4$, and concentrated. Further purification of the residue with flash chromatography (silica gel, 97:3 hexanes/EtOAc) to give 4 as colorless oil (3.91 g, 93%): $^1$HNMR (400 MHz, $CDCl_3$) δ 0.089 (s, 12H), 0.93 (s, 18H), 3.79 (s, 3H), 4.72 (s, 4H), 6.41 (d, J=16 Hz, 1H), 7.29 (s, 1H), 7.34 (s, 2H), 7.68 (d, J=16 Hz, 1H). EIMS m/z 473 ([M]$^+$+Na).

Compound 5: the mixture of 4 (2.54 g, 5.63 mmol) and Pd/C (563 mg) in 55 mL EtOAc was hydrogenated under atmospheric pressure for 30 min. The solution was then passed through celite, the solid was washed with extra EtOAc (25 mL). Combined EtOAc solutions were concentrated to provide 5 as colorless oil (2.55 g, 99+%), which is pure enough for the next step. $^1$HNMR (400 MHz, $CDCl_3$) δ=0.067 (s, 12H), 0.91 (s, 18H), 2.60 (t, J=8.0 Hz, 2H), 2.92 (t, J=8.0 Hz, 2H), 3.65 (s, 3H), 4.68 (s, 4H), 7.00 (s, 2H), 7.12 (s, 1H). EIMS m/z 475 ([M]$^+$+Na).

Compound 6: To a solution of 5 (1.48 g, 3.28 mmol) in anhydrous THF (33 mL) was added 8.2 mL of 1M solution of TBAF in THF at 0° C. After stirred at this temperature for 1 h, saturated aqueous $NH_4Cl$ (30 mL) was added to the mixture. The mixture was extracted with EtOAc (3×40 mL). Combined organic layers were washed with brine, dried over $Na_2SO_4$, and concentrated. Further purification of the residue with flash chromatography (silica gel, 95:5 $DCM/CH_3OH$) give 6 as colorless oil (625 mg, 85%), which solidified after standing in freezer. $^1$HNMR (400 MHz, $CDCl_3$) δ=2.59 (t, J=8.0 Hz, 2H), 2.91 (t, J=8.0 Hz, 2H), 3.63 (s, 3H), 4.61 (s, 4H), 7.08 (s, 2H), 7.16 (s, 1H).

Compound 7: The diol 6 (59 mg, 0.26 mmol) was dissolved in DCM (2.6 mL). The solution was cooled to 0° C., and treated with $Et_3N$ (82 μL, 0.58 mmol) and MsCl (46 μL, 0.58 mmol). The mixture was stirred at 0° C. for 30 min, and quenched with ice $H_2O$ (2 mL). The layers were separated and the aqueous layer was further extracted with DCM (3×2 mL). The combined DCM layers were washed with brine, dried with $Na_2SO_4$, and concentrated. Further dried under high vacuum pump provided 7 as pale yellow oil, which was used immediately to the next step without further purification.

Compound 8: To a mixture of PBD monomer (165 mg, 0.64 mmol) and 7 (assume to be 0.26 mmol) in DMF (2.7 mL) was added $K_2CO_3$ (147 mg, 1.06 mmol), KI (22 mg, 0.13 mmol) and $Bu_4NI$ (49 mg, 0.13 mmol) sequentially. The mixture was stirred under argon at rt for 7 h. Then DMF was removed with high vacuum. The residue was partitioned between DCM and water, and the layers were separated. The aqueous layer was further extracted with DCM (3×3 mL). Combined DCM layers were washed with brine, dried ($Na_2SO_4$), and concentrated. Purification of the residue with silica gel chromatography (25:1, $CH_2Cl_2/CH_3OH$) provided 8 as pale yellow glass-like solid (101 mg, 54%). EIMS m/z 763 ([M]$^+$+Na+2$H_2O$), 745 ([M]$^+$+Na+$H_2O$), 727 ([M]$^+$+Na).

Compound 9: To a stirred solution of methyl ester 8 (16 mg, 0.023 mmol) in THF-MeOH—$H_2O$ (3:1:1, 0.45 mL) was added 1 M aq. LiOH (0.025 mL, 1.1 eq.) at rt, and the reaction was monitored by TLC. After 3.5 h, the mixture was diluted with $H_2O$ (5 mL), and pH was adjusted to 2 with 1N HCl. The mixture was then extracted with DCM (3×5 mL). Combined DCM layers were washed with brine, dried over $Na_2SO_4$, and concentrated. Further purified by flash chromatography on silica gel (DCM:MeOH:AcOH=100:4:0.5) provided the desired acid 9 (8.2 mg, 60% brsm), EIMS m/z 749 ([M]$^+$+Na+2H$_2$O), 731 ([M]$^+$+Na+H$_2$O), 713 ([M]$^+$+Na); plus a small amount (~2 mg) of methyl ester 8.

Compound 10: To a solution of acid 9 (8.2 mg, 0.011 mmol) in CH$_2$Cl$_2$ (1 mL) were added poly-DCC (38 mg, 0.059 mmol) and N-hydroxysuccinimide (NHS) (2.7 mg, 0.024 mmol). The mixture was stirred at rt for 2 h, then filtered through a small bed of celite, washed with DCM, concentrated. The resulting residue was purified by flash chromatography (DCM:MeOH/100:3) to afford the desired product 10 (7 mg, 81%). EIMS m/z 874 ([M]$^+$+Na+2MeOH), 842 ([M]$^+$+Na+MeOH), 810 ([M]$^+$+Na).

Example 9

(2-{2-[2-(2-{3-[3,5-Bis-(7-methoxy-2-methylene-5-oxo-2,3,5,11a-tetrahydro-1H-benzo[e]pyrrolo[1,2-a][1,4]diazepin-8-yloxymethyl)-phenyl]-propoxy}-ethoxy)ethoxy]-ethoxy}-ethoxy)-acetic acid N-hydroxysuccinimidyl ester, compound 20

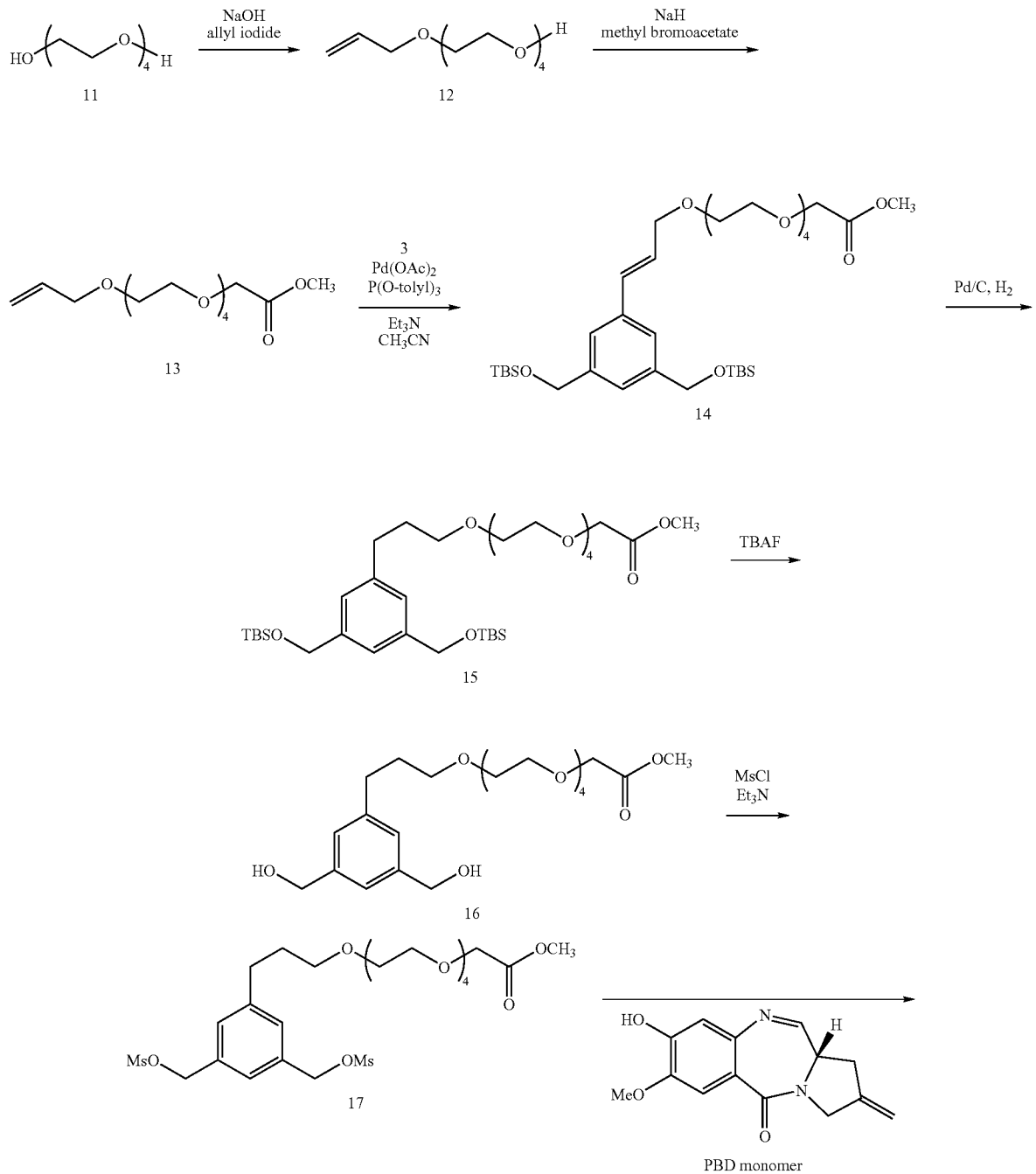

Scheme 3

PBD monomer

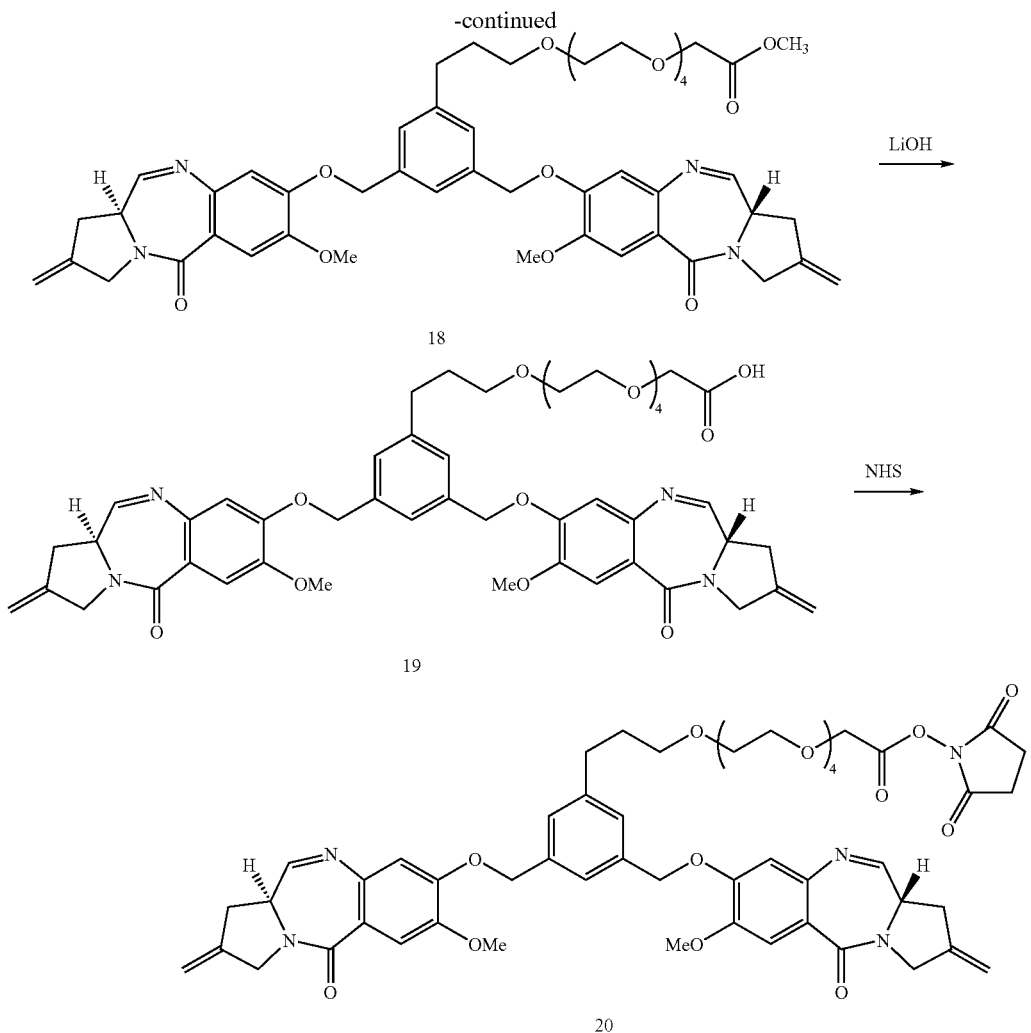

Compound 12: Aqueous NaOH (50%, 6.9 mL) was added to tetraethylene glycol (68.08 g, 350 mmol). The mixture was stirred at rt for 2 h, followed by addition of allyl iodide (8 mL, 87.6 mmol). After stirring for another 24 h, the mixture was partitioned between H$_2$O and EtOAc (50/50 mL). Aqueous layer was further extracted with EtOAc (5×30 mL). Combined EtOAc layers were dried over Na$_2$SO$_4$, and concentrated. Flash chromatography of the residue (silica gel, hexanes:EtOAc 4:6 to 0:1) provided 12 as colorless oil: $^1$H NMR (400 MHz, CDCl$_3$) δ=2.44 (br s, 1H), 3.63-3.71 (m, 16H), 3.99-4.01 (m, 2H), 5.13-5.17 (m, 1H), 5.22-5.27 (m, 1H), 5.84-5.92 (m, 1H); $^{13}$CNMR δ 61.8, 69.4, 70.4, 70.59, 70.61, 70.63, 72.2, 72.5, 117.0, 134.8. EIMS m/z 257 ([M]$^+$+Na).

Compound 13: To a suspension of NaH (89 mg, 2.2 mmol) in anhydrous THF (2.5 mL) was added solution of 12 (370 mg, 1.58 mmol) in THF (5 mL) at 0° C. under argon. The mixture was stirred at this temperature for 30 min, then rt for another 30 min. The mixture was re-cooled to 0° C., and methyl bromoacetate (0.29 mL, 3.16 mmol) was added dropwise. After stirring at 0° C. for 1 h, ice-bath was removed, and stirring was continued for another 24 h at rt. The reaction was filtered through celite and the filtrate was concentrated. Further purification of the residue with flash chromatography (silica gel, 1:1 hexanes/EtOAc) gave 13 as light yellow oil (220 mg): $^1$H NMR (400 MHz, CDCl$_3$) δ=3.57-3.74 (m, 19H), 3.98-4.0 (m, 2H), 4.26 (s, 2H), 5.15 (d, J=10.4 Hz, 1H), 5.24 (dd, J=16, 1.6 Hz, 1H), 5.84-5.93 (m, 1H); $^{13}$C NMR δ=51.7, 68.6, 69.4, 70.56, 70.60, 70.62, 70.9, 72.2, 117.0, 134.8, 170.9. EIMS m/z 329 ([M]$^+$+Na).

Compound 14: A flask containing compound 3 (1.30 g, 2.92 mmol), 13 (0.986 g, 3.220 mmol), Pd(OAc)$_2$ (33 mg, 0.15 mmol), P(o-tolyl)$_3$ (89 mg, 0.29 mmol) and Et$_3$N (2 mL) in 30 mL CH$_3$CN was heated to reflux under argon atmosphere for 12 h. After cooled to rt, the acetonitrile was removed by evaporation and ethyl acetate was added (40 ml) and the mixture was passed through celite, rinsed with ethyl acetate and concentrated. Further purification of the residue with flash chromatography (silica gel, 6:4 hexanes/EtOAc) to give 14 (1.02 g) as a colorless oil: $^1$H NMR (400 MHz, CDCl$_3$) δ=0.076 (s, 12H), 0.92 (s, 18H), 3.61-3.72 (m, 19H), 4.14 (s, 2H), 4.15-4.17 (m, 2H), 4.69 (s, 4H), 6.23-6.28 (m, 1H), 6.57 (d, J=16.0 Hz, 1H), 7.16 (s, 1H), 7.19 (s, 2H); $^{13}$C NMR δ=-5.2, 14.2, 18.4, 26.0, 51.7, 64.9, 68.6, 69.4, 70.57, 70.61, 70.64, 70.7, 70.9, 71.9, 122.8, 123.2, 125.9, 132.8, 136.5, 141.7, 170.9. EIMS m/z 693 ([M]$^+$+Na).

Compound 15: A mixture of 14 (0.062 g, 0.092 mmol) and Pd/C (9 mg) in 2.5 mL EtOAc was hydrogenated under atmospheric pressure for 30 min. The solution was then passed through celite, the solid was washed with extra EtOAc (10 mL). Combined EtOAc solutions were concentrated to provide 15 as colorless oil which was used without further purification. $^1$H NMR (400 MHz, CDCl$_3$) δ=0.072 (s, 12H), 0.92 (s, 18H), 1.87-1.89 (m, 2H), 2.64 (t, J=8.0 Hz, 2H), 3.43-3.70 (m, 21H), 4.14 (s, 2H), 4.68 (s, 4H), 6.98 (s, 2H), 7.10 (s, 1H). EIMS m/z 695 ([M]$^+$+Na).

Compound 16: To a solution of 15 from the previous step in anhydrous THF (1.8 mL) was added 0.23 mL of 1M solution of TBAF in THF at 0° C. After being stirred at this temperature for 1 h, saturated aqueous NH$_4$Cl (2 mL) was added to the mixture. The mixture was extracted with EtOAc (3×5 mL). Combined organic layers were washed with brine, dried over Na$_2$SO$_4$, and concentrated. Further purification of the residue with flash chromatography (silica gel, 95:5 CH$_2$Cl$_2$/CH$_3$OH) give 16 as colorless oil (27 mg, 85%). $^1$H NMR (400 MHz, CDCl$_3$) δ=1.86-1.89 (m, 2H), 2.66 (t, J=8.0 Hz, 2H), 3.40 (t, J=6.4 Hz, 2H), 3.50-3.70 (m, 19H), 4.10 (s, 2H), 4.61 (s, 4H), 7.09 (s, 2H), 7.13 (s, 1H). EIMS m/z 467 ([M]$^+$+Na).

Compound 17: The diol 16 (26.8 mg, 0.06 mmol) was dissolved in DCM (1.2 mL). The solution was cooled to 0° C., and treated with Et$_3$N (18.5 μL, 0.13 mmol) and MsCl (10.3 μL, 0.13 mmol). The mixture was stirred at 0° C. for 30 min, and quenched with ice H$_2$O (2 mL). The layers were separated and the aqueous layer was further extracted with DCM (3×2 mL). The combined DCM layers were washed with brine, dried with Na$_2$SO$_4$, and concentrated. Further dried under high vacuum pump provided 17 as pale yellow oil, which was used immediately for next step without further purification. EIMS m/z 623.1 ([M]$^+$+Na).

Compound 18: To a mixture of PBD monomer (40 mg, 0.15 mmol) and 17 from previous step in DMF (1.57 mL) was added K$_2$CO$_3$ (25 mg, 0.18 mmol), and KI (10 mg, 0.06 mmol) sequentially. The mixture was stirred under argon at rt for 20 h. Then DMF was removed with high vacuum. The residue was partitioned between DCM and water, and the layers were separated. The aqueous layer was further extracted with DCM (3×3 mL). Combined DCM layers were washed with brine, dried (Na$_2$SO$_4$) and concentrated. Purification of the residue with silica gel chromatography (25:1, DCM/CH$_3$OH) provided 18 as pale yellow glass-like solid. EIMS m/z 1011.5 ([M]$^+$+Na+2CH$_3$OH), 979.5 ([M]$^+$+Na+CH$_3$OH), 947.5 ([M]$^+$+Na).

Compound 19: To a stirred solution of methyl ester 18 (16 mg, 0.017 mmol) in THF-MeOH—H$_2$O (3:1:1, 0.7 mL) was added 1 M aq. LiOH (0.019 mL, 1.1 eq.) at rt, and the reaction was monitored by TLC (thin layer chromatography). After 5 h, the mixture was diluted with H$_2$O (5 mL), and pH was adjusted to 2 with 1N HCl. The mixture was then extracted with DCM (3×5 mL). Combined DCM layers were washed with brine, dried over Na$_2$SO$_4$, and concentrated. Further purified by flash chromatography on silica gel (DCM:MeOH:AcOH=100:4:0.5) provided the desired acid 19. EIMS m/z 933.4 ([M]$^+$+Na)

Compound 20: To a solution of acid 19 (5.9 mg, 0.006 mmol) in CH$_2$Cl$_2$ (1.0 mL) were added EDC (2 mg, 0.0097 mmol) and NHS (1.0 mg, 0.0084 mmol). The mixture was stirred at rt for 3 h, then filtered through a small bed of celite, washed with DCM and concentrated to afford the desired product 10 which was used as without further purification as the material was found to decompose upon silica purification. EIMS m/z 1030.4 ([M]$^+$+Na).

Example 10

(3-{2-[2-(2-{3-[3,5-Bis-(7-methoxy-2-methylene-5-oxo-2,3,5,11a-tetrahydro-1H-benzo[e]pyrrolo[1,2a][1,4]diazepin-8-yloxymethyl)-phenyl]-propoxy}-ethoxy)ethoxy]-ethoxy)-propionic acid N-hydroxysuccinimidyl ester, compound 31

Scheme 4

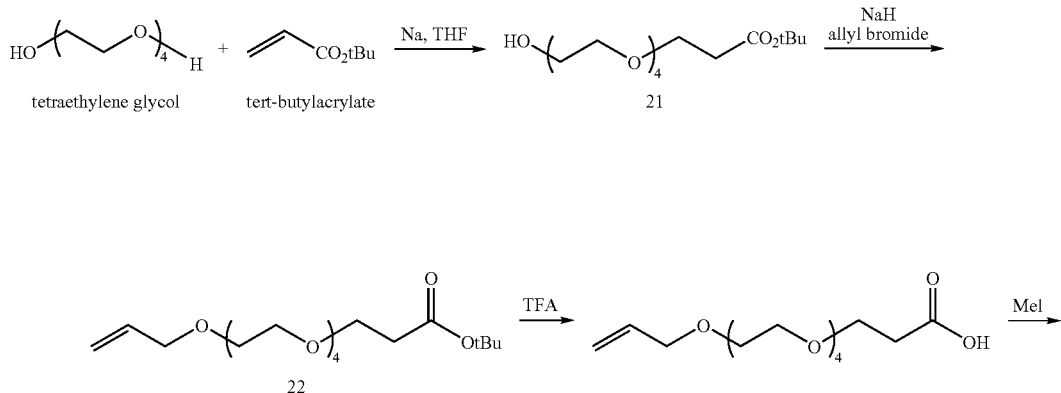

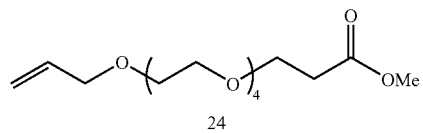

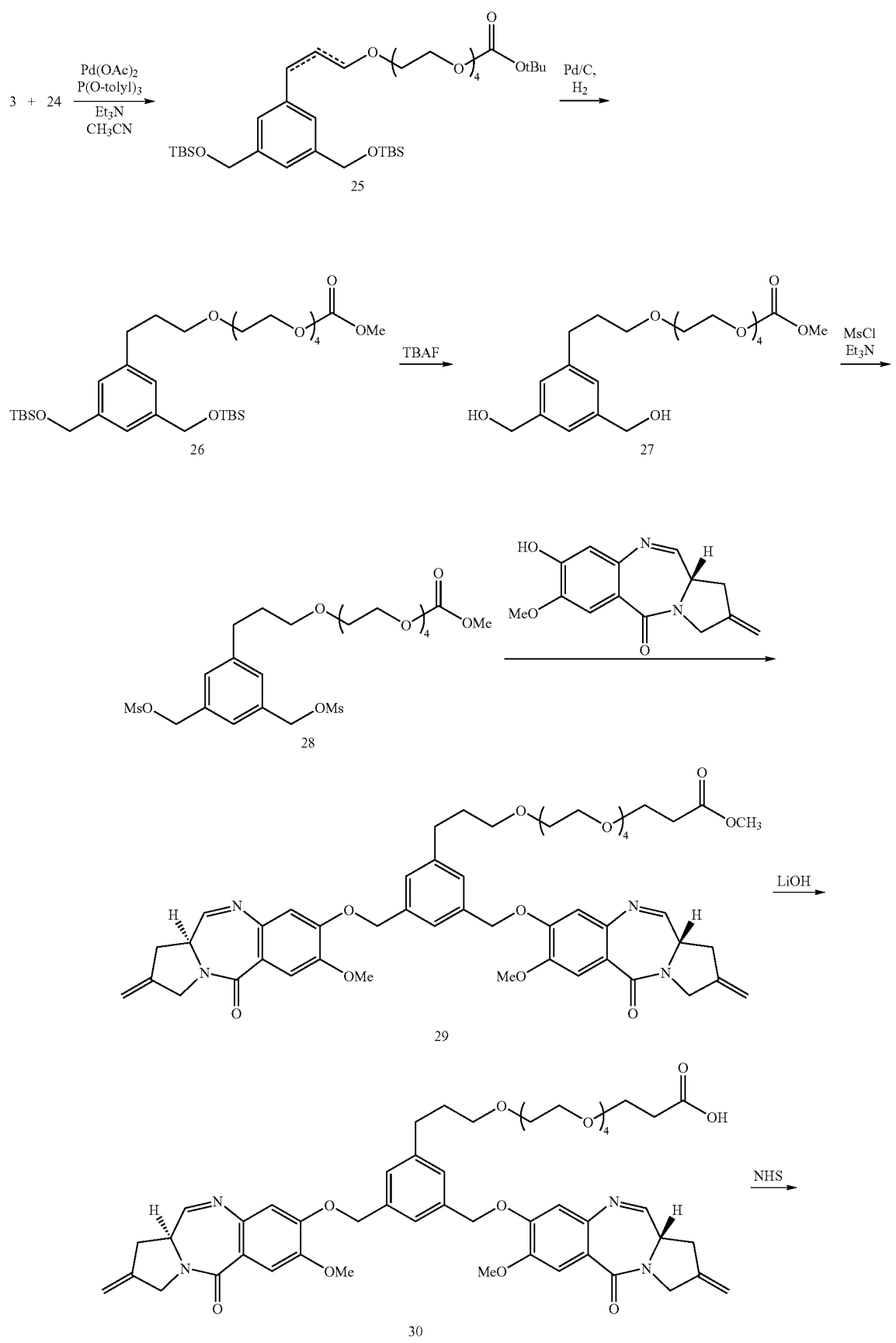

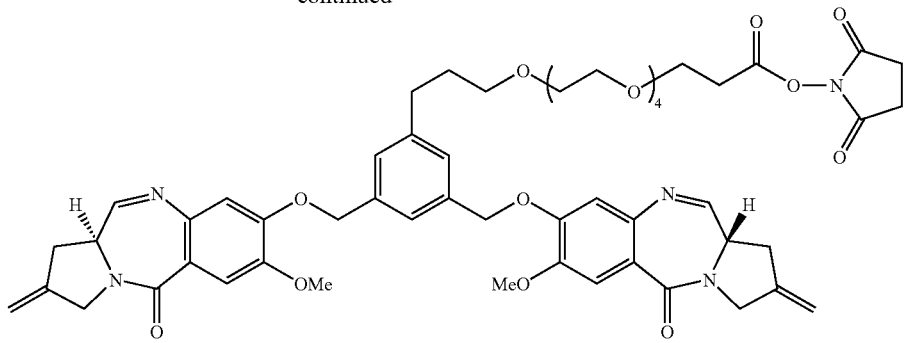

31

Compound 21: To a solution of tetraethylene glycol (162 mL, 940 mmol) in anhydrous THF (500 mL) was added sodium (215 mg, 9.4 mmol). When the sodium was dissolved, tert-butyl acrylate (45 mL, 310 mmol) was added. The mixture was stirred for 20 h at rt and neutralized with 8 mL 1N HCl. After removal of the solvent, the residue was partitioned between brine and EtOAc. The aqueous layer was further extracted with EtOAc. The combined organic layers were washed with brine, dried over $Na_2SO_4$, and concentrated. The resulting residue was purified by flash chromatography on silica gel (hexanes:ethyl acetate=4:6) providing the desired ester 21. $^1$H NMR (400 MHz, $CDCl_3$) δ=1.41 (s, 9H), 2.34 (br. S, 1H), 2.47 (t, J=6.4 Hz, 2H), 3.56-3.71 (m, 18H). EIMS m/z 345 ([M]$^+$+Na).

Compound 22: A solution of tetrabutylammonium hydrogenosulfate (1.27 g, 3.75 mmol) and NaOH (225 mg, 5.63 mmol) in $H_2O$ (7 mL) was added to a mixture of 21 (1.20 g, 3.75 mmol) and allylbromide (0.48 mL, 5.63 mmol) in DCM (14 mL). The two phase system was vigorously stirred for 45 min. The aqueous layer was separated and extracted three times with DCM. The combined DCM layers were concentrated. Addition of $Et_2O$ (15 mL) resulted in precipitating tetrabutylammonium bromide which was separated by filtration. The filtrate was washed with brine, dried over $Na_2SO_4$, and concentrated. Further purification of the residue with flash chromatography (silica gel, 1:1 hexanes/EtOAc) gave 22 as colorless oil. $^1$H NMR (400 MHz, $CDCl_3$) δ=1.42 (s, 9H), 2.47 (t, J=6.4 Hz, 2H), 3.56-3.70 (m, 18H), 4.00 (m, 2H), 5.15 (dq, J=6.0, 1.2 Hz, 1H), 5.25 (dq, J=16, 1.6 Hz, 1H), 5.84-5.94 (m, 1H). EIMS m/z 385.2 ([M]$^+$+Na).

Compound 23: A solution of compound 22 (478 mg, 1.32 mmol) in trifluoroacetic acid (9 mL) was stirred at it for 1.5 h upon that time all starting material was consumed. TFA was removed under vacuum and the residue was further dried with help of toluene. The crude product was used directly to the next step. $^1$H NMR (400 MHz, $CDCl_3$) δ=2.60 (t, J=6.0 Hz, 2H), 3.56-3.70 (m, 18H), 4.01 (d, J=5.6 Hz, 2H), 5.16 (dd, J=6.4, 1.2 Hz, 1H), 5.25 (dd, J=16, 1.6 Hz, 1H), 5.84-5.94 (m, 1H). EIMS m/z 329.2 ([M]$^+$+Na).

Compound 24: The solution of acid 23 in DMF (6.6 mL) was treated with $Cs_2CO_3$ (451 mg, 1.38 mmol) and MeI (90 μL, 1.45 mmol). The mixture was stirred at it for 2 h. DMF was then evaporated under high vacuum. The residue was suspended in EtOAc and the solid was filtered off. The filtrate was concentrated. Further purification of the residue with flash chromatography (silica gel, 97:3 hexanes/EtOAc) gave 24 as colorless oil. $^1$H NMR (400 MHz, $CDCl_3$) δ=2.58 (t, J=6.4 Hz, 2H), 3.56-3.70 (m, 18H), 4.00 (d, J=5.6 Hz, 2H), 5.14 (dd, J=6.4, 1.2 Hz, 1H), 5.24 (dd, J=16, 1.6 Hz, 1H), 5.84-5.94 (m, 1H). EIMS m/z 343.2 ([M]$^+$+Na).

Compound 25: A flask containing compound 3 (0.066 g, 0.15 mmol), 24 (0.05 g, 0.16 mmol), $Pd(OAc)_2$ (1.7 mg, 0.0074 mmol), P(o-tolyl)$_3$ (4.5 mg, 0.015 mmol) and $Et_3N$ (0.1 mL) in 3 mL $CH_3CN$ was heated to reflux under argon atmosphere for 8 h. After being cooled to rt, the acetonitrile was removed by evaporation and ethyl acetate was added (40 mL) and the mixture was passed through celite, rinsed with ethyl acetate. The combined organic layers were washed with brine, dried over sodium sulphate, and concentrated. Further purification of the residue with flash chromatography (silica gel, 6:4 hexanes/EtOAc) to give 25 as a colorless oil: $^1$H NMR (400 MHz, $CDCl_3$) δ=0.076 (s, 12H), 0.92 (s, 18H), 2.57 (t, J=6.4 Hz, 2H), 3.57-3.68 (m, 20H), 3.73 (t, J=6.4 Hz, 2H), 4.14 (d, J=6.0 Hz, 2H), 4.69 (s, 4H), 6.23-6.29 (m, 1H), 6.56 (d, J=16.0 Hz, 1H), 7.16 (s, 2H), 7.19 (s, 1H). EIMS m/z 707.4 ([M]$^+$+Na).

Compound 26: A mixture of 25 (0.216 g, 0.31 mmol) and Pd/C (32 mg) in 6.3 mL EtOAc was hydrogenated under atmospheric pressure for 30 min. The solution was then passed through celite, the solid was washed with extra EtOAc (10 mL). Combined EtOAc solutions were concentrated to provide 26 as colorless oil which was used without further purification. $^1$H NMR (400 MHz, $CDCl_3$) δ=0.071 (s, 12H), 0.91 (s, 18H), 1.87 (m, 2H), 2.58 (t, J=6.4 Hz, 2H), 2.64 (t, 2H), 3.44 (t, J=6.4 Hz, 2H), 3.54-3.67 (m, 20H), 3.72 (t, J=6.4 Hz, 2H), 4.68 (s, 4H), 6.98 (s, 2H), 7.10 (s, 1H). EIMS m/z 709.4 ([M]$^+$+Na).

Compound 27: To a solution of 26 from the previous step in anhydrous THF (3 mL) was added 0.38 mL of 1M solution of TBAF in THF at 0° C. After stirred at this temperature for 1 h, saturated aqueous $NH_4Cl$ (2 mL) was added to the mixture. The mixture was extracted with EtOAc (3×5 mL). Combined organic layers were washed with brine, dried over $Na_2SO_4$, and concentrated. Further purification of the residue with flash chromatography (silica gel, 95:5 $CH_2Cl_2/CH_3OH$) give 27 as colorless oil. $^1$H NMR (400 MHz, $CDCl_3$) δ=1.87 (m, 2H), 2.56 (t, J=6.4 Hz, 2H), 2.69 (t, J=7.2 Hz, 2H), 3.42 (t, J=6.4 Hz, 2H), 3.54-3.67 (m, 20H), 3.70 (t, J=6.4 Hz, 2H), 4.64 (s, 4H), 7.12 (s, 2H), 7.16 (s, 1H). EIMS m/z 481.3 ([M]$^+$+Na).

Compound 28: The diol 27 (54 mg, 0.126 mmol) was dissolved in DCM (2.4 mL). The solution was cooled to 0° C., and treated with $Et_3N$ (41 μL, 0.29 mmol) and MSCl (23 μL, 0.29 mmol). The mixture was stirred at 0° C. for 30 min, and quenched with ice $H_2O$ (2 mL). The layers were separated and the aqueous layer was further extracted with $CH_2Cl_2$ (3×2 mL). The combined DCM layers were washed with brine, dried with $Na_2SO_4$, and concentrated. Further dried under high vacuum pump provided 28 as pale yellow oil, which was used immediately to the next step without further purification. EIMS m/z 637.2 ($[M]^+$+Na).

Compound 29: To a mixture of PBD monomer (76 mg, 0.29 mmol) and 28 from previous step in DMF (2.9 mL) was added $K_2CO_3$ (49 mg, 0.35 mmol), and KI (20 mg, 0.12 mmol) sequentially. The mixture was stirred under argon at rt for 20 h. Then DMF was removed with high vacuum. The residue was partitioned between DCM and water, and the layers were separated. The aqueous layer was further extracted with DCM (3×3 mL). Combined DCM layers were washed with brine, dried ($Na_2SO_4$), and concentrated. Purification of the residue with silica gel chromatography (100:3, DCM/$CH_3OH$) provided 29 as pale yellow glass-like solid. EIMS m/z 1025.6 ($[M]^+$+Na+$2CH_3OH$), 993.5 ($[M]^+$+Na+$CH_3OH$), 961.5 ($[M]^+$+Na).

Compound 30: To a stirred solution of methyl ester 29 (11.8 mg, 0.012 mmol) in THF-MeOH—$H_2O$ (3:1:1, 0.5 mL) was added 1 M aq. LiOH (0.014 mL, 1.1 eq.) at rt, and the reaction was monitored by TLC. After 5 h, the mixture quenched with AcOH (0.014 mmol) and the volatiles were evaporated. Further purified by flash chromatography on silica gel (DCM:MeOH=95:5) provided the desired acid 30. EIMS m/z 947.5 ($[M]^+$+Na)

Compound 31: To a solution of acid 30 (4.6 mg, 0.005 mmol) in DCM (1.0 mL) were added EDC (1-ethyl-3-(3-dimethylaminopropyl)carbodiimide) as a coupling agent (1.4 mg, 0.0075 mmol) and NHS (0.74 mg, 0.0065 mmol). The mixture was stirred at rt overnight, then filtered through a small bed of celite, washed with DCM and concentrated to afford the desired product 31. Further purification by flash chromatography on silica gel (DCM:MeOH=100:3) provided the desired NHS ester 31. EIMS m/z 1022.5 ($[M]^+$+Na)

Example 11 huMy9-6—4-(3,5-Bis-[(S)-2-eth-(E)-ylidene-7-methoxy-1,2,3,11a-tetrahydro-pyrrolo[2,1c][1,4] benzodiazepin-5-one-8-yloxymethyl]-phenoxy)-butyryl conjugate 1.45 mL of a solution of huMy9-6 antibody at a concentration of 6.4 mg/mL in an aqueous buffer containing 0.05 M potassium phosphate and 0.05 M sodium chloride pH 8 is treated with a 7.5-fold molar excess of a 9.5 mM solution of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester from example 1 in dimethylacetamide (DMA) such that the final concentration of huMY9-6 is 5 mg/mL and concentration of DMA in the buffer is 20%. The reaction mixture is stirred at room temperature for 195 min., filtrated over Millex®-HV 0.45 μM (PVDF Durapore Millipore #SLHV013SL) and then loaded on to a Superdex™ 200 prep grade gel filtration column (Hiload™ 16/60 Column GE #17-1069-01) that has been previously equilibrated into an aqueous buffer containing 0.010 M phosphate, 0.140 M sodium chloride, pH 6.5. The conjugated antibody-containing fractions are collected, pooled and concentrated over Vivaspin 2 (10000 MWCO HY Sartorius #VS02H02) to yield product (1.8 mL). The final conjugate is assayed spectrophotometrically using the extinction coefficients that were determined for 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester ($\epsilon_{319nm}$=9087 $M^{-1}$ $cm^{-1}$ and $\epsilon_{280nm}$=12166 $M^{-1}$ $cm^{-1}$) and huMy9-6 antibody ($\epsilon_{280nm}$=206,539 $M^{-1}cm^{-1}$). An average of 2.1 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl moieties per molecule of antibody (1.6 mg/mL) were linked.

Example 12 huB4—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate 3.4 mL of a solution of huB4 antibody at a concentration of 8 mg/mL in an aqueous buffer containing 0.05 M potassium phosphate and 0.05 M sodium chloride pH 8 is treated with a 8-fold molar excess of a 11.5 mM solution of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid N-hydroxysuccinimidyl ester from example 1 in DMA such that the final concentration of huB4 is 5.6 mg/mL and concentration of DMA in the buffer is 20%. The reaction mixture is stirred at room temperature for 3 h., filtrated over Millex®-HV 0.45 μM (PVDF Durapore Millipore #SLHV013SL) and then loaded on to a Superdex™ 200 prep grade gel filtration column (Hiload™ 16/60 Column GE #17-1069-01) that has been previously equilibrated into an aqueous buffer containing 0.010 M phosphate, 0.140 M sodium chloride, pH 6.5. The conjugated antibody-containing fractions are collected, pooled and concentrated over Vivaspin 15R (10000 MWCO HY Sartorius #VS02H02) to yield product (5 mL). The final conjugate is assayed spectrophotometrically using the extinction coefficients that were determined for 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester ($\epsilon_{319nm}$=9087 $M^{-1}$ $cm^{-1}$ and $\epsilon_{280nm}$12166 $M^{-1}$ $cm^{-1}$) and huB4 antibody ($\epsilon_{280nm}$=222,960 $M^{-1}$ $cm^{-1}$). An average of 4.48 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl moieties per molecule of antibody (1.49 mg/mL) were linked.

Example 13 hu2H11—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate 3.45 mL of a solution of hu2H11 (see WO 2008/010101; registered by ATCC under the accession number PTA-7662)

antibody at a concentration of 5.1 mg/mL in an aqueous buffer containing 0.05 M potassium phosphate and 0.05 M sodium chloride pH 8 is treated with a 8-fold molar excess of a 10.5 mM solution of 4-(3,5-Bis-[(S)-2-eth-(E)-ylidene-7-methoxy-1,2,3,11a-tetrahydro-pyrrolo[2,1c][1,4]benzodiazepin-5-one-8-yloxy methyl]-phenoxy)-butyric acid N-hydroxysuccinimidyl ester from example 1 in DMA such that the final concentration of hu2H11 is 4.3 mg/mL and the concentration of DMA in the buffer is 20%. The reaction mixture is stirred at room temperature for 3 h, filtrated over Millex®-HV 0.45 µM (PVDF Durapore Millipore #SLHV013SL) and then loaded on to a Superdex™ 200 prep grade gel filtration column (Hiload™ 16/60 Column GE #17-1069-01) that has been previously equilibrated into an aqueous buffer containing 0.010 M phosphate, 0.140 M sodium chloride, pH 6.5. The conjugated antibody-containing fractions are collected, pooled and concentrated over Vivaspin 15R (10000 MWCO HY Sartorius #VS02H02) to yield product (2.2 mL). The final conjugate is assayed spectrophotometrically using the extinction coefficients that were determined for 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid methyl ester ($\epsilon_{319nm}$=9087 M$^{-1}$ cm$^{-1}$ and $\epsilon_{280nm}$=12166 M$^{-1}$ cm$^{-1}$) and hu2H11 antibody ($\epsilon$=208,380 M$^{-1}$cm$^{-1}$). An average of 3.74 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl moieties per molecule of antibody (1.55 mg/mL) were linked.

Example 14 huMy9-6—3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate 8.2 mL of a solution of huMy9-6 antibody at a concentration of 7.2 mg/mL in an aqueous buffer containing 0.05 M N-(2-hydroxyethyl)-piperazine-N'-2-ethanesulfonic acid (HEPES), 0.05 M sodium chloride and 2 mM ethylenediaminetetra-acetic acid (EDTA) pH 8 is treated with a 10-fold molar excess of a 10.4 mM solution of 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid N-hydroxysuccinimidyl ester from example 3 in DMA such that the final concentration of huMY9-6 is 3 mg/mL and concentration of DMA in the buffer is 20%. The reaction mixture is stirred at room temperature for 3 h, filtrated over Millex®-SV 5 µM (PVDF Durapore Millipore #SLSV025SL) and then loaded on to a Superdex™ 200 prep grade gel filtration column (Hiload™ 26/60 Column GE #17-1071-01) that has been previously equilibrated into an aqueous buffer containing 0.010 M phosphate, 0.140 M sodium chloride, pH 6.5. The conjugated antibody-containing fractions are collected, pooled and concentrated over Amicon Ultra-15 (Ultracel 10k Millipore #UFC901024) to yield product (7 mL). The final conjugate is assayed spectrophotometrically using the extinction coefficients that were determined for 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid methyl ester ($\epsilon_{319nm}$=7566 M$^{-1}$ cm$^{-1}$ and $\epsilon_{280nm}$=7078 M$^{-1}$ cm$^{-1}$) and huMy9-6 antibody ($\epsilon_{280nm}$=206,539 M$^{-1}$cm$^{-1}$). An average of 4.80 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl moieties per molecule of antibody (3.44 mg/mL) were linked.

Example 15 hu2H11—3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate 13.2 mL of a solution of hu2H11 antibody at a concentration of 4.7 mg/mL in an aqueous buffer containing 0.05 M N-(2-hydroxyethyl)-piperazine-N'-2-ethanesulfonic acid (HEPES), 0.05 M sodium chloride and 2 mM ethylenediaminetetra-acetic acid (EDTA) pH 8 is treated with glycofurol and a 10-fold molar excess of a 10.6 mM solution of 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid N-hydroxysuccinimidyl ester from example 3 in DMA such that the final concentration of hu2H11 is 3 mg/mL, concentration of glycofurol in the buffer is 10% and concentration of DMA in the buffer is 20%. The reaction mixture is stirred at room temperature for 3 h., filtrated over Millex®-SV 5 µM (PVDF Durapore Millipore #SLSV025SL) and then loaded on to a Superdex™ 200 prep grade gel filtration column (Hiload™ 26/60 Column GE #17-1071-01) that has been previously equilibrated into an aqueous buffer containing 0.010 M phosphate, 0.140 M sodium chloride, pH 6.5. The conjugated antibody-containing fractions are collected, pooled and concentrated over Amicon Ultra-15 (Ultracel 10k Millipore #UFC901024) to yield product (3.6 mL). The final conjugate is assayed spectrophotometrically using the extinction coefficients that were determined for 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid methyl ester ($\epsilon_{319nm}$=7566 M$^{-1}$ cm$^{-1}$ and $\epsilon_{280nm}$=7078 M$^{-1}$ cm$^{-1}$) and hu2H11 antibody ($E_{280nm}$=208,380 M$^{-1}$ cm$^{-1}$). An average of 4.08 3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl moieties per molecule of antibody (1.33 mg/mL) were linked.

Example 16 hu2H11—6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoyl conjugate 0.95 mL of a solution of hu2H11 antibody at a concentration of 3.2 mg/mL in an aqueous buffer containing 0.05 M potassium phosphate and 0.05 M sodium chloride pH 8 is treated with a 8-fold molar excess of a 10.5 mM solution of 6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid N-hydroxysuccinimidyl ester from example 4 in DMA such that the final concentration of hu2H11 is 2.5 mg/mL and the concentration of DMA in the buffer is 20%. The reaction mixture is stirred at room temperature for 4 h., filtrated over Millex®-HV 0.45 µM (PVDF Durapore Millipore #SLHV013SL) and then loaded on to a Superdex™ 200 prep grade gel filtration column (Hiload™ 16/60 Column GE #17-1069-01) that has been previously equilibrated into an aqueous buffer containing 0.010 M phosphate, 0.140 M sodium chloride, pH 6.5. The conjugated antibody-containing fractions are collected, pooled and concentrated over Amicon Ultra-4 (Ultracel 10k Millipore #UFC801096) to yield product (275 µL). The final conjugate is assayed spectrophotometrically using the extinction coefficients that were determined for 6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoic acid methyl ester ($\epsilon_{319}$=13594 M$^{-1}$ cm$^{-1}$ and $\epsilon_{280}$=19416 M$^{-1}$ cm$^{-1}$) and hu2H11 antibody ($\epsilon_{280nm}$=208,380 M$^{-1}$cm$^{-1}$). An average of 1.75 6-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenyl)-hex-5-ynoyl moieties per molecule of antibody (0.48 mg/mL) were linked.

Example 17

IGP-08-NHS Stock Solution Preparation

Solutions of IGP-08-NHS (compound 10 of ex. 8) are made fresh to a 0.005 M stock based on a molecular weight of 787.81 in DMA. The stock solution is assayed spectrophotometrically using a reference extinction coefficient determined at 320 nm ($\epsilon_{320}$=9137 M$^{-1}$ cm$^{-1}$).

Example 18 huMy9-6-IGP-08 huMy9-6 antibody that binds to the CD33 antigen is selected for conjugation of PBD derivatives. A solution of huMy9-6 antibody at a concentration of 5 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8 is treated with a 6-fold molar excess of a solution of IGP-08-NHS (compound 10 of example 8) in DMA such that the final concentration of DMA in the buffer is 20%. The reaction mixture is stirred at room temperature for 120 min. and then loaded on to a Sephadex G25 gel filtration column (HiPrep™ 26/10 Desalting Column GE #17-5087-01) that has been previously equilibrated into an aqueous buffer containing 0.01 M sodium citrate, 0.135 M sodium chloride, pH 5.5. The conjugated antibody-containing fractions are collected and pooled to yield product. The pooled sample is dialyzed overnight against the same elution buffer (0.01 M sodium citrate, 0.135 M sodium chloride, pH 5.5) to further purify the product. The final conjugate is assayed spectrophotometrically using the extinction coefficients that were determined for compound 8 of example 8 ($\epsilon_{320}$=9137 M$^{-1}$ cm$^{-1}$ and $\epsilon_{280}$=7743 M$^{-1}$ cm$^{-1}$) and huMy9-6 antibody ($\epsilon_{280}$=206,460 M$^{-1}$cm$^{-1}$). An average of 4.5 PBD molecules (Compound 9 of example 8) per molecule of antibody were linked.

Example 19 huB4-IGP-08

Hu-Anti-B4 antibody that binds to the CD19 antigen preferentially expressed on the surface of human lymphoma cells is selected for conjugation of PBD derivatives. A solution of huB4 antibody at a concentration of 8 mg/mL in an aqueous buffer containing 0.05 M potassium phosphate, 0.05 M sodium chloride and 2 mM ethylenediaminetetra-acetic acid (EDTA), pH 7.1 is treated with a 5-fold molar excess of a solution of IGP-08-NHS (compound 10 of example 8) in dimethylacetamide (DMA) such that the final concentration of DMA in the buffer is 20%. The reaction mixture is stirred at room temperature for 70 min. and then loaded on to a Sephadex G25 gel filtration column (NAP™ Columns, GE #17-0852-02) that has been previously equilibrated into an aqueous buffer containing 0.010 M phosphate, 0.140 M sodium chloride, pH 6.5. The conjugated antibody-containing fractions are collected and pooled to yield product. The pooled sample is dialyzed overnight against the same elution buffer (0.010 M phosphate, 0.140 M sodium chloride, pH 6.5) to further purify the product. The final conjugate is assayed spectrophotometrically using the extinction coefficients that were determined for compound 8 of ex. 8 ($\epsilon_{320}$=9137 M$^{-1}$ cm$^{-1}$ and $\epsilon_{280}$=7743 M$^{-1}$ cm$^{-1}$) and huB4 antibody ($\epsilon_{280nm}$=222,960 M$^{-1}$cm$^{-1}$). An average of 3.1 PBD molecules (Compound 9 of example 8) per molecule of antibody were linked.

Example 20

IGP-13-NHS Stock Solution Preparation

Solutions of IGP-13-NHS (compound 31 of example 10) are made fresh to a 0.0062 M stock based on a molecular weight of 1022.1 in DMA. The stock solution is assayed spectrophotometrically using a reference extinction coefficient determined at 320 nm ($\epsilon_{320}$=9137 M$^{-1}$ cm$^{-1}$).

Example 21 hu2H11-IGP-13

Hu2H11 antibody that binds to the EpCAM antigen is selected for conjugation of PBD derivatives. A solution of hu2H11 antibody at a concentration of 5 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8 is treated with a 8-fold molar excess of a solution of IGP-13-NHS (compound 31 of example 10) in DMA such that the final concentration of DMA in the buffer is 15%. The reaction mixture is stirred at room temperature for 120 min. and then loaded on to a Sephadex G25 gel filtration column (HiPrep™ 26/10 Desalting Column GE #17-5087-01) that has been previously equilibrated into an aqueous buffer containing 0.01 M sodium citrate, 0.135 M sodium chloride, pH 5.5. The conjugated antibody-containing fractions are collected and pooled to yield product. The pooled sample is dialyzed overnight against the same elution buffer (0.01 M sodium citrate, 0.135 M sodium chloride, pH 5.5) to further purify the product. The final conjugate is assayed spectrophotometrically using the extinction coefficients that were determined for compound 29 of example 10 ($\epsilon_{320}$=9137 $M^{-1}$ $cm^{-1}$ and $\epsilon_{280}$=7743 $M^{-1}$ $cm^{-1}$) and hu2H11 antibody ($\epsilon_{280nm}$=215,525 $M^{-1}cm^{-1}$). An average of 4.7 PBD molecules (Compound 31 of example 10) per molecule of antibody were linked.

Example 22

Binding Assay

The relative binding affinities of the anti-B4 antibody and its tomaymycin conjugate on antigen-expressing Ramos cells is determined using a fluorescence-based assay. The antibody-tomaymycin conjugate and naked antibody at starting concentrations of 1 a $10^{-7}$ M are added to 96-well round bottom plates and titrated using 3-fold serial dilutions so that there are duplicates for each concentration. Ramos cells are added at 50,000 cells per well to each well containing various concentrations of the antibody or conjugate, as well as to control wells. The plates are incubated on ice for 3 hours. After the incubation period, the cells in the plate are washed, and a fluorescence labeled secondary antibody that binds to a humanized IgG, like anti-B4, is added, and the plates are incubated for 1 hour on ice. The plates are washed again after the incubation period, and the cells are fixed with 1% formaldehyde/PBS solution. The fluorescence in each well of the plates is read using a Becton Dickinson FACSCalibur fluorescence analyzer. Data are plotted as a percent of the maximum fluorescence obtained at the highest concentration of antibody or conjugate.

Example 23

In Vitro Potency and Specificity of Tomaymycin Derivative or Tomaymycin Derivative Conjugates (Viability Assay)

General Protocol to be Used

Samples of free tomaymycin derivative or tomaymycin derivative conjugate are added to a 96-well flat bottomed tissue culture plate and titrated using serial dilutions ranging from $1\times10^{-12}$ M to $3\times10^{-7}$ M. Antigen positive tumor cells or antigen negative tumor cells are added to the wells in such a way that there are triplicate samples for each drug concentration for each cell line. The plates are incubated at 37° C. in an atmosphere of 5% $CO_2$ for 4 days.

At the end of the incubation period, 20 μl of the tetrazolium reagent WST-8 (2-(2-methoxy-nitrophenyl)-3-(4-nitrophenyl)-5-(2,4-disulfophenyl)-2-tetrazolium, monosodium salt) is added to each well, and the plates are returned to the incubator for 2 hours. The absorbance in each well of the plates is then measured using the Molecular Devices plate reader at 450 nm. Surviving fraction of cells at each concentration of tomaymycin derivative or conjugate are plotted.

Figure 2:
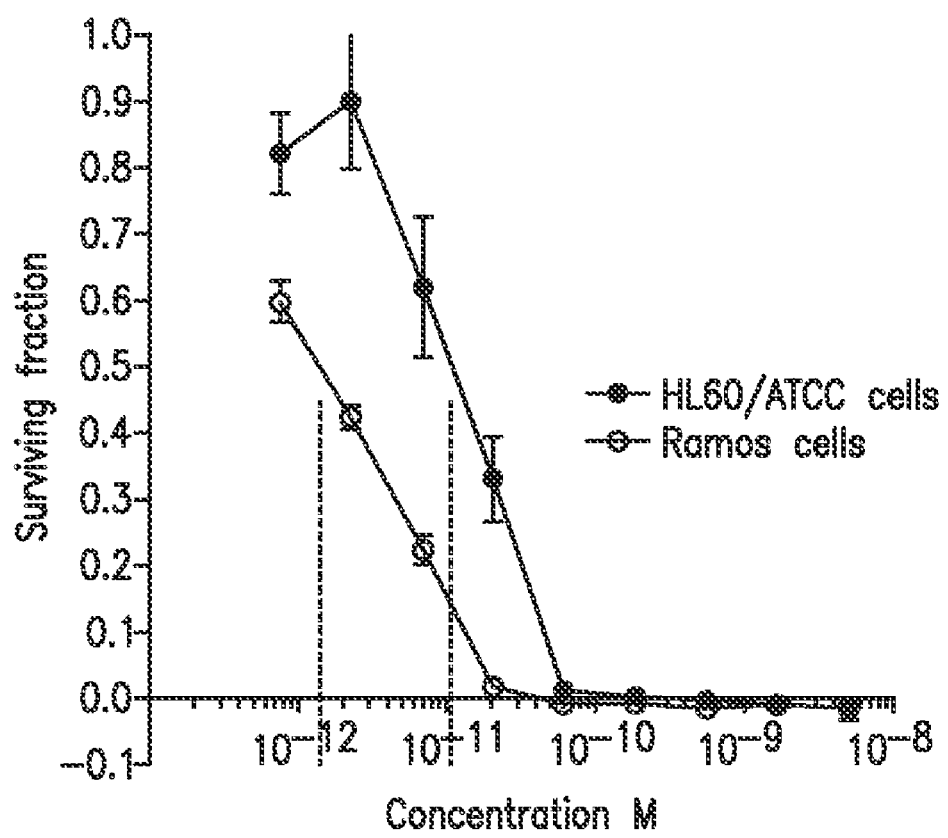
FIG. 2: In vitro cytotoxicity of 4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid methyl ester of ex. 2.
Figure 3:
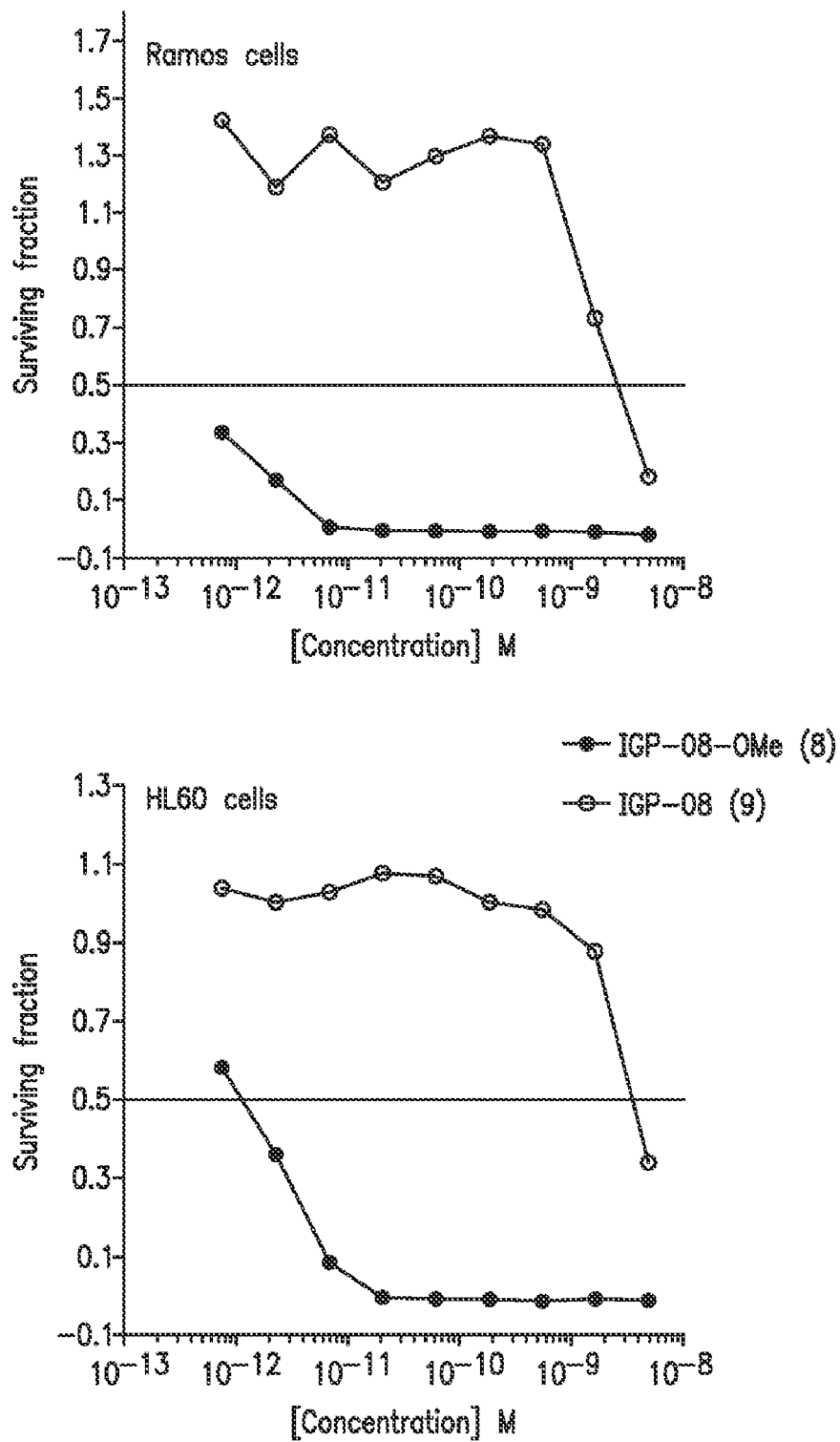
FIG. 3: In vitro cytotoxicity potency of compounds 8 (IGP08) and 9 (IGP08-OMe) of ex. 8, showing higher potency for ester IGP08-OMe than for acid IGP08.
Figure 4:
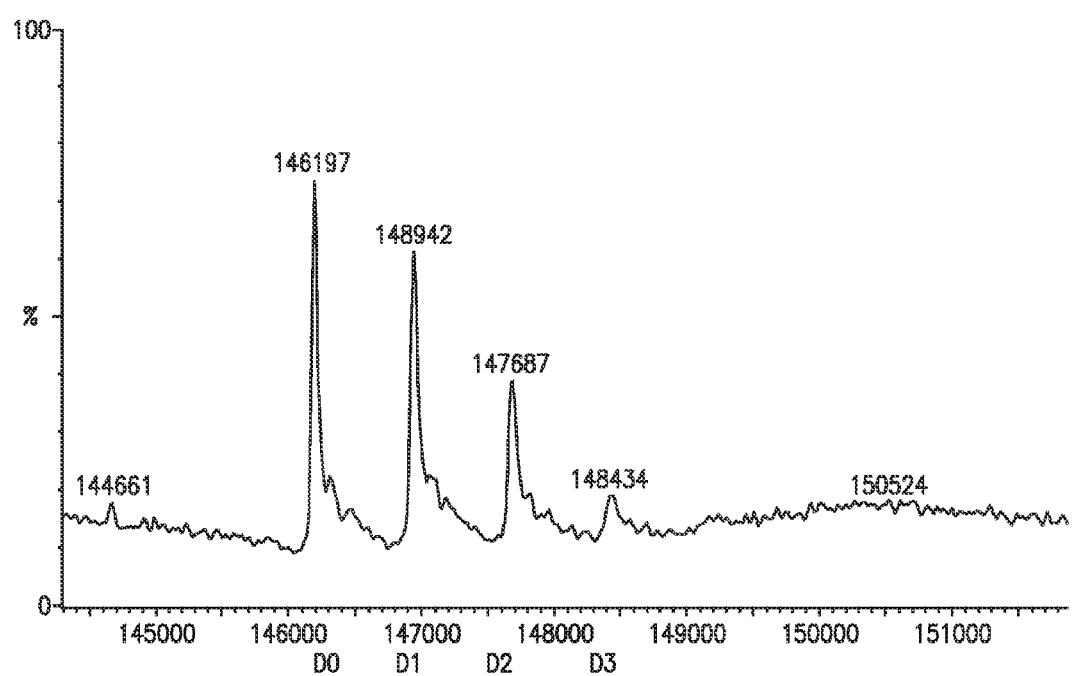
FIG. 4; Represents the Mass Spectral analysis of deglycosylated huMy9-6—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate (having 2.1 Drug/Ab by UV that is 2.1 tomaymicine derivative par 1 antibody as determined by UV) of ex. 11.
Figure 5:
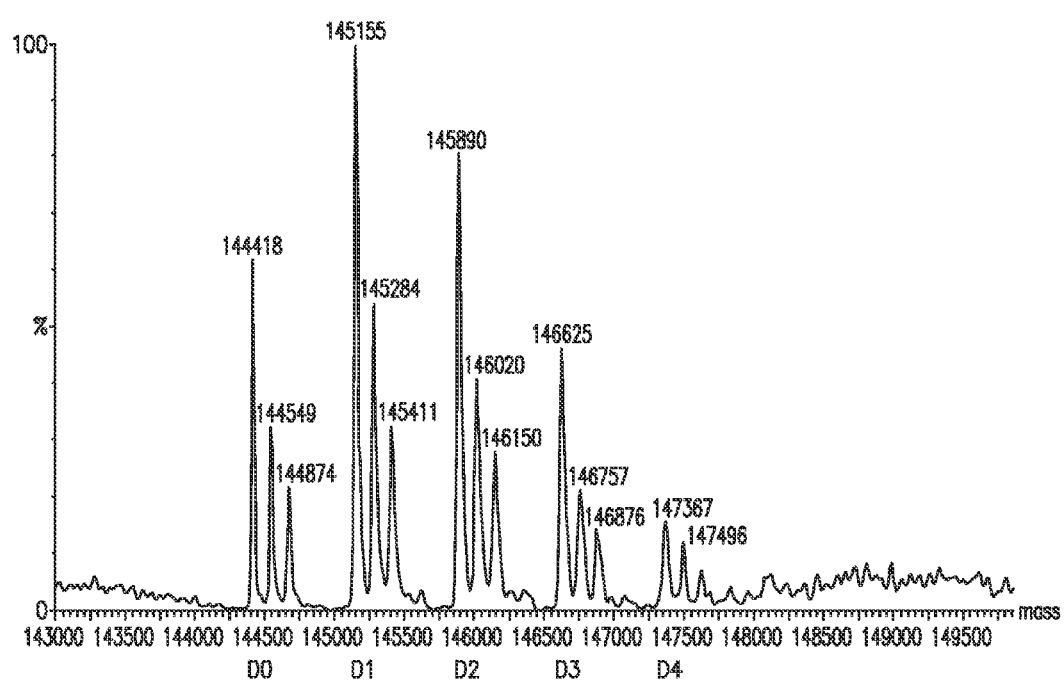
FIG. 5: Mass Spectral analysis of deglycosylated huB4—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate (4.48 Drug/Ab by UV) of ex. 12.
Figure 6:
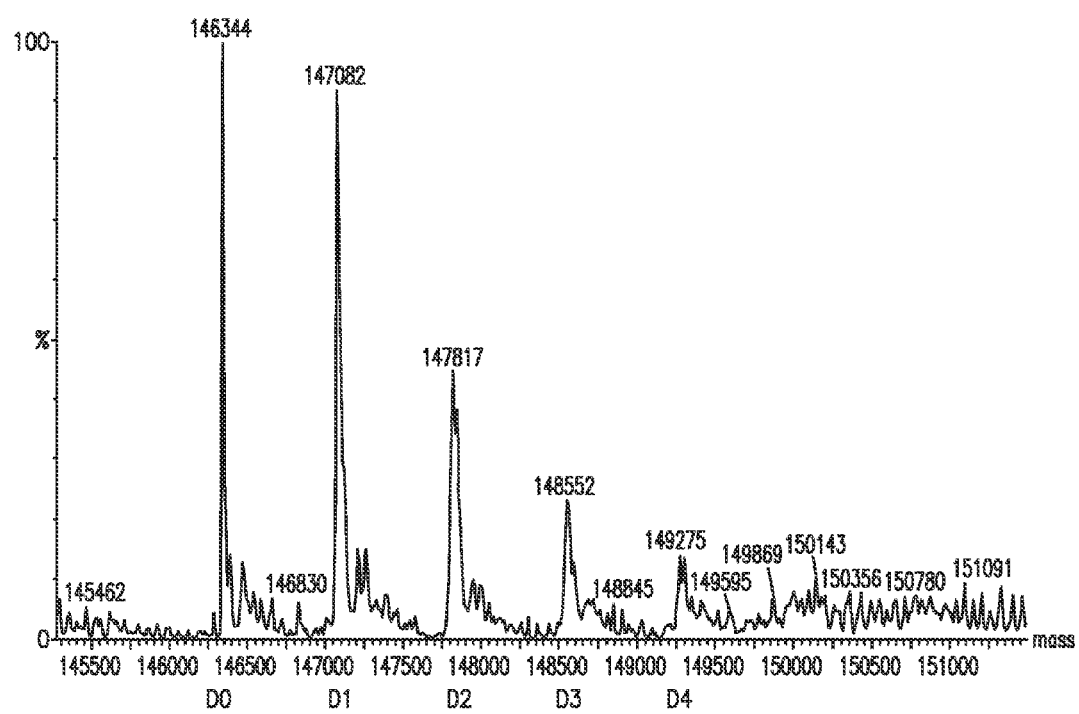
FIG. 6: MS analysis of deglycosylated hu2H11—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate (3.74 Drug/Ab by UV) of ex. 13.
Figure 7:
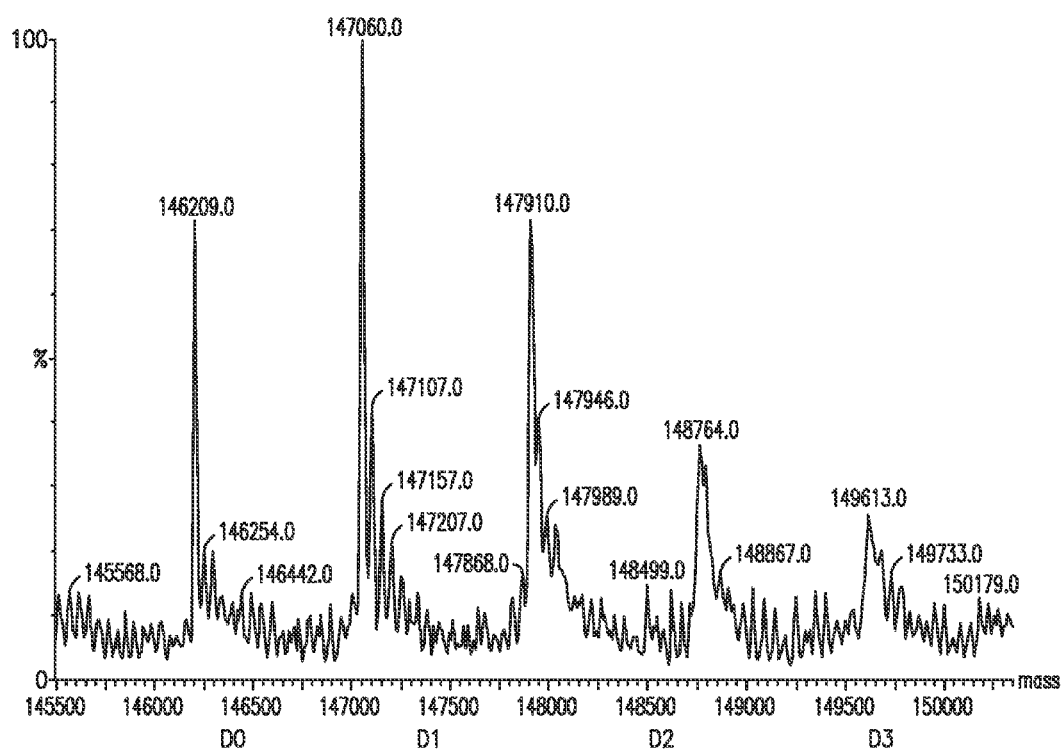
FIG. 7: MS analysis of huMy9-6—3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate (4.8 Drug/Ab by UV) of ex. 14.
Figure 8:
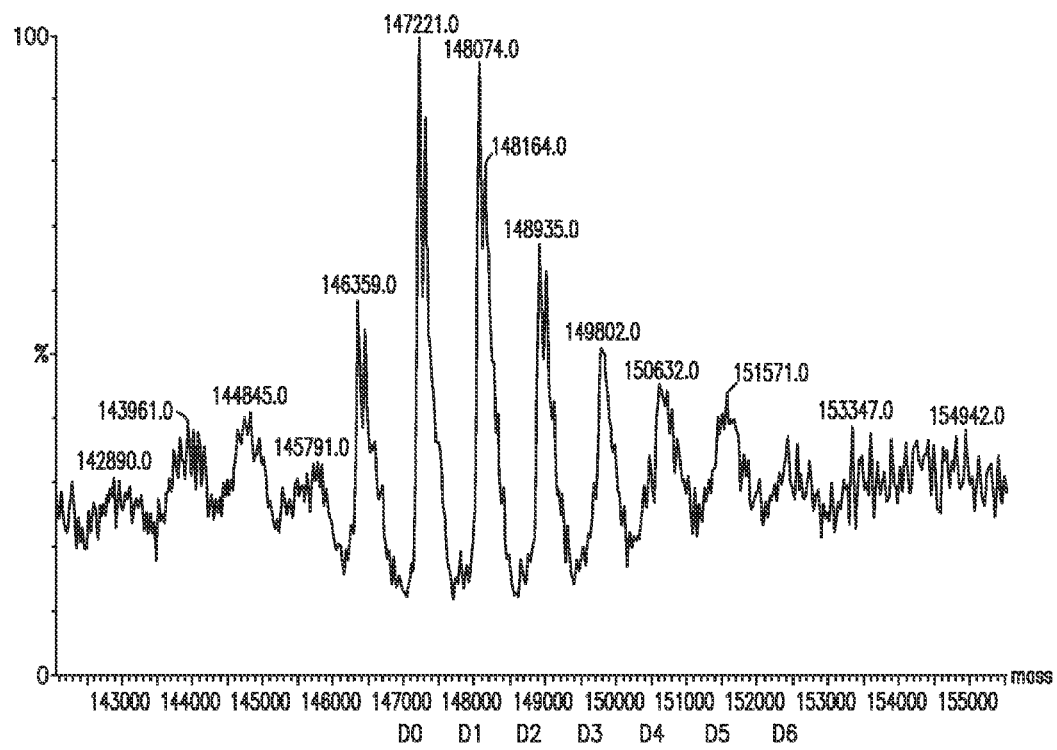
FIG. 8: MS analysis of hu2H11—3-(2-{2-[2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate (4.08 Drug/Ab by UV) of ex. 15.
Figure 9:
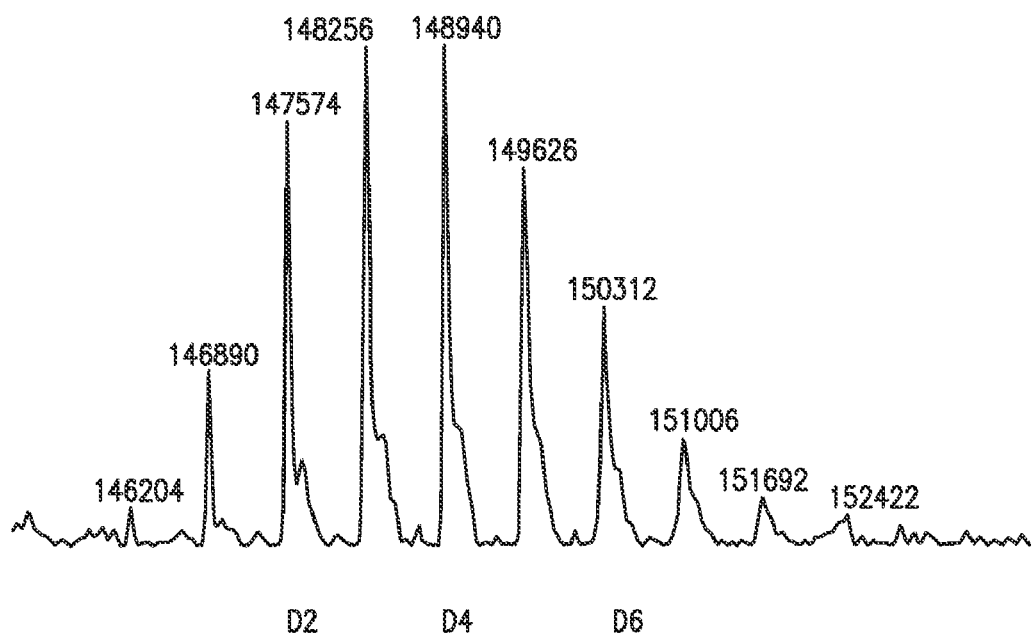
FIG. 9: MS analysis of deglycosylated huMy9-6-IGP08 (compound of ex. 18)
Figure 10:
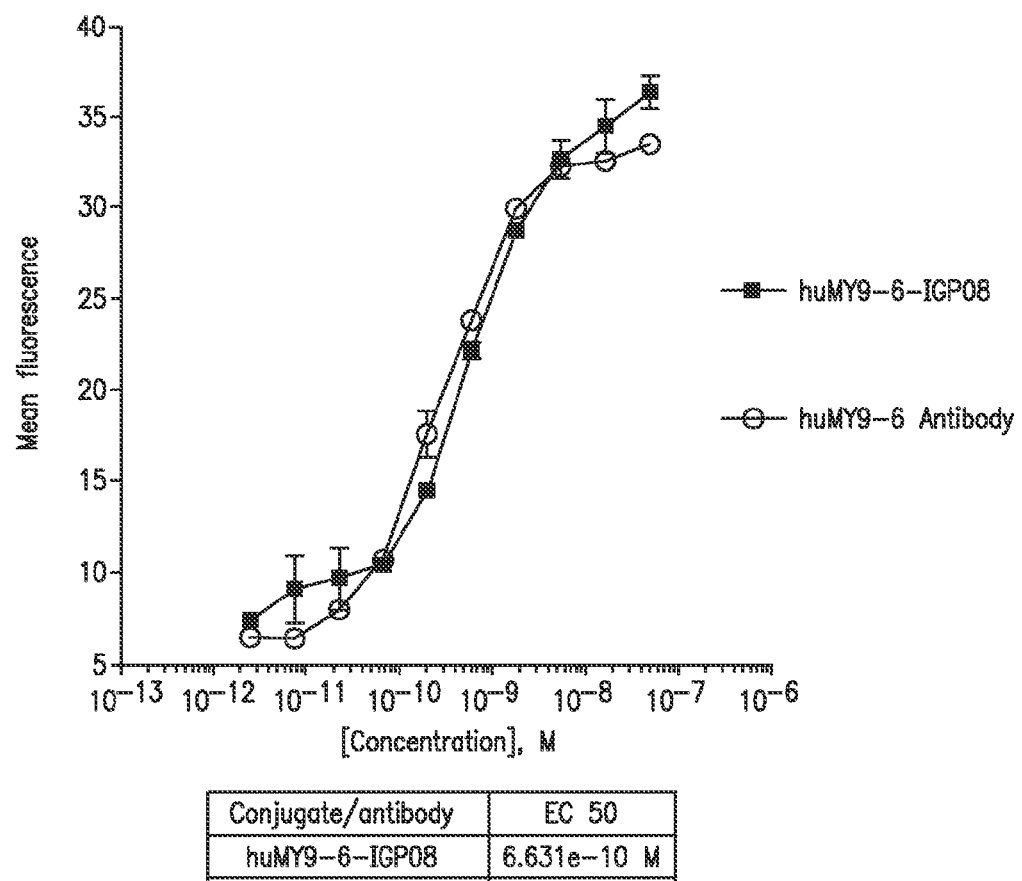
FIG. 10: Comparative binding properties of naked huMy9-6 and huMy9-6-IGP08 (compound of ex. 18) to the antigen CD33.
Figure 11:
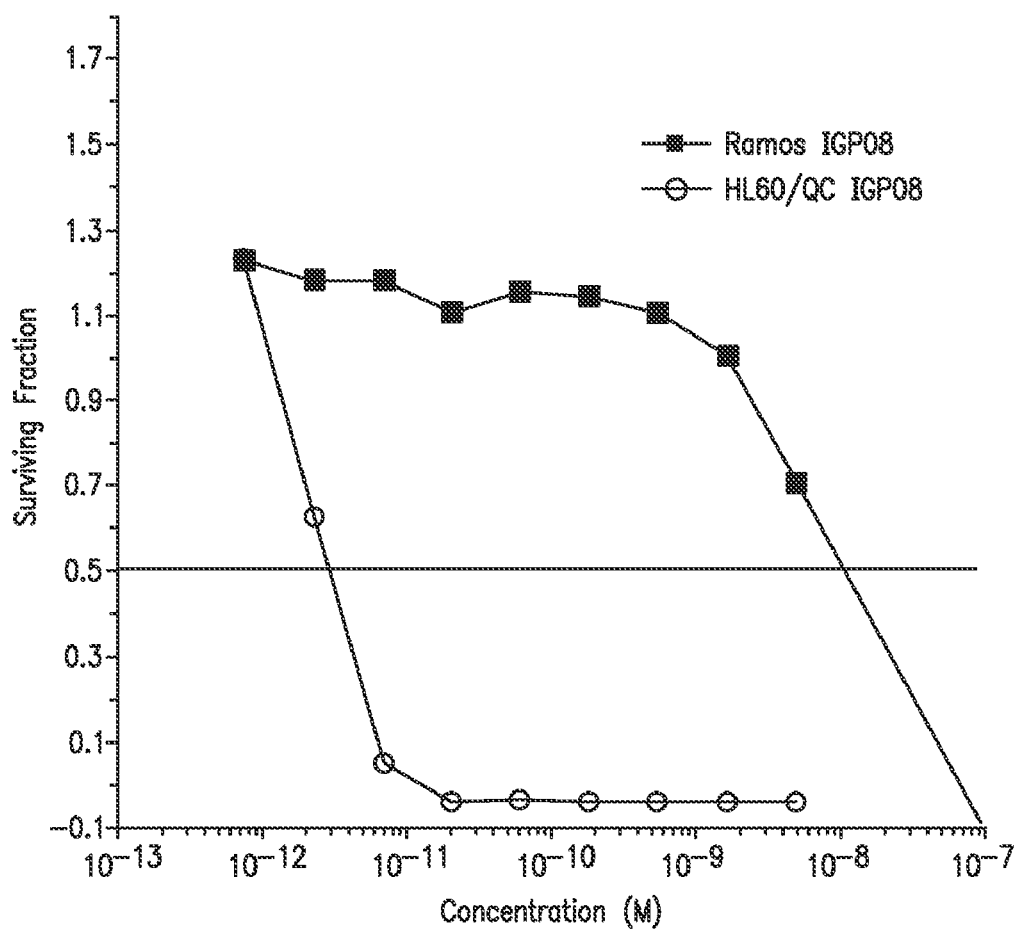
FIG. 11: In vitro cytotoxicity potency of My9-6-IGP08 (compound of ex. 18) versus Ramos (Ag−) and HL60/QC (Ag+) cells.
Figure 12:
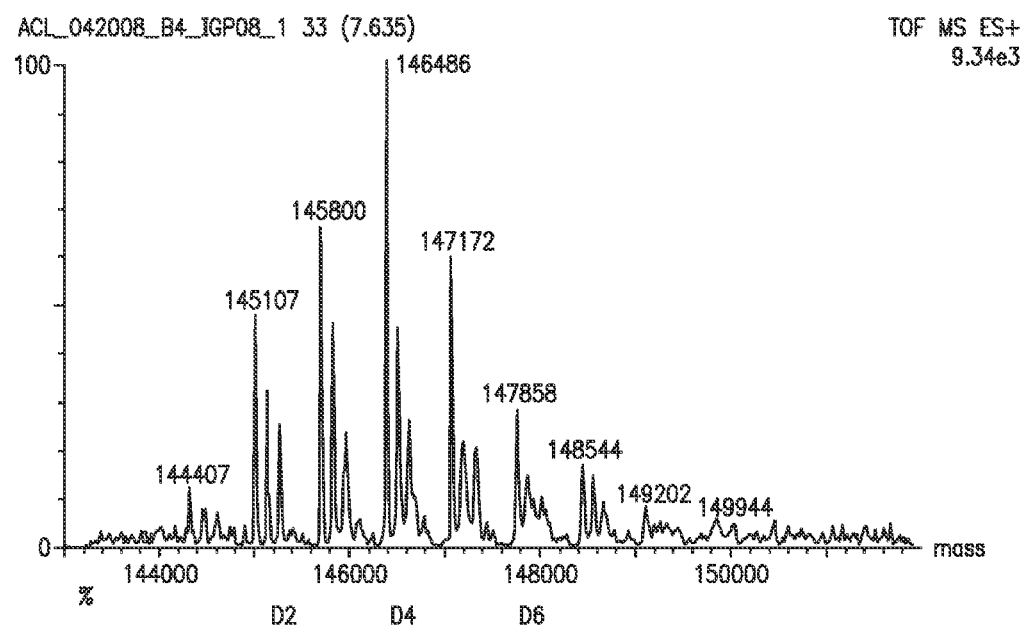
FIG. 12: MS analysis of deglycosylated huB4-IGP08 (3.1 Drug/Ab by UV) of ex. 19)
Figure 13:
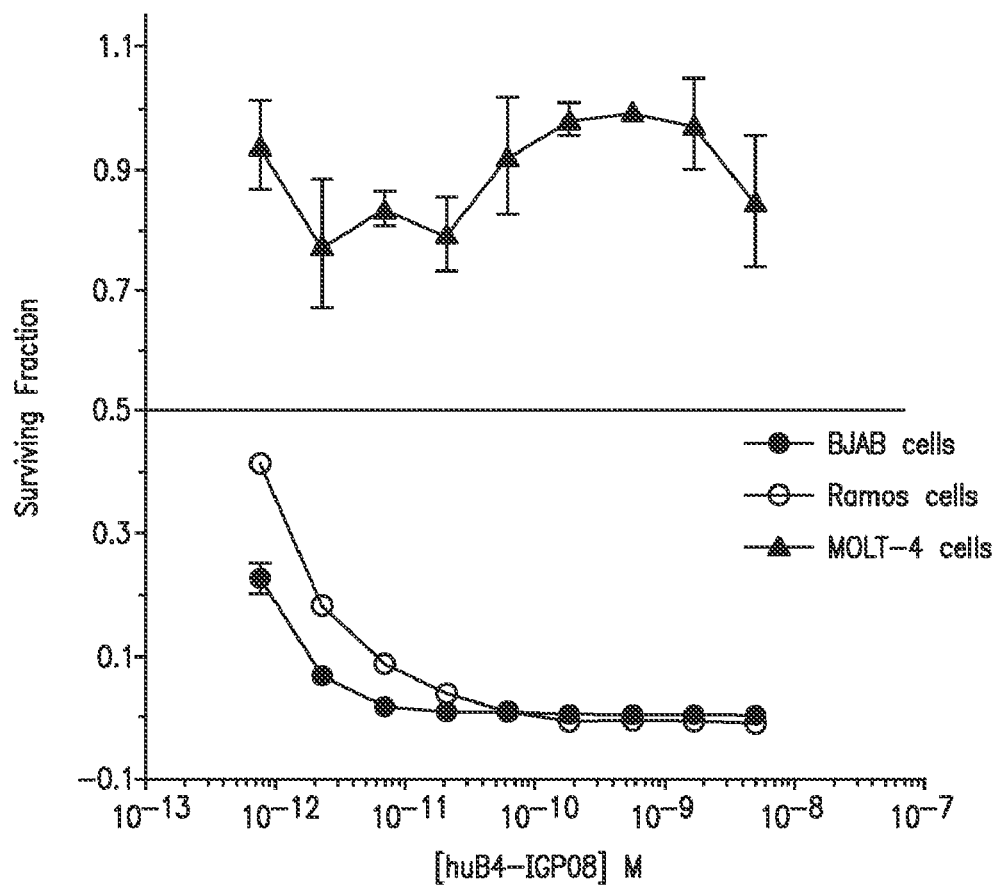
FIG. 13: Cytotoxicity properties of huB4-IGP08 (compound of ex. 19) versus BJAB (Ag+), Ramos (Ag+) and MOLT-4 (Ag−) cells [~IC50's: BJAB cells<7.6e-13 M: Ramos cells<7.6e-13 M: MOLT-4 cells>5.0e-9 M]
Figure 14:
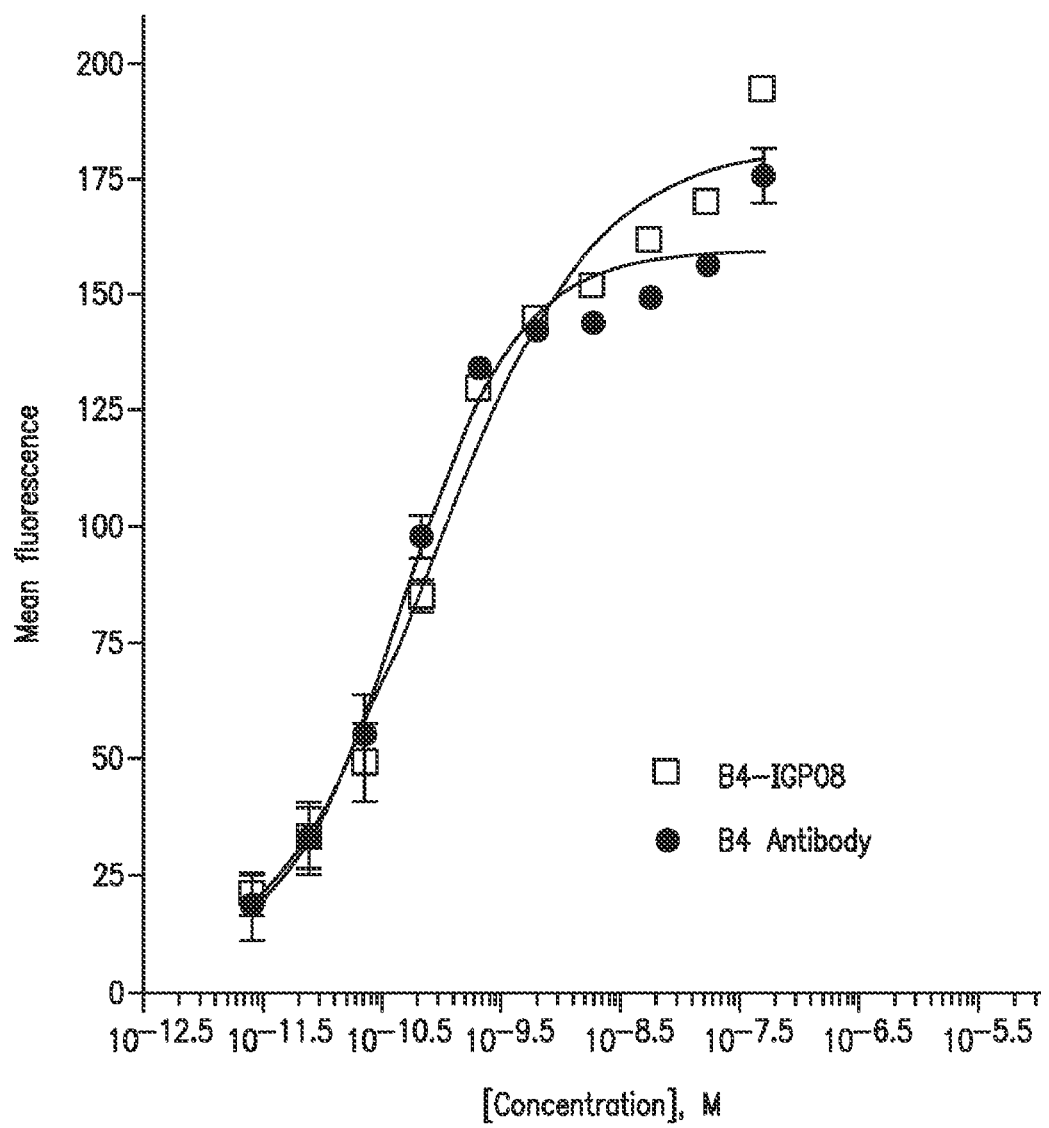
FIG. 14: Comparative binding properties of naked huB4 and huB4-IGP08 (compound of ex. 19)
Figure 15:
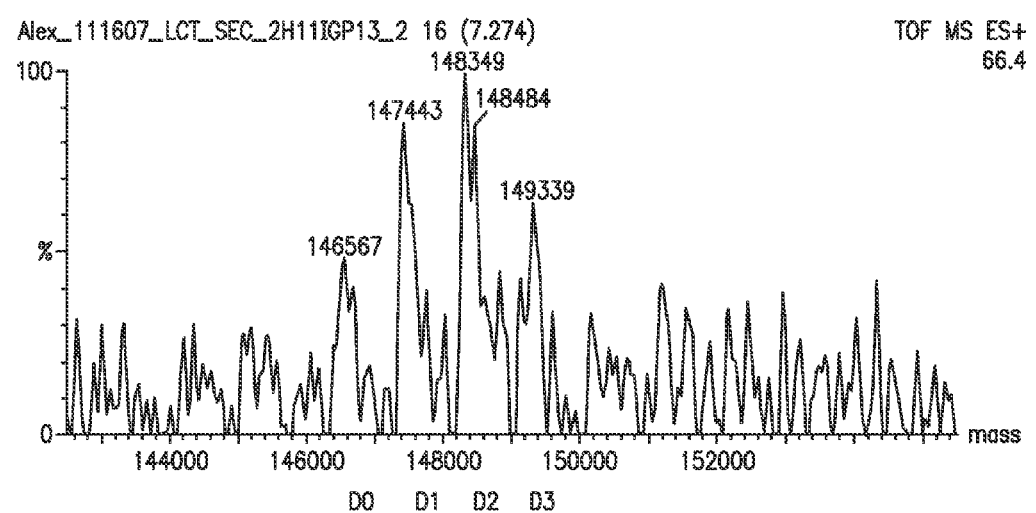
FIG. 15: MS analysis of deglycosylated hu2H11-IGP13 (4.7 Drug/Ab by UV) of ex. 21.
Figure 16:
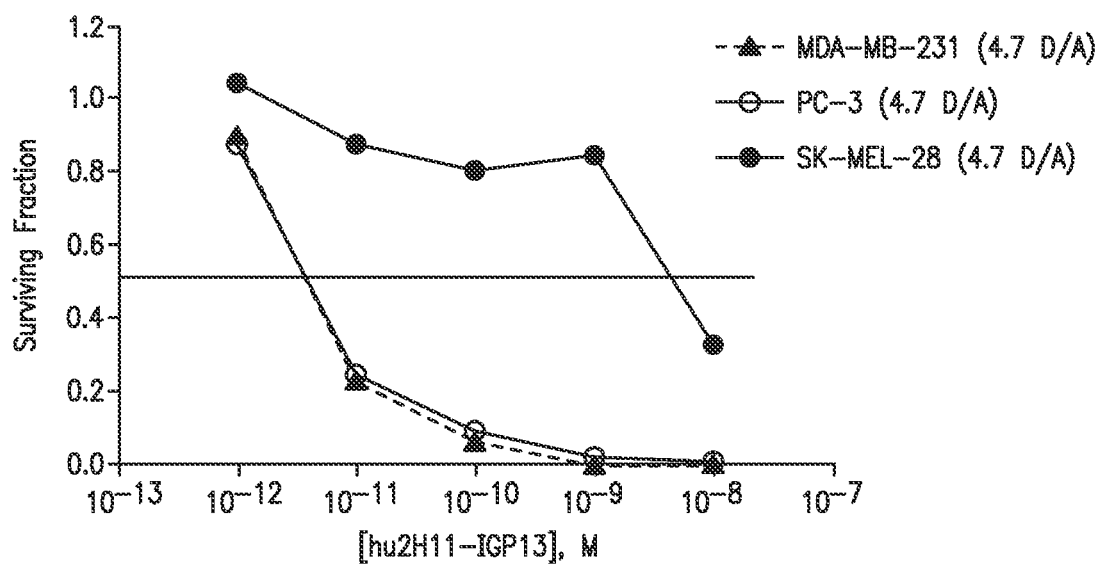
FIG. 16: In vitro cytotoxicity properties of hu2H11-IGP13 (compound of example 21) against PC3 (Ag+), MDA-MB-231 (Ag+) and SK-MEL-28 (Ag−) cells.
Figure 17:
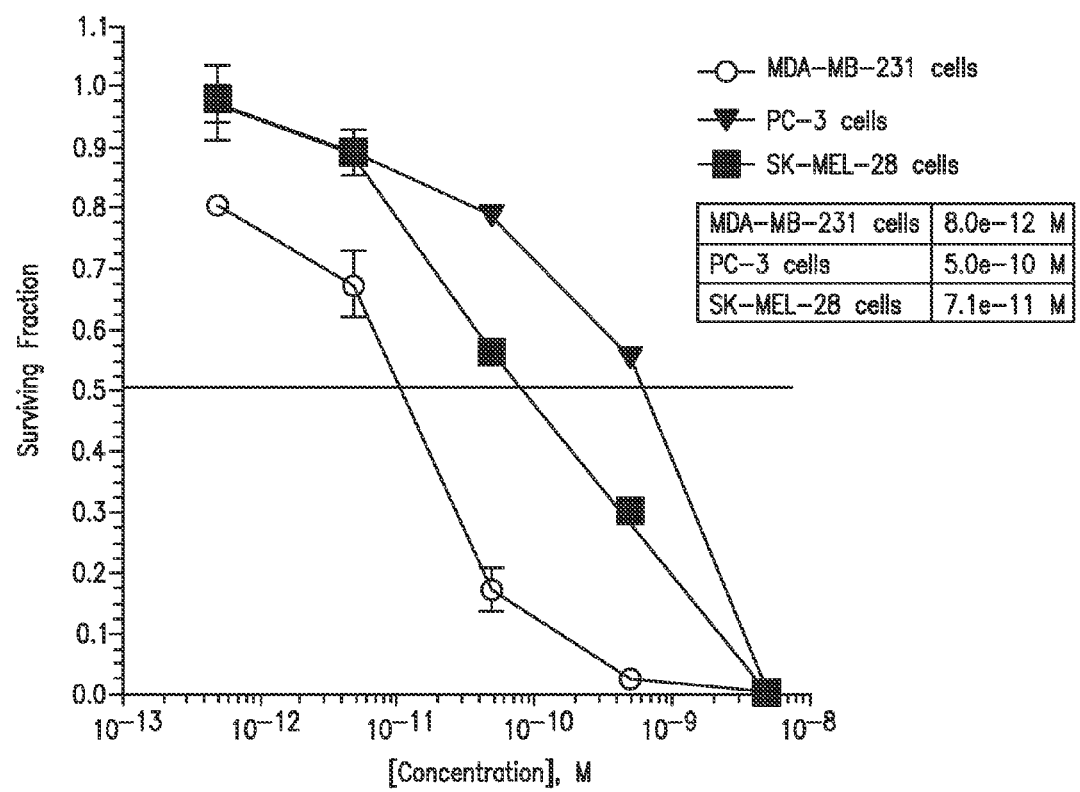
FIG. 17: In vitro cytotoxicity properties of 3-(2-{2-[2-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-ethoxy]-ethoxy}-ethoxy)-propionic acid methyl ester of ex. 5 in a continuous exposure clonogenic assay using MDA-MB-231, PC-3 and SK-MEL-28.
Figure 18:
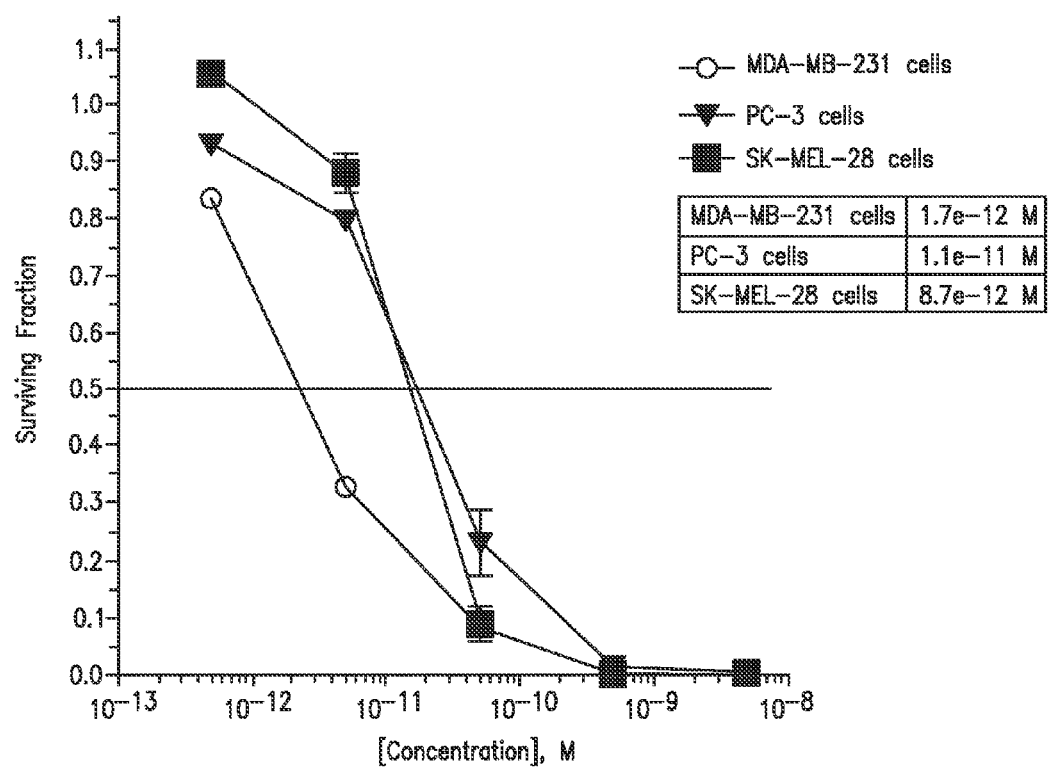
FIG. 18: In vitro cytotoxicity properties of 4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid methyl ester of ex. 6 in a continuous exposure clonogenic assay using MDA-MB-231, PC-3 and SK-MEL-28.
Figure 19:
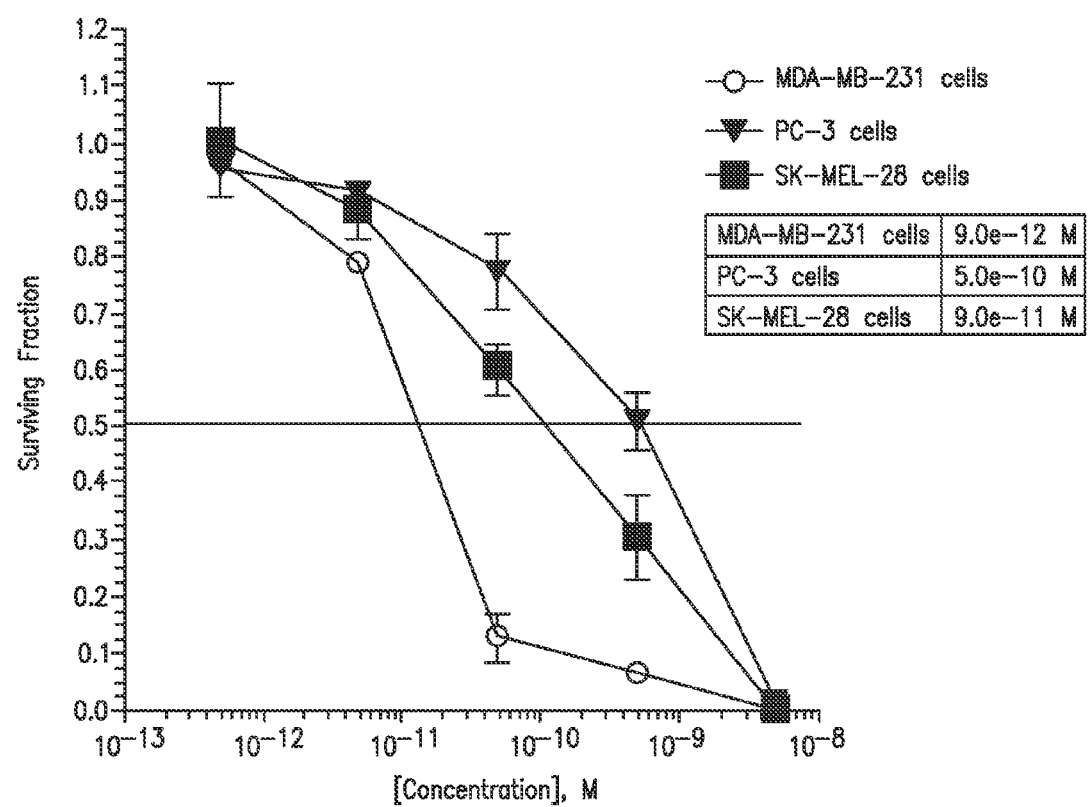
FIG. 19: In vitro cytotoxicity properties of N-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethyl]-N-methyl-succinamic acid methyl ester of ex. 7 in a continuous exposure clonogenic assay using MDA-MB-231, PC-3 and SK-MEL-28.
Figure 20:
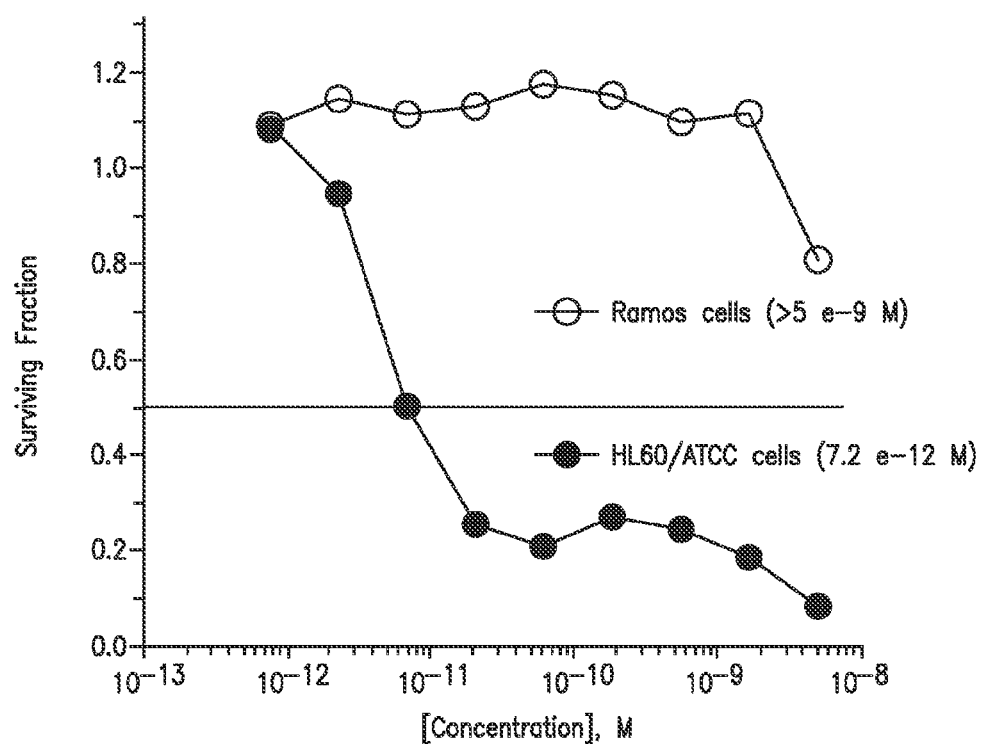
FIG. 20: In vitro cytotoxicity data for huMy9-6—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate from ex.11 on HL60/ATCC* (Ag+) and Ramos (Ag−) cells.
Figure 21:
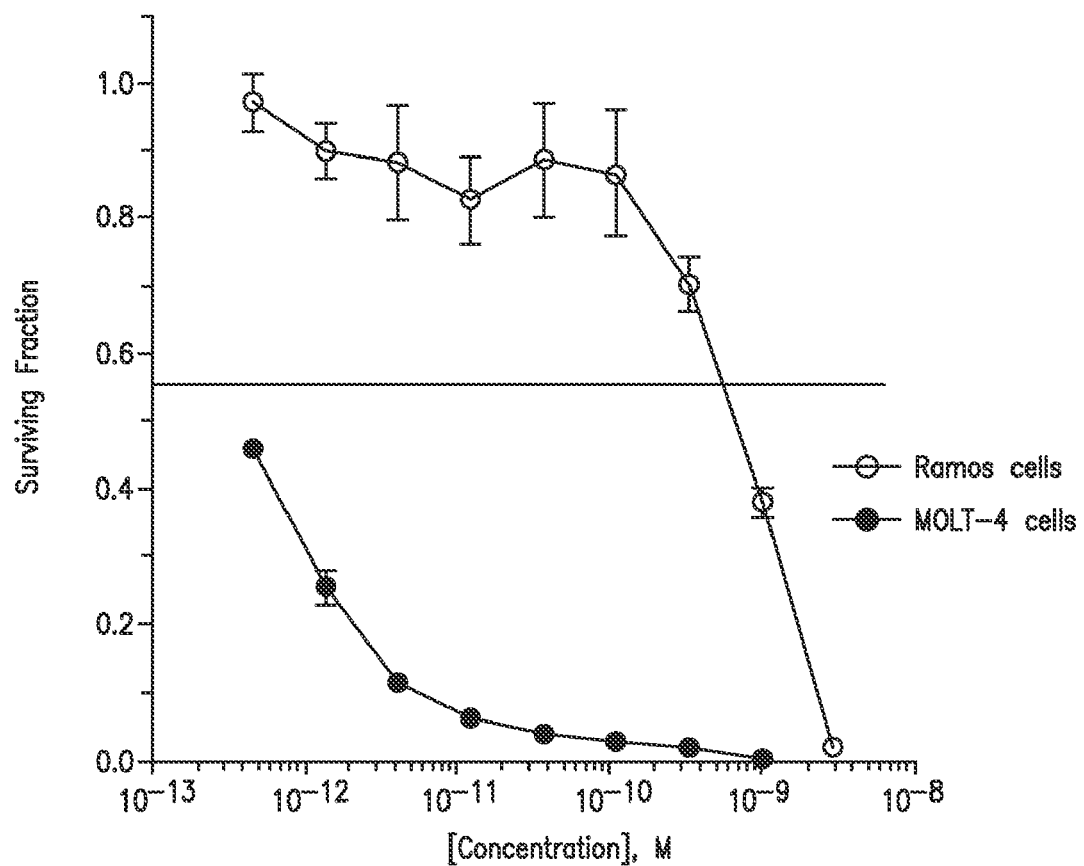
FIG. 21: In vitro cytotoxicity data for huB4—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate from ex. 12 on Ramos (Ag+) and MOLT-4 (Ag−) cells.
Figure 22:
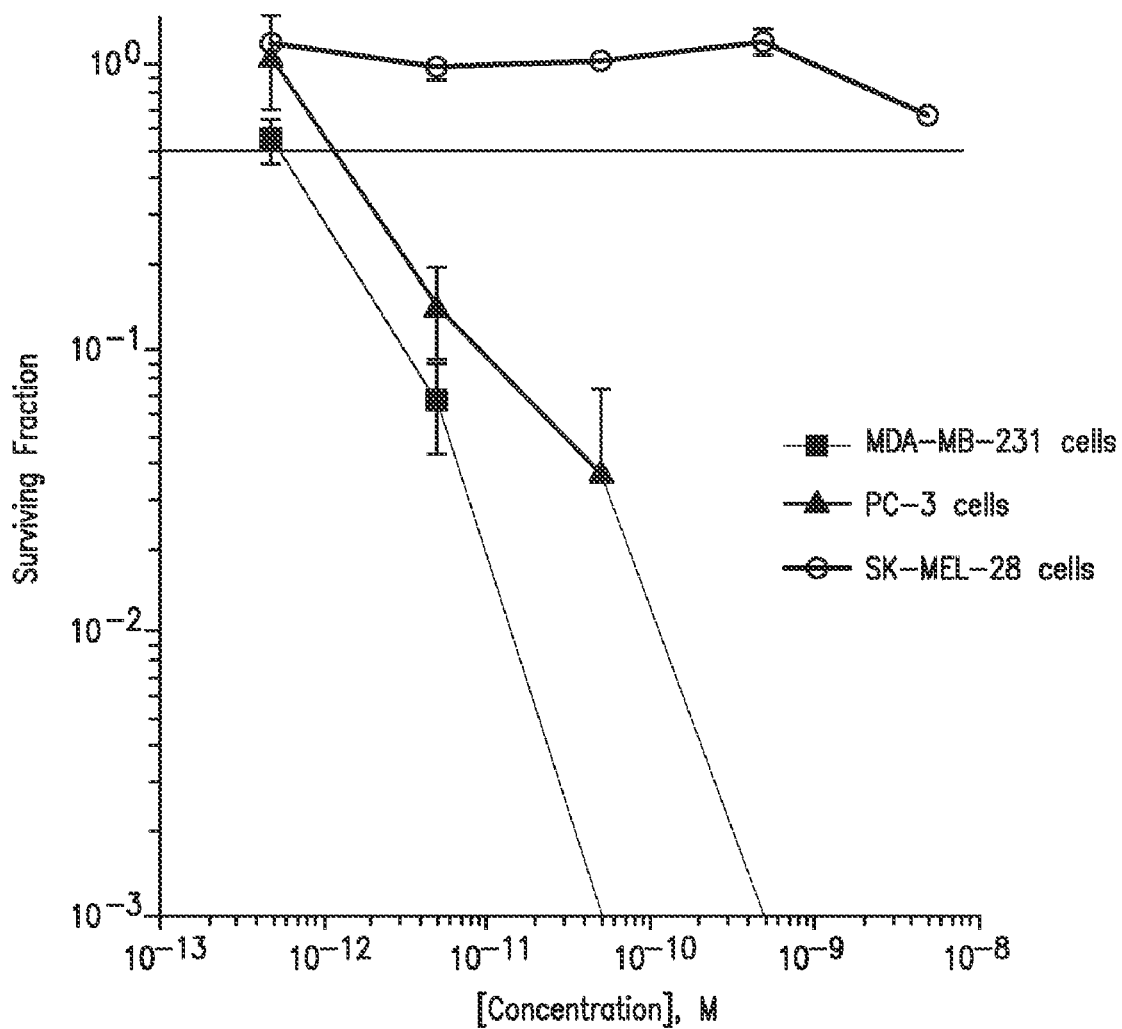
FIG. 22: In vitro cytotoxicity data for hu2H11—4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyryl conjugate from ex. 13 on MDA-MB-231 (Ag+), PC-3 (Ag+) and SK-MEL-28 (Ag−) cells.
Figure 23:
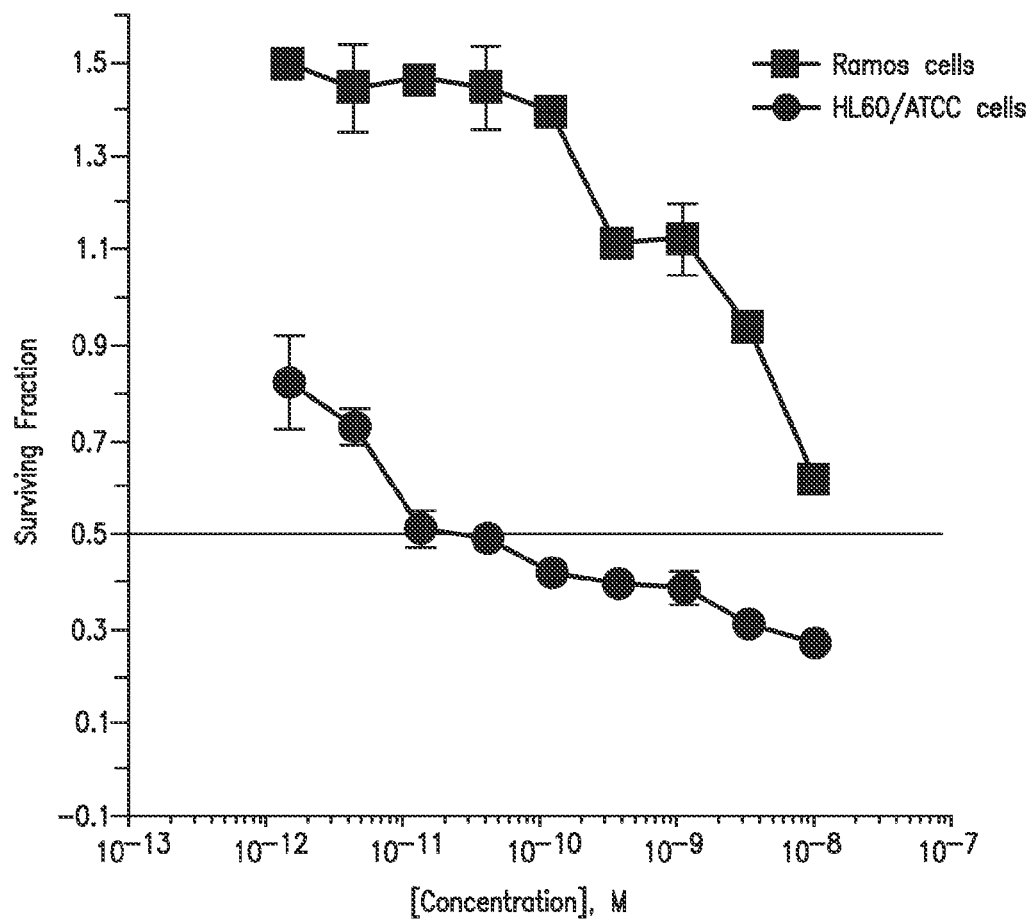
FIG. 23: In vitro cytotoxicity data for huMy9-6—3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate from ex. 14 on HL6-/ATCC (Ag+) and Ramos (Ag−) cells (Ramos @ 2000 cells/well, 5 day exposure developed for 4.5 hours with WST; HL60/ATCC @ 5000 cells/well, 7 day exposure developed with WST for 2 hours) [~IC50's; HL60/ATCC cells; 2.3e-11 M; Ramos cells; <1.0e-8 M]
Figure 24:
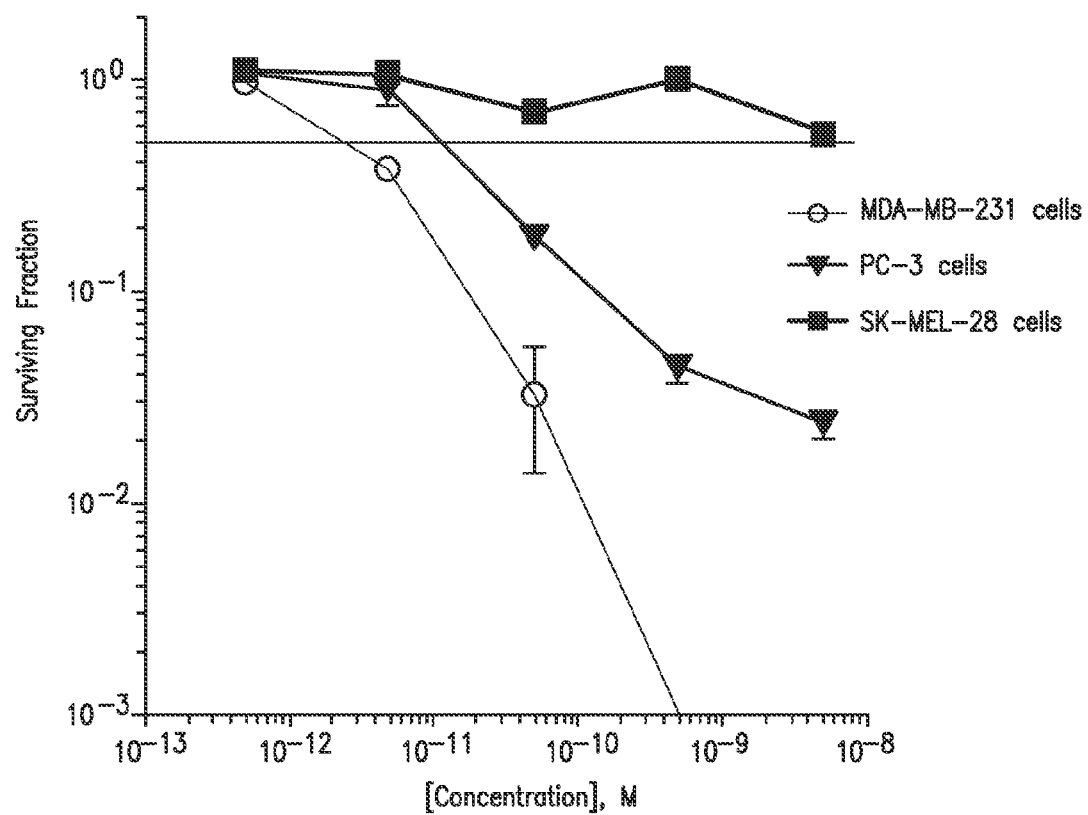
FIG. 24: In vitro cytotoxicity data for hu2H11—3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionyl conjugate from ex. 15 in a continuous exposure clonogenic assay using MDA-MB-231 (Ag+), PC-3 (Ag+) and SK-MEL-28 (Ag−) cells [~IC50's; MDA-MB-231 cells; 2.4e-12 M; PC-3 cells; 1.1e-11 M; SK-MEL-28 cells; 5.0e-9 M]

The cytotoxicity of the compounds and their specificity vs. the conjugates of the invention against MOLT-4, BJAB, HL60/QC, HL60/ATCC and Ramos cell lines were tested. Results are illustrated in FIGS. 1, 2, 3, 6 and 8.

Example 24

Clonogenic Assay

General Procedure to be Used

MDA-MB-231 cells were plated at 3000 cells per well in two separate 6-well plates; PC-3 and SK-MEL-28 cells were plated at 2000 cells per well in 2 separate plates. The test article(s) were added to give final concentrations of 0, 5× $10^{-13}$, 5×$10^{-12}$, 5×$10^{-11}$, 5×$10^{-10}$ and 5×$10^{-9}$ M per well (or similar dosage range) to each plate. For example, when cells are plated in 1 mL, and 1 mL of a 2× concentration of the test compound or conjugate is added to the appropriate wells to give the final desired concentration in 2 mls. The final solution of the test article was made in the same medium as the cell line; therefore, different dilutions of conjugate had to be made for each different cell line. The plates are placed in an incubator at 37° C. in 5% $CO_2$. Cell growth is monitored and when cells in the "0" (control) wells had formed colonies but were not confluent, usually 7 days for these cell lines, the supernatant was removed by aspiration. The cells were washed once with PBS (Phosphate Buffer Solution) and the supernatant aspirated. To each well, 0.5 ml per well of a 0.1% crystal violet/10% formalin/PBS was added. The plates were incubated at room temperature for 10-15 minutes. The supernatant was aspirated and the wells washed 3 times with distilled $H_2O$, and then air dried. Colonies in each well were counted and the number of colonies in each dosed well was divided by the number of colonies in the "0" well to give the surviving fraction. $IC_{50}$ values were then calculated from the data.

The compounds and the conjugate molecules disclosed in the examples have shown an $IC_{50}$ between <1 and 10000 pM (see enclosed figures and Table I for specific values for the various cell-lines).

TABLE I

In vitro data ($IC_{50}$ in pM) for the unconjugated tomaymicine derivatives for various cell-lines

|  | Ramos | HL60/ QC | HL60/ AT CC | MDA-MB-231 | PC-3 | SK-MEL-28 |
|---|---|---|---|---|---|---|
| compound 9 of scheme 2 (=IGP-08) | 2700 | 3500 | 2600 |  |  |  |
| compound 8 of scheme 2 (=IGP-08-OMe) | 8.0 | 1.1 | 4.0 | 17.0 | 27.0 | 10.0 |
| compound18 of scheme 3 (methyl ester of compound of ex.9) | 5000 |  | 5000 |  |  |  |

TABLE I-continued

In vitro data (IC$_{50}$ in pM) for the unconjugated tomaymicine derivatives for various cell-lines

| | Ramos | HL60/ QC | HL60/ AT CC | MDA-MB-231 | PC-3 | SK-MEL-28 |
|---|---|---|---|---|---|---|
| methyl ester of compound of ex.2 | 1.4 | | 12.0 | | | |
| methyl ester of compound of ex.1 | <0.76 | | <0.76 | | | |
| compound of ex.1 in the acid form | 580.0 | 1200.0 | 2000.0 | | | |
| methyl ester of compound of ex.4 | 1.2 | | 2.2 | 12.0 | 27.0 | 15.0 |
| methyl ester of compound of ex.3 | | | 12.0 | 16.0 | 7.4 | 9.7 |
| compound 29 of scheme 4 (=IGP-13-OMe) | | | | 50.0 | 300.0 | 710.0 |

TABLE I-continued

In vitro data (IC$_{50}$ in pM) for the unconjugated tomaymicine derivatives for various cell-lines

| | Ramos | HL60/QC | HL60/AT CC | MDA-MB-231 | PC-3 | SK-MEL-28 |
|---|---|---|---|---|---|---|
| methyl ester of compound of ex.5 | | | | 8.0 | 500.0 | 71.0 |
| methyl ester of compound of ex.6 | | | | 1.7 | 11.0 | 8.7 |
| methyl ester of compound of ex.7 | | | | 9.0 | 500.0 | 90.0 |

What is claimed is:

1. A compound of formula (I):

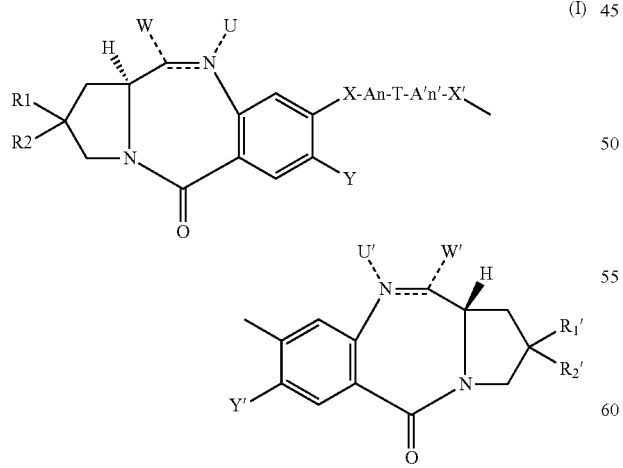

wherein:

----- represents an optional single bond;

===== represents either a single bond or a double bond;

provided that when ----- represents a single bond, U and U', the same or different, independently represent H, and W and W', the same or different, are independently selected from the group consisting of —OH, —OR, —OCOR, —COOR, —OCOOR, —OCONRR', —NRCONRR', —OCSNHR, —SH, —SR, —SOR, —SOOR, —SO$_3^-$, —NRSOOR', —NRR', —NROR', —NRCOR', —N$_3$, —CN, Hal, a trialkyl, triarylphosphonium and a cyclic carbamate, a cyclic thiocarbamate or a cyclic amine where U and W and/or U' and W' taken together with the nitrogen and carbon atoms to which they are attached form the cyclic carbamate, the cyclic thiocarbarmate or the cyclic amine;

and when ===== represents a double bond, U and U' are absent and W and W' represent H;

R1, R2, R1', R2' are the same or different and independently chosen from H, halide or alkyl optionally substituted by one or more Hal, CN, NRR', CF$_3$, OR, aryl, Het, or S(O)$_q$R, or R1 and R2 and R1' and R2' form together a double bond containing group =B and =B' respectively;

B and B' are the same or different and independently chosen from Alkenyl being optionally substituted by one or more Hal, CN, NRR', CF$_3$, OR, SR, SOR, SO$_2$R, Aryl, Het, or B and B' represent an oxygen atom;

X, X' are —O—;
A, A' are the same or different and independently chosen from Alkyl or Alkenyl, each being optionally substituted by one or more Hal, CN, NRR', CF$_3$, OR, SR, SOR, SO$_2$R, Aryl, Het, Alkyl, Alkenyl;
Y, Y' are the same or different and independently chosen from H, OR;
T is —NR— or a 4 to 10-membered aryl, cycloalkyl, heterocyclic, heteroaryl or a linear or branched alkyl, each being substituted by one or more non-cleavable linker(s) and optionally substituted by one or more of Hal, CN, NRR', CF$_3$, R, OR, SOR or SO$_2$R;
n, n', equal or different, are 0 or 1;
q is 0, 1 or 2; and
R, R' are equal or different and independently chosen from H, Alkyl, Aryl, each being optionally substituted by Hal, CN, COOH, COOR, CONHR, CONRR', NRR', CF$_3$, R, OR, SOR, SO$_2$R, Aryl, Het;
wherein the linker:
(A) is of formula -G-D-(Z)$_p$C(=O)—Z'R'' wherein:
G is a single, a double or a triple bond, —O—, —S— or —NR—;
D is a single bond or -E-, -E-NR—F—, -E-O—, -E-O—F—, -E-NR—CO—, -E-CONR—, -E-NR—CO—F—, -E-CO—NR—F—, -E-CO—, —CO-E-, -E-CO—F, -E-S—, -E-S—F—, -E-NR—CS—, -E-CS—NR—, -E-NR—CS—F—, -E-CS—NR—F—;
E and F are the same or different and are independently chosen from linear or branched —(OCH$_2$CH$_2$)$_i$Alkyl(OCH$_2$CH$_2$)$_j$—, -Alkyl(OCH$_2$CH$_2$)$_i$-Alkyl-, —(OCH$_2$CH$_2$)$_j$—, —(OCH$_2$CH$_2$)$_i$Cycloalkyl(OCH$_2$CH$_2$)$_j$—, —(OCH$_2$CH$_2$)$_i$Heterocyclic(OCH$_2$CH$_2$)$_j$—, —(OCH$_2$CH$_2$)$_i$Aryl(OCH$_2$CH$_2$)$_j$—, —(OCH$_2$CH$_2$)$_i$Heteroaryl(OCH$_2$CH$_2$)$_j$—, -Alkyl-(OCH$_2$CH$_2$)$_i$Alkyl(OCH$_2$CH$_2$)$_j$—, -Alkyl-(OCH$_2$CH$_2$)$_i$—, -Alkyl-(OCH$_2$CH$_2$)$_i$Cycloalkyl(OCH$_2$CH$_2$)$_j$—, -Alkyl(OCH$_2$CH$_2$)$_i$Heterocyclic(OCH$_2$CH$_2$)$_j$—, -Alkyl-(OCH$_2$CH$_2$)$_i$Aryl(OCH$_2$CH$_2$)$_j$—, -Alkyl(OCH$_2$CH$_2$)$_i$Heteroaryl(OCH$_2$CH$_2$)$_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
i and j, identical or different are integers and independently chosen from 0, 1 to 2000;
Z is a linear or branched Alkyl, cycloalkyl, Aryl, heteroaryl, heterocyclyl, aralkyl, cycloalkyl, heteroaralkyl, or heterocyclylalkyl, optionally substituted by solubilizing functions such as amino, ether, sulfonic and carboxylic groups;
p is 0 or 1; and
(B) is selected from the group consisting of:
—(CR$_{13}$R$_{14}$)$_t$(CR$_{15}$R$_{16}$)$_u$(OCH$_2$CH$_2$)$_y$COZ'R'',
—(CR$_{13}$R$_{14}$)$_t$(OCH$_2$CH$_2$)$_y$O(CR$_{15}$R$_{16}$)$_u$COZ'R'',
—(CR$_{13}$R$_{14}$)$_t$(CR$_{17}$=CR$_{18}$)(CR$_{15}$R$_{16}$)$_u$(OCH$_2$CH$_2$)$_y$COZ'R'',
—(CR$_{13}$R$_{14}$)$_t$(NR$_{19}$CO)(CR$_{15}$R$_{16}$)$_u$(OCH$_2$CH$_2$)$_y$COZ'R'',
—(CR$_{13}$R$_{14}$)$_t$(OCO)(CR$_{15}$R$_{16}$)$_u$(OCH$_2$CH$_2$)$_y$COZ'R'',
—(CR$_{13}$R$_{14}$)$_t$(CO)(CR$_{15}$R$_{16}$)$_u$(OCH$_2$CH$_2$)$_y$COZ'R'',
—(CR$_{13}$R$_{14}$)$_t$(CONR$_{19}$)(CR$_{15}$R$_{16}$)$_u$(OCH$_2$CH$_2$)$_y$COZ'R'',
—(CR$_{13}$R$_{14}$)$_t$-phenyl-CO(CR$_{15}$R$_{16}$)$_u$COZ'R'',
—(CR$_{13}$R$_{14}$)$_t$-furyl-CO(CR$_{15}$R$_{16}$)$_u$COZ'R'',
—(CR$_{13}$R$_{14}$)$_t$-oxazolyl-CO(CR$_{15}$R$_{16}$)$_u$COZ'R'',
—(CR$_{13}$R$_{14}$)$_t$-thiazolyl-CO(CR$_{15}$R$_{16}$)$_u$COZ'R'',
—(CR$_{13}$R$_{14}$)$_t$-thienyl-CO(CR$_{15}$R$_{16}$)$_u$COZ'R'',
—(CR$_{13}$R$_{14}$)$_t$-imidazolyl-CO(CR$_{15}$R$_{16}$)$_u$COZ'R'',
—(CR$_{13}$R$_{14}$)$_t$piperazino-CO(CR$_{15}$R$_{16}$)$_u$COZ'R'',
—(CR$_{13}$R$_{14}$)$_t$-phenyl-QCOZ'R'',
—(CR$_{13}$R$_{14}$)$_t$-furyl-QCOZ'R'', —(CR$_{13}$R$_{14}$)$_t$-oxazolyl-QCOZ'R'',
—(CR$_{13}$R$_{14}$)$_t$-thiazolyl-QCOZ'R'', —(CR$_{13}$R$_{14}$)$_t$-thienyl-QCOZ'R'',
—(CR$_{13}$R$_{14}$)$_t$-imidazolyl-QCOZ'R'', —(CR$_{13}$R$_{14}$)$_t$-piperazino-QCOZ'R'',
—(C≡C)—(CR$_{13}$R$_{14}$)$_t$(CR$_{15}$R$_{16}$)$_u$(OCH$_2$CH$_2$)$_y$COZ'R'',
—O(CR$_{13}$R$_{14}$)$_t$(CR$_{15}$R$_{16}$)$_u$(OCH$_2$CH$_2$)$_y$COZ'R'',
—O(CR$_{13}$R$_{14}$)$_t$(NR$_{19}$CO)(CR$_{15}$R$_{16}$)$_u$(OCH$_2$CH$_2$)$_y$COZ'R'',
—O(CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—O-phenyl-QCOZ'R'', —O-furyl-QCOZ'R'', —O-oxazolyl-QCOZ'R'',
—O-thiazolyl-Q COZ'R'', —O-thienyl-QCOZ'R'', —O-imidazolyl-QSCOZ'R'',
—O-morpholino-QCOZ'R'', —O-piperazino-QCOZ'R'',
—OCO(CR$_{13}$R$_{14}$)$_t$(NR$_{19}$CO)(CR$_{15}$R$_{16}$)$_u$ (OCH$_2$CH$_2$)$_y$COZ'R'',
—OCO—(CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—OCONR$_{12}$(CR$_{13}$R$_{14}$)$_t$(CR$_{15}$R$_{16}$)$_u$ (OCH$_2$CH$_2$)$_y$COZ'R'',
—OCO-phenyl-QCOZ'R'', —OCO-furyl-QCOZ'R'', —OCO-oxazolyl-QCOZ'R'',
—OCO-thiazolyl-QCOZ'R'', —OCO-thienyl-QCOZ'R'', —OCO-imidazolyl-QCOZ'R'',
—OCO-piperazino-QCOZ'R'', or
—CO(CR$_{13}$R$_{14}$)$_t$(CR$_{15}$R$_{16}$)$_u$ (OCH$_2$CH$_2$)$_y$COZ'R'',
—CO—(CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—CONR$_{12}$(CR$_{13}$R$_{14}$)$_t$(CR$_{15}$R$_{16}$)$_u$ (OCH$_2$CH$_2$)$_y$COZ'R'',
—CO-phenyl-QCOZ'R'', —CO-furyl-QCOZ'R''-CO-oxazolyl-QCOZ'R'',
—CO-thiazolyl-QCOZ'R'', —CO-thienyl-QCOZ'R'', —CO-imidazolyl-QCOZ'R'',
—CO-piperazino-QCOZ'R'', —CO-piperidino-QCOZ'R'',
—NR$_{19}$(CR$_{13}$R$_{14}$)$_t$(CR$_{15}$R$_{16}$)$_u$(OCH$_2$CH$_2$)$_y$COZ'R'',
—NR$_{19}$CO(CR$_{13}$R$_{14}$)$_t$(CR$_{15}$R$_{16}$)$_u$(OCH$_2$CH$_2$)$_y$COZ'R'',
—NR$_{19}$(CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—NR$_{19}$CO(CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—NR$_{19}$CONR$_{12}$(CR$_{13}$R$_{14}$)$_t$(CR$_{15}$R$_{16}$)$_u$(OCH$_2$CH$_2$)$_y$COZ'R'',
—NR$_{19}$CONR$_{12}$ (CR$_{13}$R$_{14}$)$_t$ (CR$_{17}$=CR$_{18}$)(CR$_{15}$R$_{16}$)$_u$ (OCH$_2$CH$_2$)$_y$COZ'R'',
—NR$_{19}$CO-phenyl-QCOZ'R'', —NR$_{19}$CO-furyl-QCOZ'R'', —NR$_{19}$CO-oxazolyl-QCOZ'R'', —NR$_{19}$CO-thiazolyl-QCOZ'R'', —NR$_{19}$CO-thienyl-QCOZ'R'',
—NR$_{19}$CO-imidazolyl-QCOZ'R'', —NR$_{19}$CO-morpholino-QCOZ'R'',
—NR$_{19}$CO-piperazino-QCOZ'R'', —NR$_{19}$CO-piperidino-QCOZ'R'',
—NR$_{19}$-phenyl-QCOZ'R'', —NR$_{19}$-furyl-QCOZ'R'', —NR$_{19}$-oxazolyl-QCOZ'R'',
—NR$_{19}$-thiazolyl-QCOZ'R'', —NR$_{19}$-thienyl-QCOZ'R'', —NR$_{19}$-imidazolyl-QCOZ'R'',
—NR$_{19}$-piperazino-QCOZ'R'', —NR$_{19}$-piperidino-QCOZ'R'',
—NR$_{19}$CO—NR$_{12}$-phenyl-QCOZ'R'', —NR$_{19}$CO—NR$_{12}$-oxazolyl-QCOZ'R'',
—NR$_{19}$CO—NR$_{12}$-thiazolyl-QCOZ'R'', —NR$_{19}$CO—NR$_{12}$-thienyl-QCOZ'R'',
—NR$_{19}$CO—NR$_{12}$-piperidino-QCOZ'R'',
—S(O)$_q$(CR$_{13}$R$_{14}$)$_t$(CR$_{15}$R$_{16}$)$_u$(OCH$_2$CH$_2$)$_y$COZ'R'',
—S(O)$_q$(CR$_{13}$R$_{14}$)$_t$(CR$_{17}$=CR$_{18}$)(CR$_{15}$R$_{16}$)$_u$(OCH$_2$CH$_2$)$_y$COZ'R'',
—SCONR$_{12}$(CR$_{13}$R$_{14}$)$_t$(CR$_{15}$R$_{16}$)$_u$(OCH$_2$CH$_2$)$_y$COZ'R'',
—SCO-piperazino-QCOZ'R'', and —SCO-piperidino-QCOZ'R'',
wherein:
Q is a direct link or a linear alkyl or branched alkyl having from 1-10 carbon atoms or a polyethylene glycol spacer with 2 to 20 repeating ethyleneoxy units;

R$_{19}$ and R$_{12}$ are the same or different and are linear alkyl, branched alkyl or cyclic alkyl having from 1 to 10 carbon atoms, or simple or substituted aryl or heterocyclic, and R$_{12}$ can in addition be H;
R$_{13}$, R$_{14}$, R$_{15}$ and R$_{16}$ are the same or different and are H or a linear or branched alkyl having from 1 to 4 carbon atoms;
R$_{17}$ and R$_{18}$ are H or alkyl;
q is 0, 1 or 2;
u is an integer from 1 to 10 and can also be 0;
t is an integer from 1 to 10 and can also be 0;
y is an integer from 1 to 20 and can also be 0; and
(C) —C(=O)—Z'R'' is a carbonyl containing function wherein Z' represents a single bond or —O—, —S—, —NR— and R'' represents H, Alkyl, Cycloalkyl, Aryl, heteroaryl or heterocyclic, each being optionally substituted by one or more Hal, CN, NRR', CF$_3$, R, OR, SOR, SO$_2$R, Aryl, Het;
or a pharmaceutically acceptable salt thereof;
or optical isomers, racemates, diastereomers or enantiomers of said compound.

2. The compound according to claim 1 wherein W and W' are the same or different and are —OH, —OMe, —OEt, —NHCONH$_2$, or —SMe;
or a pharmaceutically acceptable salt thereof;
or optical isomers, racemates, diastereomers or enantiomers of said compound.

3. The compound according to claim 1 having the following formula (II):

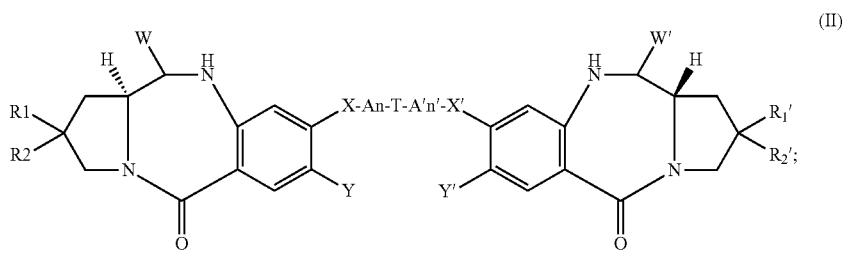

or a pharmaceutically acceptable salt thereof;
or optical isomers, racemates, diastereomers or enantiomers of said compound.

4. The compound according to claim 1, having formula:

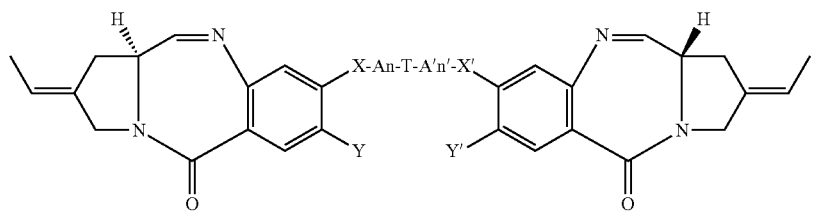

or

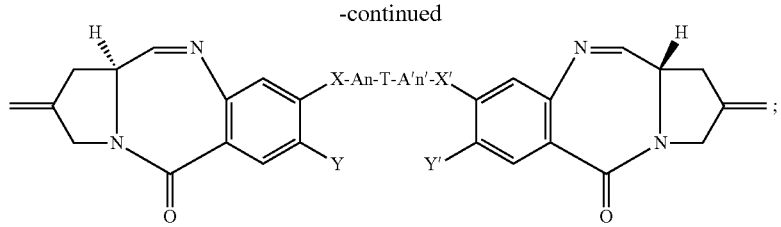

or a pharmaceutically acceptable salt thereof;

or optical isomers, racemates, diastereomers or enantiomers of said compound.

5. The compound according to claim 1 wherein A=A';
or a pharmaceutically acceptable salt thereof;
or optical isomers, racemates, diastereomers or enantiomers of said compound.

6. The compound according to claim 1 wherein A=A'=linear unsubstituted alkyl;
or a pharmaceutically acceptable salt thereof;
or optical isomers, racemates, diastereomers or enantiomers of said compound.

7. The compound according to claim 1 wherein Y=Y';
or a pharmaceutically acceptable salt thereof;
or optical isomers, racemates, diastereomers or enantiomers of said compound.

8. The compound according claim 2 wherein Y=Y'=OAlkyl;
or a pharmaceutically acceptable salt, optical isomer, racemate, diastereomer or enantiomer of said compound.

9. The compound according to claim 1 wherein T is a 4 to 10-membered aryl or heteroaryl;
or a pharmaceutically acceptable salt thereof;
or optical isomers, racemates, diastereomers or enantiomers of said compound.

10. The compound according to claim 1 wherein T is a phenyl or pyridyl group;
or a pharmaceutically acceptable salt thereof;
or optical isomers, racemates, diastereomers or enantiomers of said compound.

11. The compound according to claim 1, wherein G is a single bond or —O—;
or a pharmaceutically acceptable salt thereof;
or optical isomers, racemates, diastereomers or enantiomers of said compound.

12. The compound according to claim 1, wherein D is a single bond or -E- or -E-O—;
or a pharmaceutically acceptable salt thereof;
or optical isomers, racemates, diastereomers or enantiomers of said compound.

13. The compound according claim 1, wherein D is -E-;
or a pharmaceutically acceptable salt thereof;
or optical isomers, racemates, diastereomers or enantiomers of said compound.

14. The compound according to claim 13 wherein E is linear or branched -Alkyl- or -Alk(OCH$_2$CH$_2$)$_i$—;
or a pharmaceutically acceptable salt thereof;
or optical isomers, racemates, diastereomers or enantiomers of said compound.

15. The compound according to claim 1, wherein Z is linear or branched -Alkyl-;
or a pharmaceutically acceptable salt thereof;
or optical isomers, racemates, diastereomers or enantiomers of said compound.

16. The compound according claim 1 wherein p is 0;
or a pharmaceutically acceptable salt thereof;
or optical isomers, racemates, diastereomers or enantiomers of said compound.

17. The compound according to claim 1 wherein Z' is a single bond or O;
or a pharmaceutically acceptable salt thereof;
or optical isomers, racemates, diastereomers or enantiomers of said compound.

18. The compound according to claim 1 wherein Z' is O;
or a pharmaceutically acceptable salt thereof;
or optical isomers, racemates, diastereomers or enantiomers of said compound.

19. The compound according to claim 1 wherein R" is H or linear or branched -Alkyl- or optionally substituted heterocyclic;
or a pharmaceutically acceptable salt thereof;
or optical isomers, racemates, diastereomers or enantiomers of said compound.

20. The compound according to claim 1 wherein R" is H or alkyl or a succinimide group

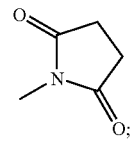

or a pharmaceutically acceptable salt thereof;
or optical isomers, racemates, diastereomers or enantiomers of said compound.

21. The compound according claim 1 wherein —Z'R" is —OH, —Oalkyl or

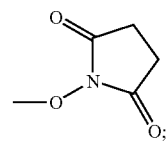

or a pharmaceutically acceptable salt thereof;
or optical isomers, racemates, diastereomers or enantiomers of said compound.

22. The compound according to claim 1 wherein said linker is selected from the group consisting of:

—$(CR_{13}R_{14})_t(CR_{15}R_{16})_u(OCH_2CH_2)_yCOZ'R''$;
—$(CR_{13}R_{14})_t(OCH_2CH_2)_yO(CR_{15}R_{16})_uCOZ'R''$;
—$O(CR_{13}R_{14})_t(CR_{15}R_{16})_u(OCH_2CH_2)_yCOZ'R''$;
—$O(CR_{13}R_{14})_t(NR_{19}CO)(CR_{15}R_{16})_u(OCH_2CH_2)_yCOZ'R''$;
—$(C\equiv C)$—$(CR_{13}R_{14})_t(CR_{15}R_{16})_u(OCH_2CH_2)_yCOZ'R''$;
—$O(CR_{13}R_{14})_tCOZ'R''$;
—$(OCH_2CH_2)_yCOZ'R''$;
—$(C\equiv C)$—$(CR_{13}R_{14})_tCOZ'R''$;
—$O(CR_{13}R_{14})_t(NR_{19}CO)(CR_{15}R_{16})_uCOZ'R''$; and
—$(CR_{13}R_{14})_t(OCH_2CH_2)_yCOZ'R''$;

or a pharmaceutically acceptable salt thereof;
or optical isomers, racemates, diastereomers or enantiomers of said compound.

23. A compound of formula:

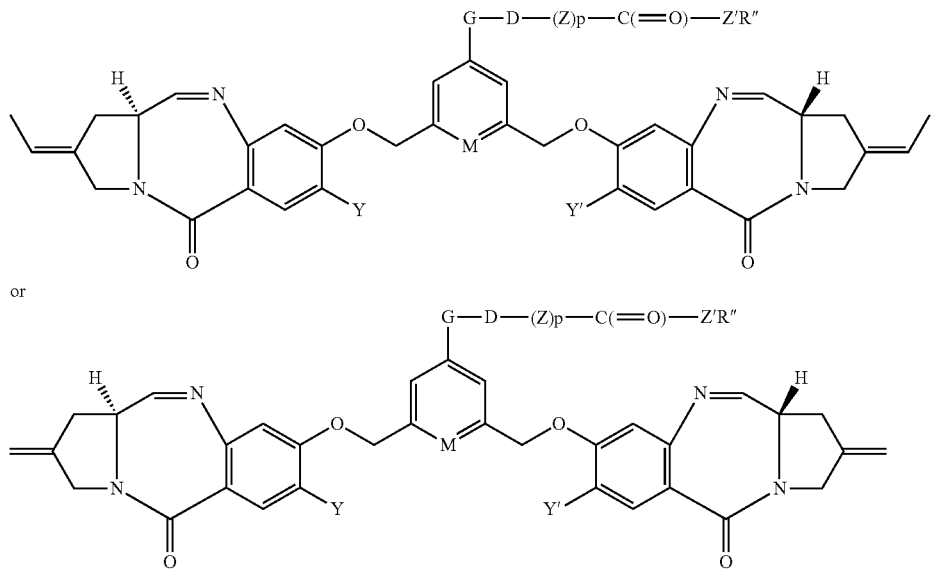

wherein:
-G-D-(Z)$_p$—C(=O)—Z'R" is as defined in claim 1;
M represents CH or N; and
Y=Y'=OMe;
or a pharmaceutically acceptable salt thereof;
or optical isomers, racemates, diastereomers or enantiomers of said compound.

24. A compound selected from the group consisting of:
4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-butyric acid;
4-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-acetic acid;
3-(2-{2-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethoxy]-ethoxy}-ethoxy)-propionic acid;
6-(3,5-Bis-[(S)-2-eth-(E)-ylidene-7-methoxy-1,2,3,11a-tetrahydro-pyrrolo[2,1c][1,4] benzodiazepin-5-one-8-yloxymethyl]-phenyl)-hex-5-ynoic acid;
3-(2-{2-[2-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-ethoxy]-ethoxy}-ethoxy)-propionic acid;
4-(2,6-Bis-[(S)-2-eth-(E)-ylidene-7-methoxy-1,2,3,11a-tetrahydro-pyrrolo[2,1c][1,4]benzodiazepin-5-one-8-yloxymethyl]-pyridin-4-yloxy)-butyric acid;
N-[2-(3,5-Bis-[(S)-2-eth-(E)-ylidene-7-methoxy-1,2,3,11a-tetrahydro-pyrrolo[2,1c][1,4]benzodiazepin-5-one-8-yloxymethyl]-phenoxy)-ethyl]-N-methyl-succinamic acid;
4-(3,5-Bis-[(S)-2-methylidene-7-methoxy-1,2,3,11a-tetrahydro-pyrrolo[2,1 c][1,4] benzodiazepin-5-one-8-yloxymethyl]-phenyl)-propanoic acid;
(2-{2-[2-(2-{3-[3,5-Bis-(7-methoxy-2-methylene-5-oxo-2,3 ,5,11a-tetrahydro-1H-benzo[e]pyrrolo[1,2-a][1,4] diazepin-8-yloxymethyl)-phenyl]-propoxy}-ethoxy) ethoxy]-ethoxy}-ethoxy)-acetic acid; and
(3-{2-[2-(2-{3-[3,5-Bis-(7-methoxy-2-methylene-5-oxo-2,3 ,5,11a-tetrahydro-1H-benzo[e]pyrrolo[1,2-a][1,4] diazepin-8-yloxymethyl)-phenyl]-propoxy}-ethoxy) ethoxy]-ethoxy}-ethoxy)-propanoic acid;
and the corresponding N-hydroxysuccinimidyl esters thereof,
or a pharmaceutically acceptable salt thereof;
or optical isomers, racemates, diastereomers or enantiomers of said compound.

25. A pharmaceutical composition comprising a compound according to claim 1 together with a pharmaceutically acceptable carrier.

26. The compound of claim 1, wherein Y=Y'=OMe.

27. The compound of claim 1, wherein n=n'=1.

28. The compound of claim 1, wherein B=B'==CH$_2$ or =CH—CH$_3$.

* * * * *